(12) United States Patent
Kapulnik et al.

(10) Patent No.: US 10,208,007 B2
(45) Date of Patent: Feb. 19, 2019

(54) USE OF STRIGOLACTONES AND STRIGOLACTONE ANALOGS FOR TREATING PROLIFERATIVE CONDITIONS

(71) Applicants: The State of Israel, Ministry of Agriculture & Rural Development, Agricultural Research Organization (ARO), Bet Dagan (IL); Georgetown University, Washington, DC (US)

(72) Inventors: Yoram Kapulnik, Karmei Yosef (IL); Hinanit Koltai, Rishon LeZion (IL); Ronit Yarden, Bethesda, MD (US); Cristina Prandi, Turin (IT)

(*) Notice: Subject to any disclaimer, the term of this patent is extended or adjusted under 35 U.S.C. 154(b) by 358 days.

(21) Appl. No.: 14/345,371

(22) PCT Filed: Sep. 20, 2012

(86) PCT No.: PCT/IL2012/050381
§ 371 (c)(1),
(2) Date: Mar. 17, 2014

(87) PCT Pub. No.: WO2013/042124
PCT Pub. Date: Mar. 28, 2013

(65) Prior Publication Data
US 2014/0323563 A1  Oct. 30, 2014

Related U.S. Application Data

(60) Provisional application No. 61/614,965, filed on Mar. 23, 2012, provisional application No. 61/537,062, filed on Sep. 21, 2011.

(51) Int. Cl.
| | | |
|---|---|---|
| A61K 31/403 | (2006.01) | |
| C07D 307/93 | (2006.01) | |
| A61K 31/404 | (2006.01) | |
| A61K 31/365 | (2006.01) | |
| C07D 407/12 | (2006.01) | |
| C07D 405/12 | (2006.01) | |
| C07D 409/14 | (2006.01) | |
| C07D 495/04 | (2006.01) | |
| A61K 33/24 | (2006.01) | |

(52) U.S. Cl.
CPC .......... *C07D 307/93* (2013.01); *A61K 31/365* (2013.01); *A61K 31/403* (2013.01); *A61K 31/404* (2013.01); *C07D 405/12* (2013.01); *C07D 407/12* (2013.01); *C07D 409/14* (2013.01); *C07D 495/04* (2013.01); *A61K 33/24* (2013.01)

(58) Field of Classification Search
None
See application file for complete search history.

(56) References Cited

U.S. PATENT DOCUMENTS

2008/0318773 A1   12/2008   Becard et al.

FOREIGN PATENT DOCUMENTS

| CN | 101730469 A | 6/2010 |
|---|---|---|
| WO | 2005077177 | 8/2005 |
| WO | 2008152091 | 12/2008 |
| WO | 2008152092 | 12/2008 |
| WO | 2010128112 | 11/2010 |
| WO | 2012/056113 | 5/2012 |

OTHER PUBLICATIONS

Bhattacharya et al., Org.Biomol.Chem., 2009, vol. 7, pp. 3413-3420.*
Amos and Lotan, 1990, Methods Enzymol., 190, 217-225.
Asami and Ito, 2012, "Design and Synthesis of Function Regulators of Plant Hormones and their Application to Physiology and Genetics", J. Synthetic Org. Chem. Japan, 70:36-49. (English abstract).
Boyer et al., 2012, "Structure-Activity Relationship Studies of Strigolactone-Related Molecules for Branching Inhibition in Garden Pea: Molecule Design for Shoot Branching", Plant Physiology, 159: 1524-1544.
Burger and Gupta, 2009, High Aldehyde Dehydrogenase Activity: A Novel Functional Marker of Murine Prostate Stem/Progenitor Cells, Stem Cells, 27(9): 2220-2228.
Chen et al., 2010, "Stereochemistry, Total Synthesis, and Biological Evaluation of the New Plant Hormone Solanacol", Chemistry European Journal, 16:13941-13945.
Dor et al: 2011, "The synthetic strigolactone GR24 influences the growth pattern of phytopathogenic fungi", Planta, 234:419-427.
Dun et al., 2009, "Strigolactones: discovery of the elusive shoot branching hormone", Trends Plant Sci., 14, 364-372.
Galindo et al., 2002, "SAR studies of Sesquiterpene Lactones as Orobanche cumana Seed Germination Stimulants", J. Agricultural and Food Chemistry, 50:1911-1917.
Ginestier et al., 2007, "ALDH1 Is a Marker of Normal and Malignant Human Mammary Stem Cells and a Predictor of Poor Clinical Outcome", Cell Stem Cell, 1: 555-567.
Haldar et al., 1996, "Taxol Induces bcl-2 Phosphorylation and Death of Prostate Cancer Cells", Cancer Res. 56: 1253-1255.
Jiang et al., 2009, "Aldehyde Dehydrogenase 1 Is a Tumor Stem Cell-Associated Marker in Lung Cancer", Mol. Cancer Res., 7(3): 330-338.
Kitahara et al., 2011, "First synthesis of (=−)-sorgomol, the germination stimulant for root parasitic weeds isolated from Sorghum bicolor", Tetrahedron Lett., 52:724-726.

(Continued)

*Primary Examiner* — Jeffrey S Lundgren
*Assistant Examiner* — Stephanie K Springer
(74) *Attorney, Agent, or Firm* — Law Offices of Albert Wai-Kit Chan, PLLC

(57) ABSTRACT

Compound of formula X wherein $P_1$ is a fused-ring system comprising one 6-membered and two 5-membered rings; v indicates an S or R configuration; or individual isomers or pharmaceutically acceptable salts thereof, or mixtures thereof, in the preparation of an active agent for preventing or inhibiting cell proliferation or for inducing cell death.

4 Claims, 37 Drawing Sheets

Specification includes a Sequence Listing.

(56) References Cited

OTHER PUBLICATIONS

Li et al., 2008, "Intrinsic Resistance of Tumorigenic Breast Cancer Cells to Chemotherapy", J. Nat. Cancer Inst., vol. 100(9): 672-679.
Malik et al., 2010, "A new efficient synthesis of GR24 and dimethyl A-ring analogues, germinating agents for seeds of the parasitic weeds Striga and Orobanche spp.", Tetrahedron, 66:7198-7203.
Martinez et al: 2001, "Effects of a fraction from maize root exudates on haploid strains of Sporisorium reilanum f. sp. zeae",Plant and Soil, 236:145-153.
Mwakaboko et al., 2011, "Single step synthesis of strigolactone analogues from cyclic keto enols, germination stimulants for seeds of parasitic weeds", Bioorg. & Med. Chem., 19:5006-5011.
Prandi et al., 2011, "New Potent Fluorescent Analogues of Strigolactones: Synthesis and Biological Activity in Parasitic Weed Germination and Fungal Branching", Eur. J. Org. Chem., 3781-3793.
Reizelman et al., 2000, "Synthesis of All Eight Stereoisomers of the Germination Stimulant Strigol", Synthesis, 1944-1951.
Reizelman et al., 2000, "Synthesis of the Germination Stimulants (+−)-Orobanchol and (+−) Strigol via an Allylic Rearrangement", Synthesis, 13:1952-1955.
Sasaki M., 2009, "Biological activity and synthesis of strigolactones #", J. Pesticide Science Soc. Japan, 34 (4):315-318.
Ueno et al., 2001, "Structural Requirements of Strigolactones for Germination Induction of Striga gesnerioides Seeds", J. Agric. Food Chem., 59: 9226-9231.
Xie et al., 2010, "The Strigolactone Story", Annu. Rev. Phytopathol., 48: 93-117.
Yoneyama et al., 2011, "Characterization of strigolactones exuded by Asteraceae plants", Plant Growth Regul., 65: 495-504.
Yoneyama et al., 2010, "Strigolactones as Germination Stimulants for Root Parasitic Plants", Plant Cell Physiol., 51 (7):1095-1103.
Kohki Akiyama et al., 2010, "Structural Requirements of Stragolactones for Hyphal Branching in AM Fungi", Plant Cell Physiol, 51(7): 1104-1117.
C. B. Pollock et al., 2012, "Strigolactones: a novel class of phytohormones that inhibit the growth and survival of breast cancer cells and breast cancer stem-like enriched mammosphere cells", Breast Cancer Res Treat, 134:1041-1055.
Chinese Office Action, dated Apr. 17, 2015, for The State of Israel, Ministry of Agriculture & Rural Development, Agricultural Research Organization (ARO) (Volcani Center); Geogetown University, Chinese Application No. 201280054089.9.
Supplementary European Search Report, dated Apr. 9, 2015, for The State of Israel, Ministry of Agriculture & Rural Development, Agricultural Research Organization (ARO) (Volcani Center), European Application No. 12 833 721.9.

* cited by examiner

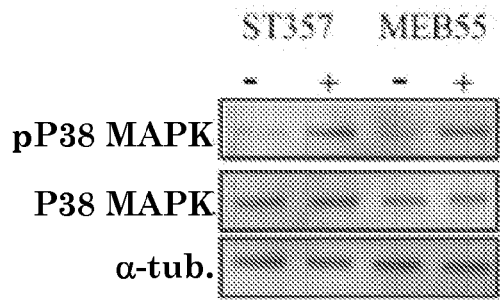
Figure 13J
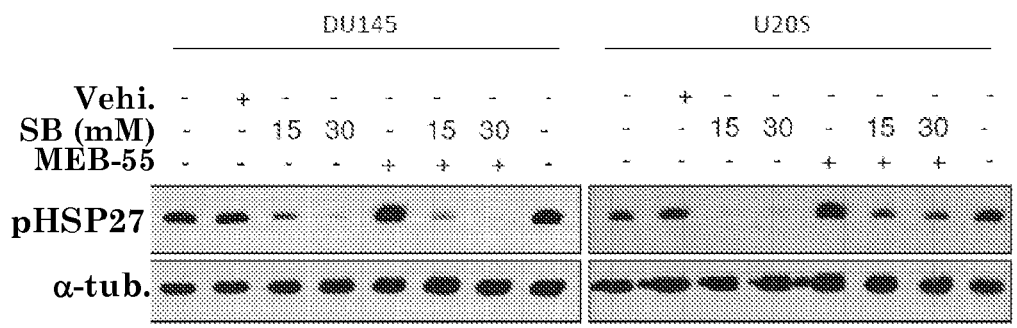
Figure 13K
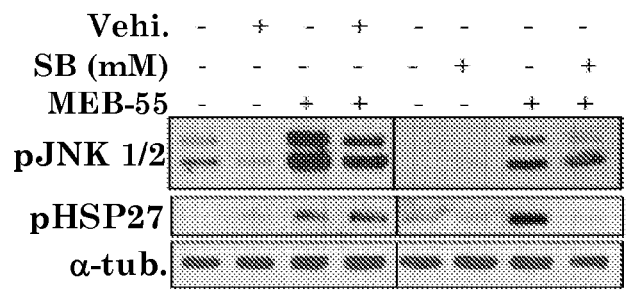
Figure 13L
Figure 13M
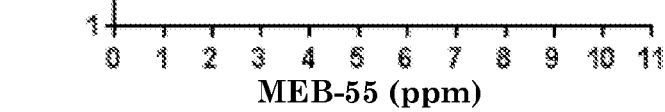

USE OF STRIGOLACTONES AND STRIGOLACTONE ANALOGS FOR TREATING PROLIFERATIVE CONDITIONS

CROSS REFERENCE TO RELATED APPLICATIONS

This application is the National Stage of International Application No. PCT/IL2012/050381, filed Sep. 20, 2012, which claims the benefit of U.S. Ser. No. 61/614,965, filed Mar. 23, 2012, and U.S. Ser. No. 61/537,062, filed Sep. 21, 2011. The entireties of these applications are hereby incorporated by reference into this application.

STATEMENT REGARDING FEDERALLY SPONSORED RESEARCH OR DEVELOPMENT

This invention was made with U.S. government support under grant number W81XWH-11-1-0190 awarded by USAMRAA. The government has certain rights in the invention.

FIELD OF THE INVENTION

The invention relates to the use of strigolactones and/or strigolactones analogs, alone or in any combination with one or more additional pharmaceutically active compounds, as active agents for preventing or inhibiting cell proliferation.

BACKGROUND OF THE INVENTION

All publications mentioned throughout this application are fully incorporated herein by reference, including all references cited therein.

A neoplasmic condition is characterized by an abnormal mass of tissue resulting from neoplasia—an abnormal proliferation of cells. It usually causes a lump or tumor. Neoplasms may be benign, pre-malignant (carcinoma in situ) or malignant (cancer). Human cancer diseases such as breast and lung cancers currently claim the lives of millions annually worldwide. Cancer has recently become the leading cause of deaths in the world. Despite aggressive approaches made in the treatments of breast and lung cancers in the past decades, the 5-year survival rate for, e.g., lung cancer remains <15%. Surgery, chemotherapy, and radiation therapy have been generally unsatisfactory, especially in the treatment of advanced diseases. New drugs based on better understanding of the biology of the disease are thus clearly needed to improve the treatment efficacy of various types of malignant cancer.

Natural compounds derived from plant extracts or derivatives of these compounds have been shown to have activity as anti-cancer agents used as growth inhibitors of human cancer cells such as, e.g., paclitaxel, which is used for the treatment of breast and non-small cell lung cancers.

Paclitaxel was discovered by the US National Cancer Institute in 1967 where researches isolated it from the bark of the Pacific yew tree, *Taxus brevifolia* and named it taxol. The drug was developed commercially by Bristol-Myers Squibb so the generic name was changed to paclitaxel. It has been found in a recent research that paclitaxel acts by inducing Bcl-2 phosphorylation in cancer cells which leads to programmed cell death, as described by Haldar, S. et al., Cancer Res. 56, 1253-1255, 1996. Another example is related to retinoids including natural as well as synthetic derivatives of vitamin A that have been shown to modulate cellular growth as well as differentiation of normal and neoplastic epithelial cells by interacting with nuclear receptors functioning as retinoid-dependent transcriptional factor, as described, e.g., by Amos and Lotan, Methods Enzymol, 190, 217-225, 1990. Retinoic acid most notably is being used to treat some leukemias i.e. PML.

Natural strigolactones of formula I

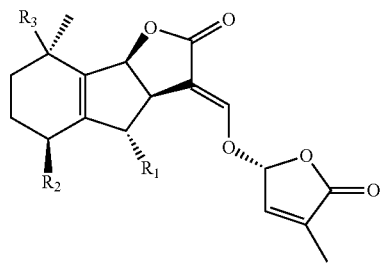

wherein, e.g., $R_1$ is H, OH or OAc, $R_2$ is H, OH or OAc and $R_3$ is H or methyl are a group of plant hormones that have been implicated in inhibition of shoot branching and as signaling molecules for plant interactions, as described by Dun et al., Trends Plant Sci., 14, 364-372, 2009. These naturally occurring chemicals are a group of closely-related molecules synthesized by most plants possibly using carotenoids as the starting material. Strigolactones trigger germination of parasitic plant seeds (for example Striga from which they gained their name) and stimulate symbiotic mycorrhizal fungi hyphal branching.

An analog of the naturally occurring strigolactones is the synthetic plant hormone (3aR*,8bS*,E)-3-(((R*)-4-methyl-5-oxo-2,5-dihydrofuran-2-yloxy)methylene)-3,3a,4,8b-tetrahydro-2H-indeno[1,2-b]furan-2-one (GR-24), which affects cell cycle in root meristem. This compound, which retains the biological activity of the natural strigolactones, has a potential to be used for induction of germination of parasitic seeds before the desired crop is planted.

Programmed cell death in nature is a common feature in the plant kingdom as a response to environmental cues in multicellular organisms. Examples of programmed cell death in plants are, e.g., leaf abscission in the autumn and hypersensitive response during pathogen attack. Reactive oxygen species have been implicated in the regulation of various types of cell death. However, the precise mechanics of the involvement of reactive oxygen species in the processes leading to initiation of cell death and subsequent containment are currently unknown. The involvement of an *Arabidopsis* protein GRIM REAPER in the regulation of reactive oxygen species-induced cell death under stress conditions has been demonstrated.

Anti-proliferative agents possess valuable uses that go beyond the very important use in human and animal health, and find applications in plants, yeasts, fungi, etc.

It is an object of the present invention to provide active agents for preventing or inhibiting cell proliferation in a variety of organisms.

It is another object of the invention to provide medicaments comprising strigolactones and strigolactone analogs, which can be advantageously used in the treatment of a variety of cancer conditions, with reduced side-effects compared to known methods and therapies.

Another object of the invention is to provide compositions and medicaments comprising strigolactones and/or strigolactone analogs, as well as use thereof in the treatment of cancer. Said compositions and medicaments may comprise additional anti-cancerous agents, other active agents, and other additives.

In yet another aspect the invention provides methods of treating cancer by administering strigolactones and/or strigolactone analogs.

In addition, the use of the invention alleviates or eliminates undesired side-effects of known cancer treatment.

The above and other objects and advantages of invention will become apparent as the description proceeds.

SUMMARY OF THE INVENTION

It has now been surprisingly found that natural strigolactones (hereinafter "strigolactones") and substituted strigolactone analogs (hereinafter "strigolactone analogs") can be used as active agents for preventing or inhibiting cell proliferation in many applications, such as human cancer cells, and can be thus used for treating various kinds of cancer such as breast, colon, lung and prostate cancers.

According to one embodiment of the invention, the active agent for preventing or inhibiting cell proliferation is suitable for the treatment of various diseases and conditions, including neoplastic conditions in an animal, including a human, as well as for treating bacterial and fungi infections.

According to a specific embodiment of the invention the medicament is an antineoplastic preparation. According to one embodiment of the invention, the antineoplastic preparation is suitable for the treatment of a condition selected from the group consisting of breast, lung, prostate or colon cancer, and melanoma. Optionally, the antineoplastic preparation further comprises one or more additional active agents.

Thus the present invention relates to the use of a compound of formula X

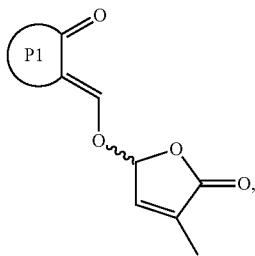

wherein $P_1$ is a fused-ring system comprising one 6-membered and two 5-membered rings; and wherein ∿ indicates an S or R configuration; or individual isomers or pharmaceutically acceptable salts thereof, or mixtures thereof, in the preparation of an active agent for preventing or inhibiting cell proliferation or for inducing cell death.

According to one embodiment of the invention, $P_1$ of the compound of formula X has the following formula

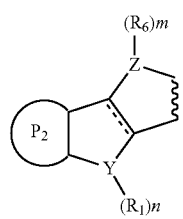

wherein

↓ denotes the attachment point;

the dashed line denotes an optional double bond;

$R_1$ and $R_6$ are independently H, OH, $C_1$-$C_6$alkyl optionally substituted by halogen atoms, $C_2$-$C_6$ alkenyl, $C_2$-$C_6$ alkynyl, cycloalkyl, aryl or heteroaryl optionally substituted by alkyl;

$P_2$ is an optionally substituted 6-membered ring;

Z and Y are independently O, CH or N; and m and n are independently 0 or 1;

with the proviso that if Z is O, m is 0 and if Z is CH or N, m is 1; and with the proviso that if Y is O, n is 0 and if Y is CH or N, n is 1;

or individual isomers or pharmaceutically acceptable salts thereof, or mixtures thereof, in the preparation of an antineoplastic pharmaceutical composition.

According to another embodiment of the invention, $P_2$ of the compound of formula X is selected from the group consisting of:

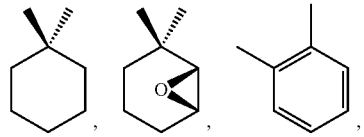

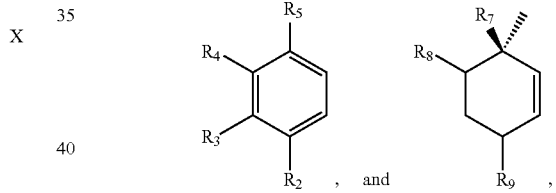

wherein $R_2$ or $R_5$ independently represent H, hydroxy, halogen, lower alkoxy, acyloxy, carboxy, lower alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising 0, 1, 2 or 3 ring nitrogen atoms and 0 or 1 oxygen atom and 0 or 1 sulfur atom, which groups in each case are unsubstituted or mono- or poly-substituted;

$R_3$ or $R_4$ independently represent H, hydroxy, halogen, $C_1$-$C_6$ alkyl, cycloalkyl, benzcycloalkyl, heterocyclyl, an aryl or substituted phenyl, or a mono- or bi-cyclic heteroaryl group comprising 0, 1, 2 or 3 ring nitrogen atoms and 0 or 1 oxygen atom and 0 or 1 sulfur atom, which groups in each case are unsubstituted or mono- or poly-substituted;

$R_7$ is H, OH, $CH_3$, $CH_2OH$ or OAc;

$R_8$ is O or OH, wherein if $R_3$ is O, the bond is a double bond; and $R_9$ is H, OH or OAc.

In a specific embodiment, the compound of formula X is a compound of formula I

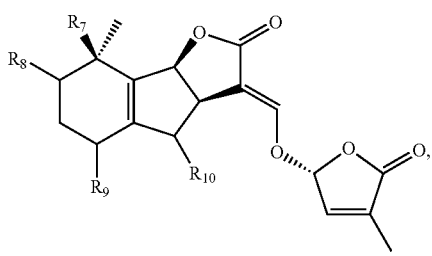

wherein $R_7$, $R_8$, and $R_9$ are as defined above; and $R_{10}$ is H, OH or OAc.

In another specific embodiment of the invention, $P_1$ has the following formula II

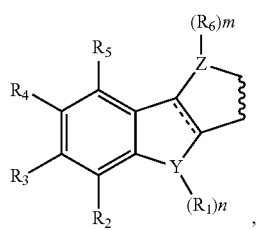

wherein
| denotes the attachment point;
the dashed line denotes an optional double bond;
$R_1$, $R_2$, $R_3$, $R_4$, $R_5$, $R_6$, P, Q, Z, Y, m, and n, are as defined above.

In a specific embodiment, the compound of formula II is selected from
3aR*,8bS*,E)-3-(((R*)-4-methyl-5-oxo-2,5-dihydrofuran-2-yloxy)-methylene)-3,3a,4,8b-tetrahydro-2H-indeno[1,2-b]furan-2-one,
(±)(2E)-4-methyl-2-(4-methyl-5-oxo-2,5-dihydrofuran-2-yloxymethylene)-1,4-dihydro-2H-cyclopenta[b]indol-3-one,
(±)(2E)-7-bromo-4-methyl-2-(4-methyl-5-oxo-2,5-dihydrofuran-2-yloxymethylene)-1,4-dihydro-2H-cyclopenta[b]indol-3-one,
(±)(2E)-4-methyl-2-(4-methyl-5-oxo-2,5-dihydrofuran-2-yloxymethylene)-7-(4-nitrophenyl)-1,4-dihydro-2Hcyclopenta[b]indol-3-one,
(±)(2E)-4-methyl-2-(4-methyl-5-oxo-2,5-dihydrofuran-2-yloxymethylene)-7-(2-thienyl)-1,4-dihydro-2H-cyclopenta[b]indol-3-one,
(±)(2E)-4-methyl-2-(4-methyl-5-oxo-2,5-dihydrofuran-2-yloxymethylene)-7-[(4-dimethylamino)-phenyl]-1,4-dihydro-2H-cyclopenta[b]indol-3-one,
(2E)-7-(1-methoxynaphthalen-2-yl)-1,4-dimethyl-2-((4-methyl-5-oxo-2,5-dihydrofuran-2-yloxy)methylene)-1,2-dihydrocyclopenta[b]indol-3(4H)-one,
(2E)-2-[(2,5-dihydro-4-methyl-5-oxofuran-2-yloxy)methylene]-1,2-dihydro-7-[4-(dimethylamino)phenyl]-1,4-dimethyl-cyclopenta[b]indole-3-(4H)-one,
(2E)-1,4-dimethyl-2-((4-methyl-5-oxo-2,5-dihydrofuran-2-yloxy)methylene)-7-(thiophen-2-yl)-1,2-dihydrocyclopenta[b]indol-3(4H)-one,
(2E)-2-[(2,5-dihydro-4-methyl-5-oxofuran-2-yloxy)methylene]-1,2-dihydro-7-(2,3-dihydrothieno[3,4-b][1,4]dioxin-7-yl)-1,4-dimethylcyclopenta[b]indole-3-(4H)-one,
(±)2E-4-methyl-2-(4-methyl-5-oxo-2,5-dihydrofuran-2-yloxymethylene)-6-thiophen-2-yl-1,4-dihydro-2H-cyclopenta[b]indol-3-one,
(3aR*,8bS*,E)-3-(((R*)-4-methyl-5-oxo-2,5-dihydrofuran-2-yloxy)methylene)-3,3a,4,8b-tetrahydro-2H-indeno[1,2-b]furan-2-one,
(±)(2E)-4-methyl-2-(4-methyl-5-oxo-2,5-dihydrofuran-2-yloxymethylene)-1,4-dihydro-2Hcyclopenta[b]indol-3-one,
(±)(2E)-4-methyl-2-(4-methyl-5-oxo-2,5-dihydrofuran-2-yloxymethylene)-7-[(4-dimethylamino)-phenyl]-1,4-dihydro-2H-cyclopenta[b]indol-3-one,
(2E)-1,4-dimethyl-24(4-methyl-5-oxo-2,5-dihydrofuran-2-yloxy)methylene)-7-(thiophen-2-yl)-1,2-dihydrocyclopenta[b]indol-3(4H)-one,
(2E)-2-[(2,5-dihydro-4-methyl-5-oxofuran-2-yloxy)methylene]-1,2-dihydro-7-(2,3-dihydrothieno[3,4-b][1,4]dioxin-7-yl)-1,4-dimethyl-cyclopenta[b]indole-3-(4H)-one, and
(±)2E-4-methyl-2-(4-methyl-5-oxo-2,5-dihydrofuran-2-yloxymethylene)-6-thiophen-2-yl-1,4-dihydro-2Hcyclopenta[b]indol-3-one, and
combinations thereof.

In another aspect the invention relates to an anti-proliferative composition comprising the compound of formula X, or individual isomers or pharmaceutically acceptable salts thereof, or mixtures thereof. Said composition is suitable for killing cancer stem cells (CSCs) or tumor initiating cells (TICs), and is suitable for topical, enteral, oral, rectal, or parenteral administration. Said composition is further suitable for preventing or inhibiting the growth of, or destroying, yeasts and fungi.

The invention further encompasses a method of treating a proliferative condition comprising administering to a patient in need thereof a compound of formula X, or isomers or pharmaceutically acceptable salts thereof, or mixtures thereof. Said method, can involve the administration of the compound of formula X prior, after or in conjunction with at least one other cancer therapy.

In a specific embodiment of the invention, the compound of formula I is selected from

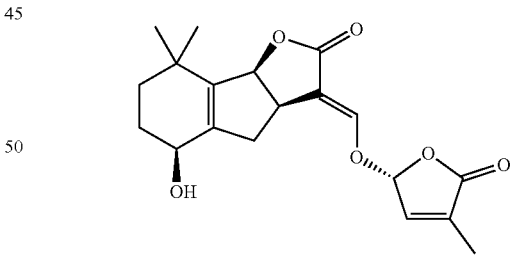

Strigol

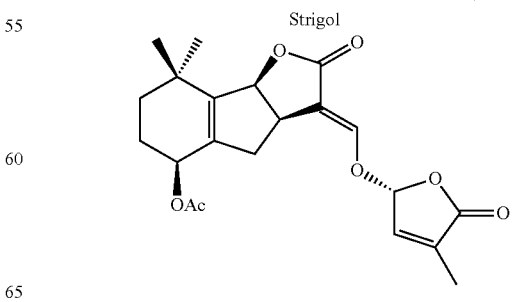

Strigyl acetate

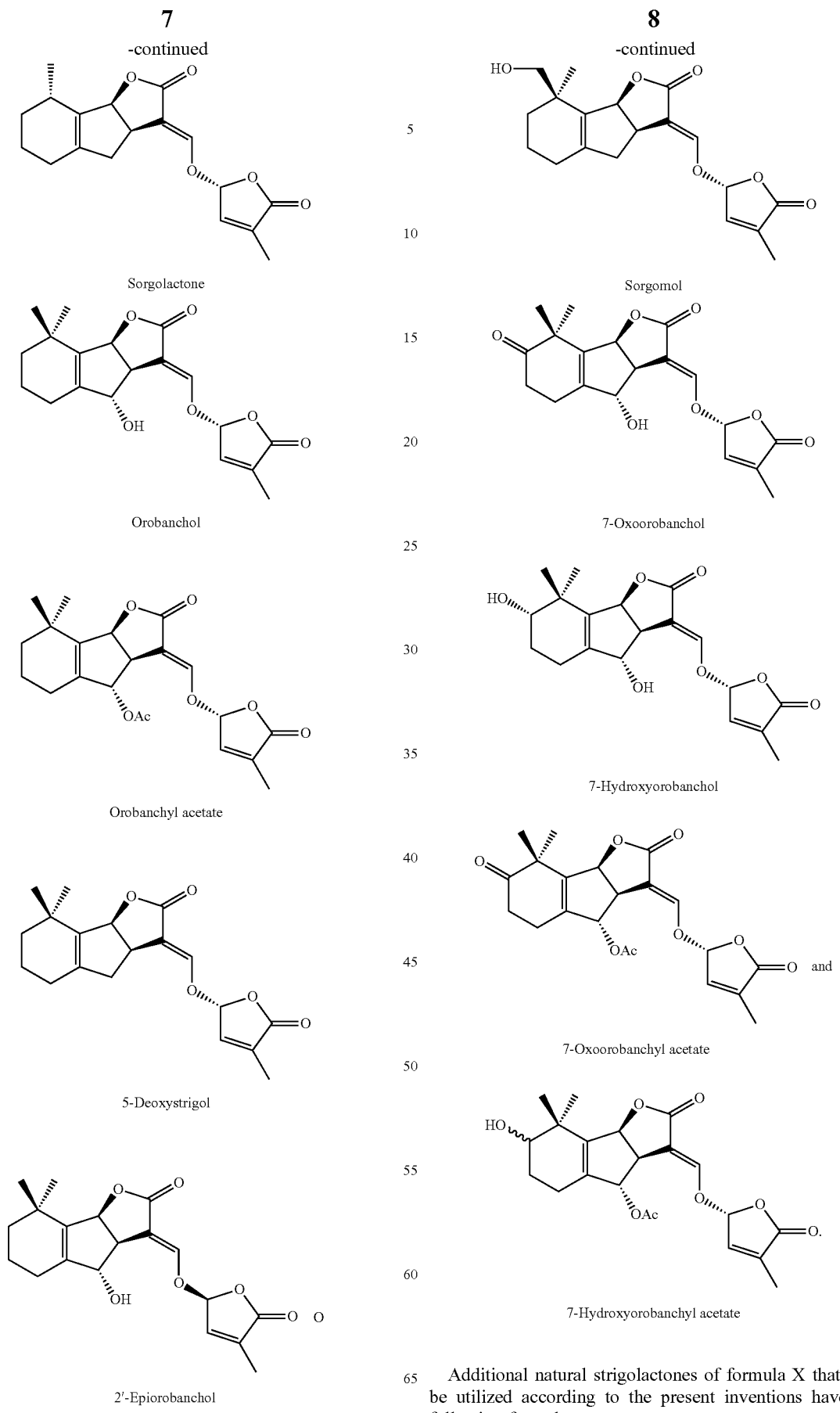
Additional natural strigolactones of formula X that may be utilized according to the present inventions have the following formulas:

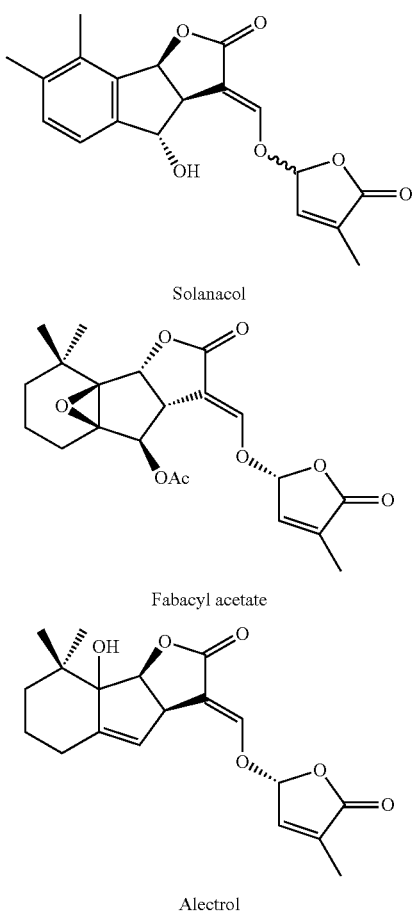

Solanacol

Fabacyl acetate

Alectrol

The present invention further relates to a compound of formula X

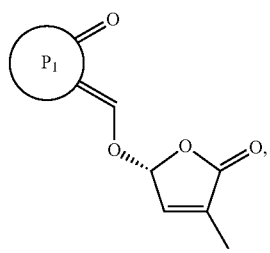

X as defined above, for use as an anti-proliferative agent.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The above and other characteristics and advantages of the invention will be more readily apparent through the following examples, and with reference to the appended drawings, wherein.

Abbreviations: Abs. (Absorbance), cont. (control), T. (time), d. (days), Fib. (Fibroblasts).

Figure 4:
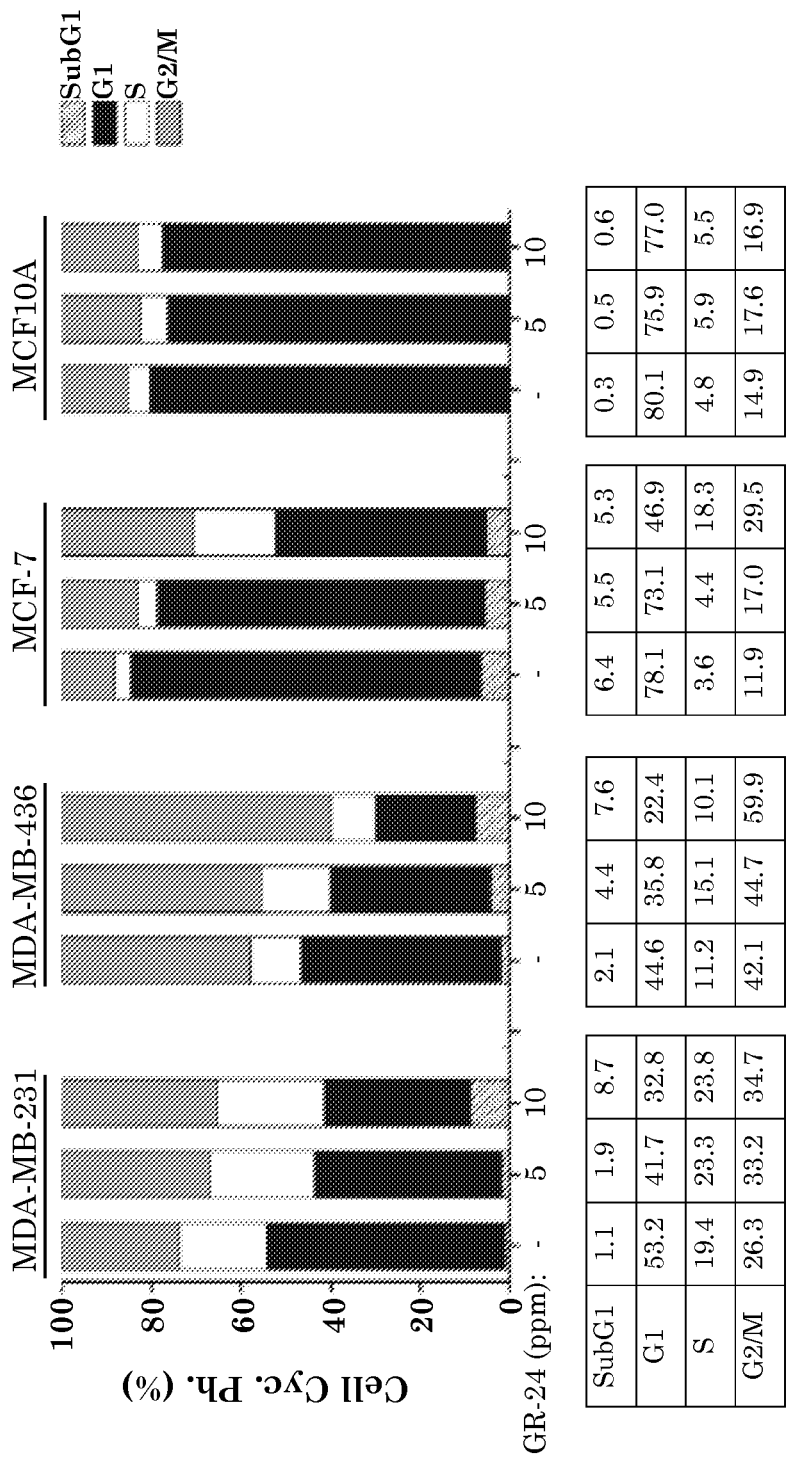

FIG. 4. depicts the effect of GR-24 on cell cycle progression. Data is representative of two independent experiments.

Abbreviations: Cell Cyc. Ph. (Cell Cycle Phases).

FIG. 5. depicts mammosphere formation in the presence of GR-24. The images are representative bright field images of either primary mammospheres (A) or secondary mammospheres (B) or MDA-MB-231 primary mammospheres (C) grown in the presence of GR-24, vehicle control or untreated (−) (Magnification: 10× (A, B), 20× (C)), scale bar 100 uM. The corresponding Bar graphs show the average number of mammospheres (over 100 uM diameter) per well of 96 well plate, visualized at 5× magnification. Data reported as average±standard deviations (SD) of triplicate wells and representative of at least two independent experiments. Student's t-test (2-tailed, paired) was used to evaluate GR-24 treated groups with vehicle (control) group and regarded as being significant if p<0.05 (*), very significant if p<0.01 (), extremely significant if p<0.001 (*)

Abbreviations: cont. (control), conc. (concentration), Pri. Mam. (Primary Mammosphere), Sec. Mam. (Secondary Mammosphere).

FIG. 6. shows viability and ALDH expression following GR-24 treatment: (A) XTT viability assay on MCF-7 secondary mammospheres treated with GR-24. Data reported as % of vehicle control. Bars, Average±standard deviations (SD) of triplicate samples. Student's t-test (2-tailed, paired) was used to evaluate 5 ppm treated group with control group, p=0.0065 (**). (B) analysis of ALDH1 expression in primary MCF-7 mammospheres.

Abbreviations: Viab. (viability), cont. (control), conc. (concentration), Ad. (adherent), Sec. Mam. (Secondary Mammosphere), Pri. (Primary), exp. (expression).

Figure 7A:
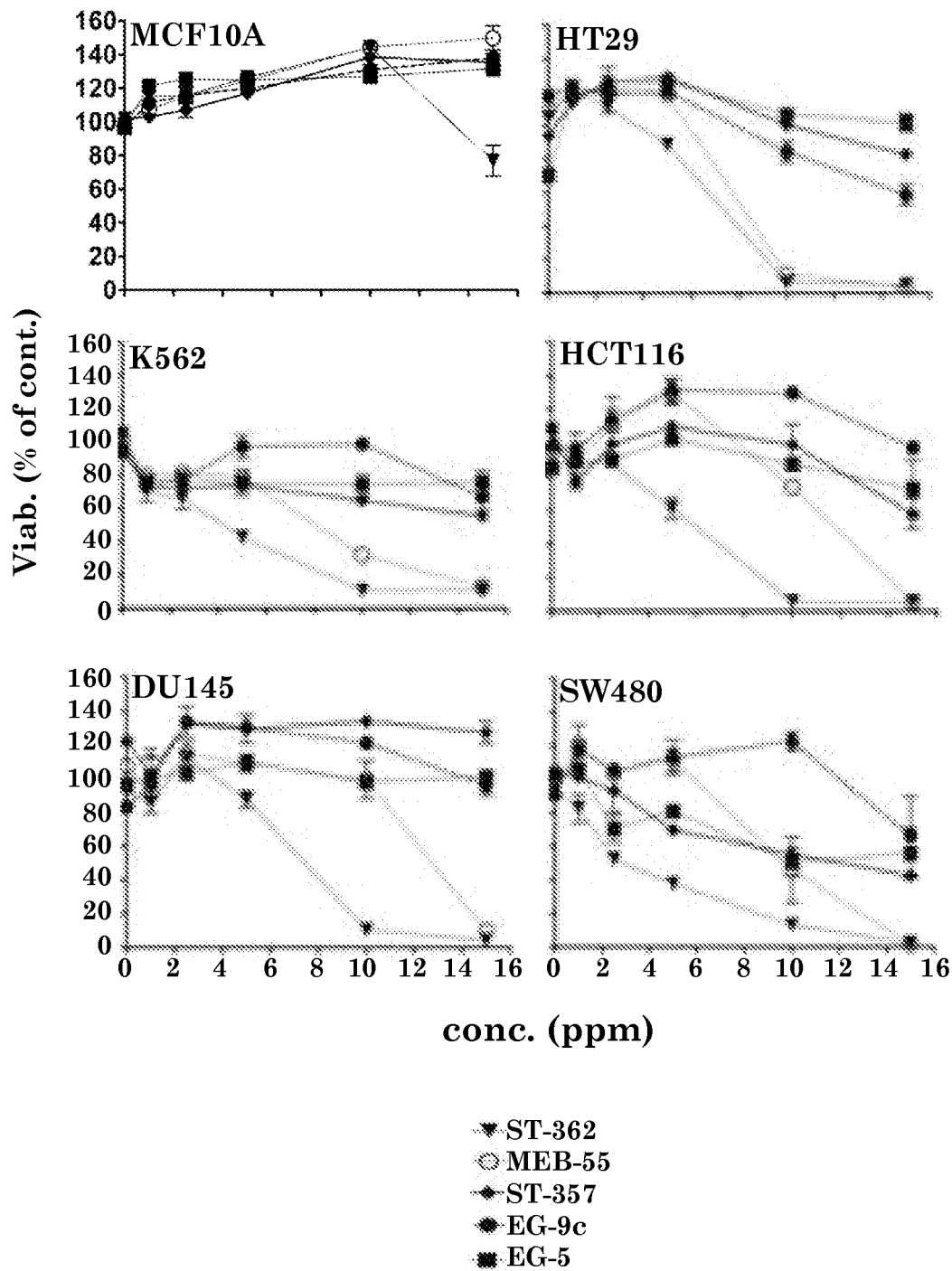
Figure 7B:
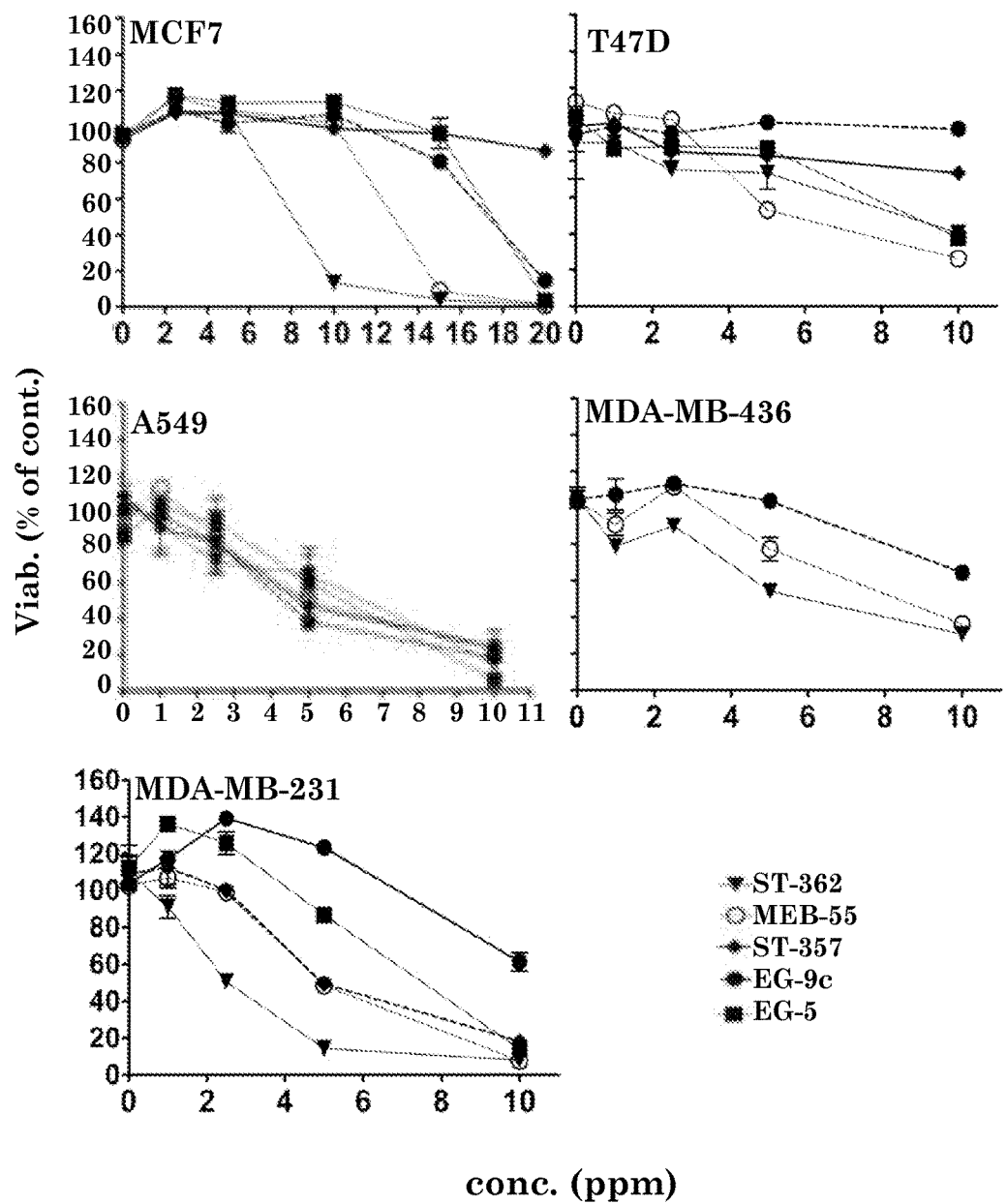
Figure 7C:
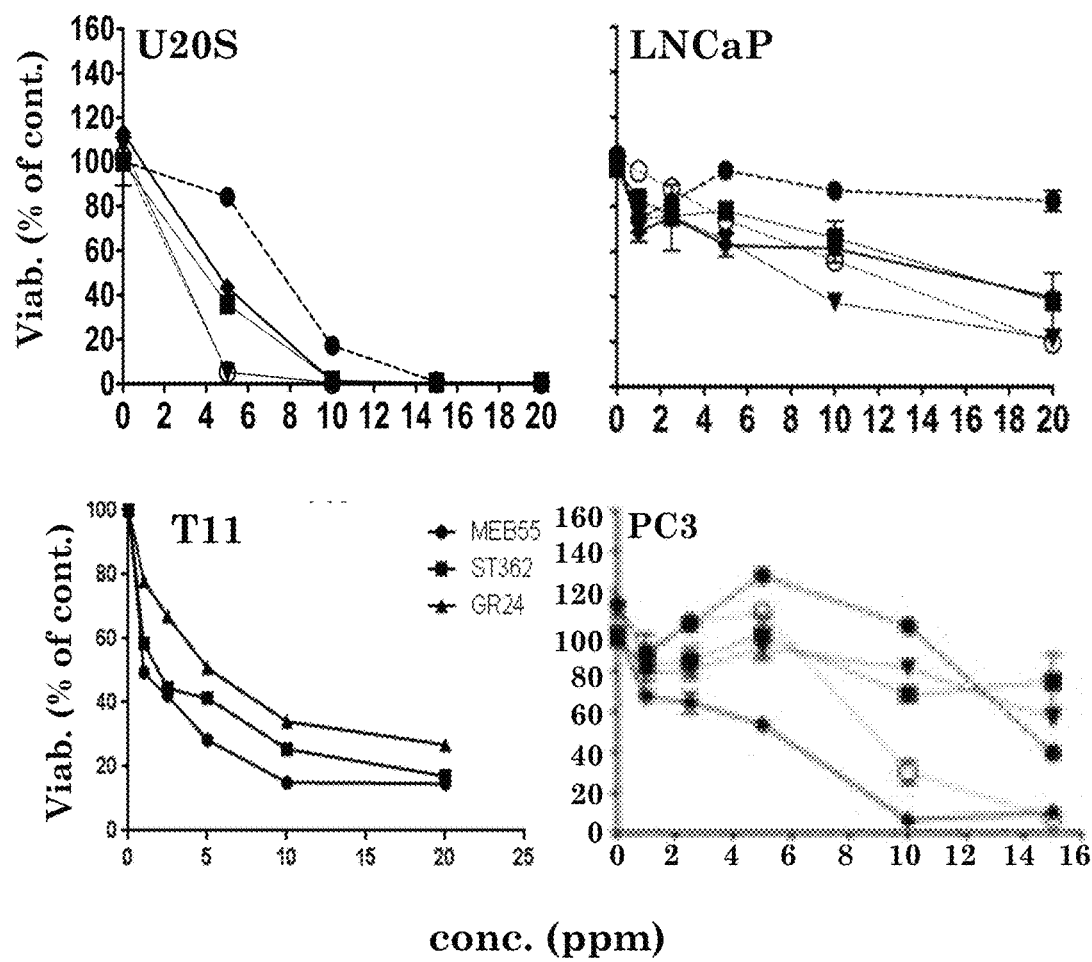

FIG. 7. (A)-(C) depicts the effect of strigolactone analogs on human cancer cell lines growth and viability. Graphs are representative of two independent experiments with duplicate replicate wells for each analysis.

Abbreviations: Viab. (viability), cont. (control), conc. (concentration).

Figure 8:
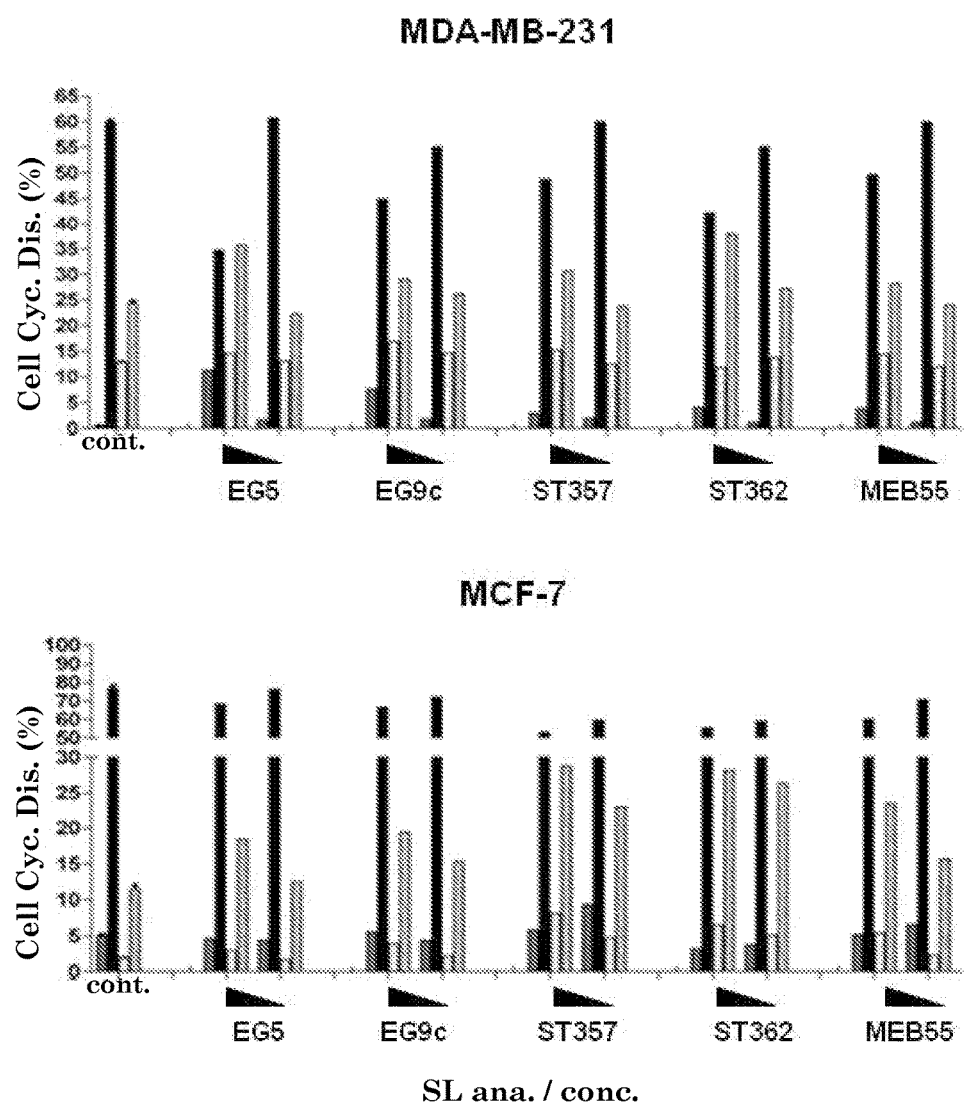

FIG. 8. depicts cell cycle analysis of cancer cell lines treated with strigolactone analogs.

Abbreviations: Cell Cyc. Dis. (Cell Cycle Distribution), SL Ana. (strigolactone analogs).

FIG. 9. shows that strigolactone analogs induce apoptosis in MDA-MB-231 cells: (A) Hoechst33342 staining of MDA-MB-231 cells treated with the strigolactone analog ST-362 (Magnification 200×. Scale bar, 50 uM). (B)-(E) XTT viability assay following strigolactone exposure. Data are reported as % of vehicle control groups. Bars represent Average±SD. Statistical analysis, student's t-test (2-tailed, paired) versus vehicle controls and regarded as being significant if p<0.05 (*), p<0.01 (), p<0.001 (*).

Abbreviations: Vehi. (Vehicle), Viab. (Viability), cont. (control), conc. (concentration). SL. Rel T. (strigolactone release time), hr. (hour).

Figure 10A:
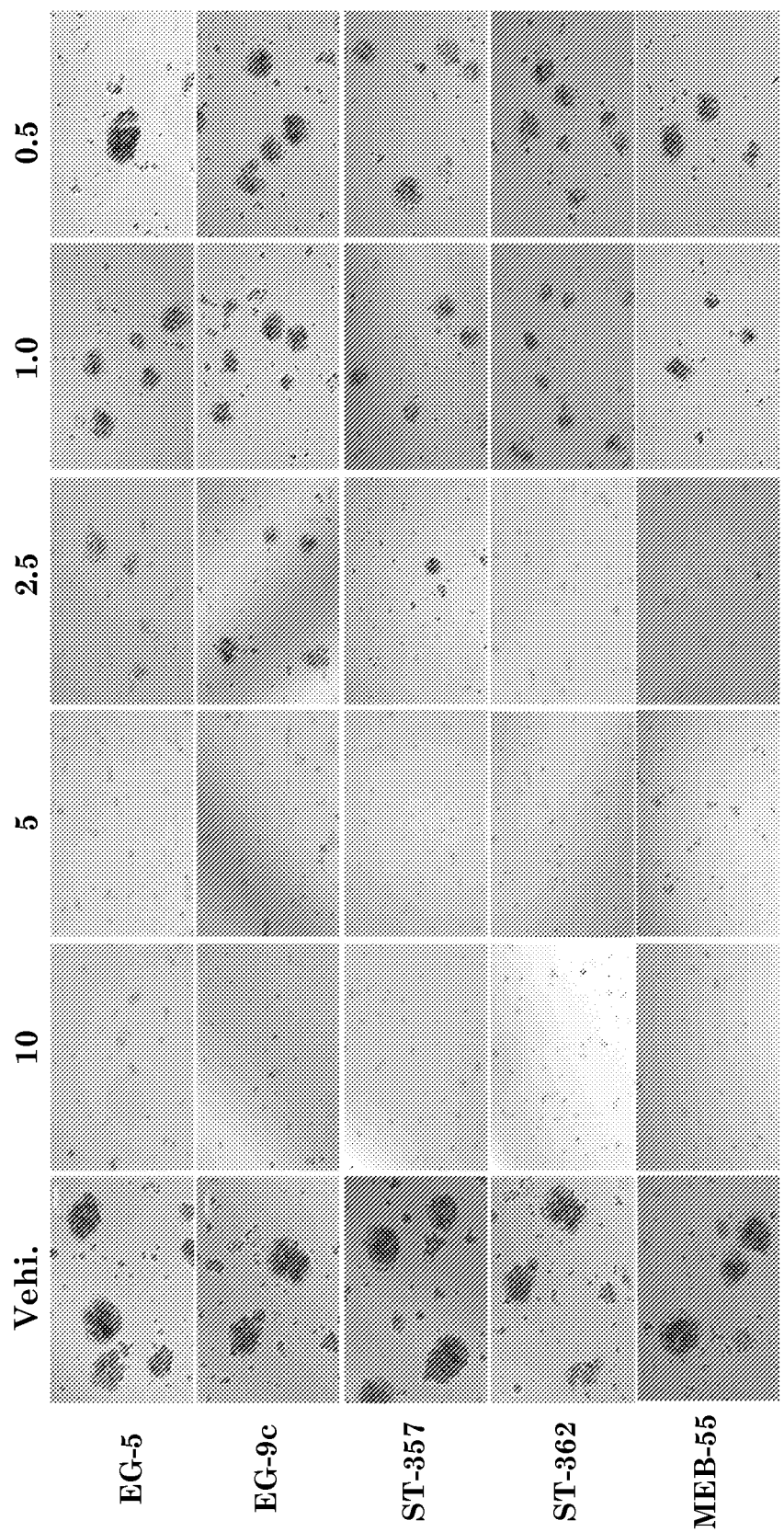
Figure 10B:
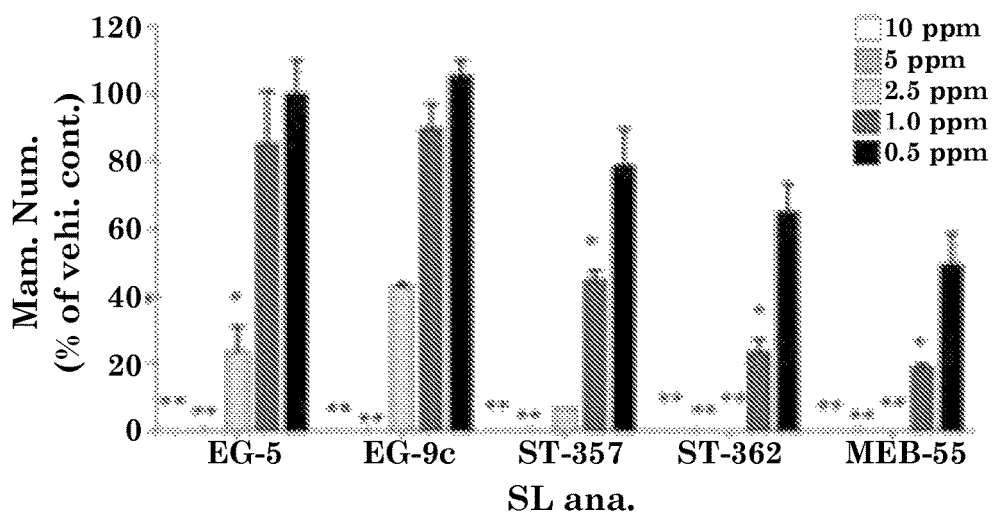
Figure 10C:
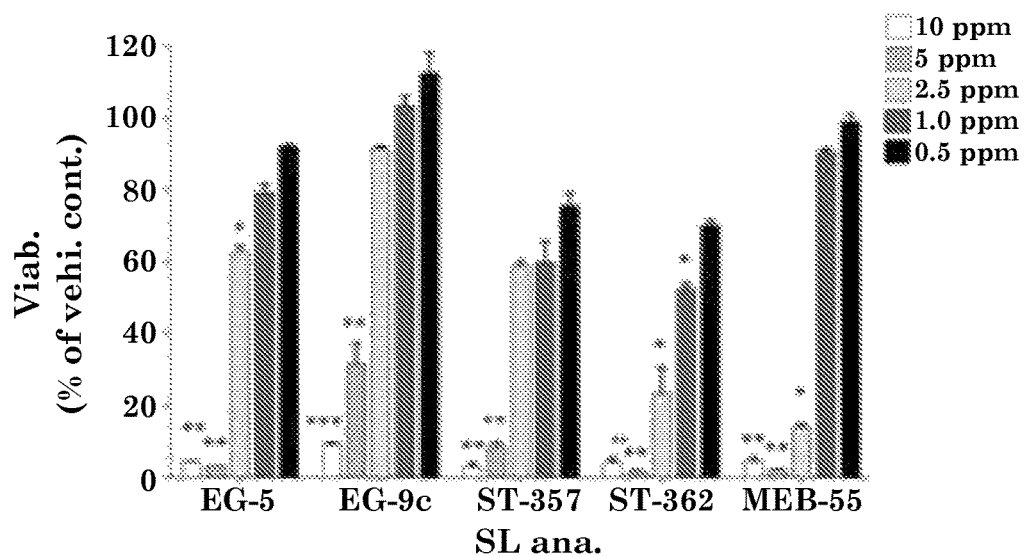

FIG. 10. shows the effect of strigolactone analogs on MCF-7 mammosphere formation: (A) count of mammospheres numbers over 100 uM diameter. (B) assess of XTT viability. (C) statistical analysis of mammosphere number following strigolactone analogs by two tail student t-test p≤0.05 (*), p≤0.005 (), p≤0.001 (*).

Abbreviations: Vehi. (Vehicle), Mam. Num. (Mammosphere Number), cont. (control), SL ana. (strigolactone analog), Viab. (Viability).

Figure 11A:
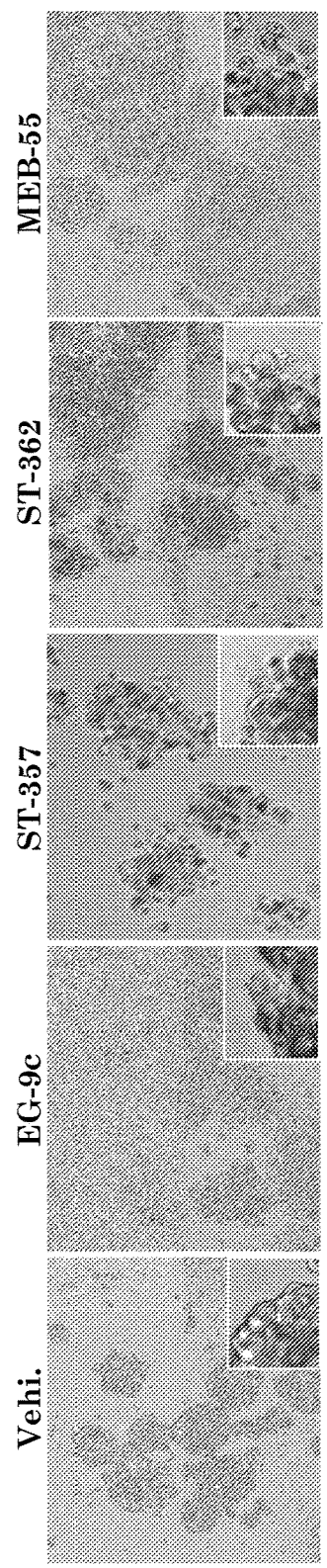
Figure 11B:
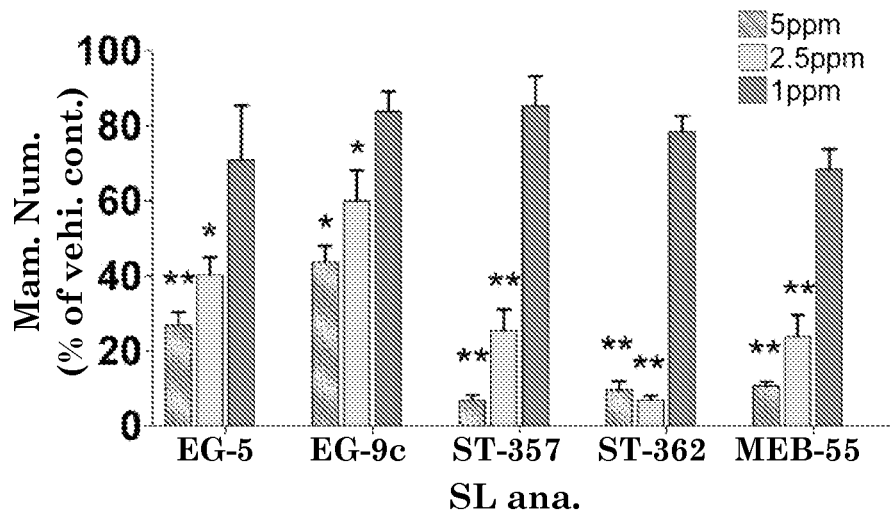
Figure 11C:
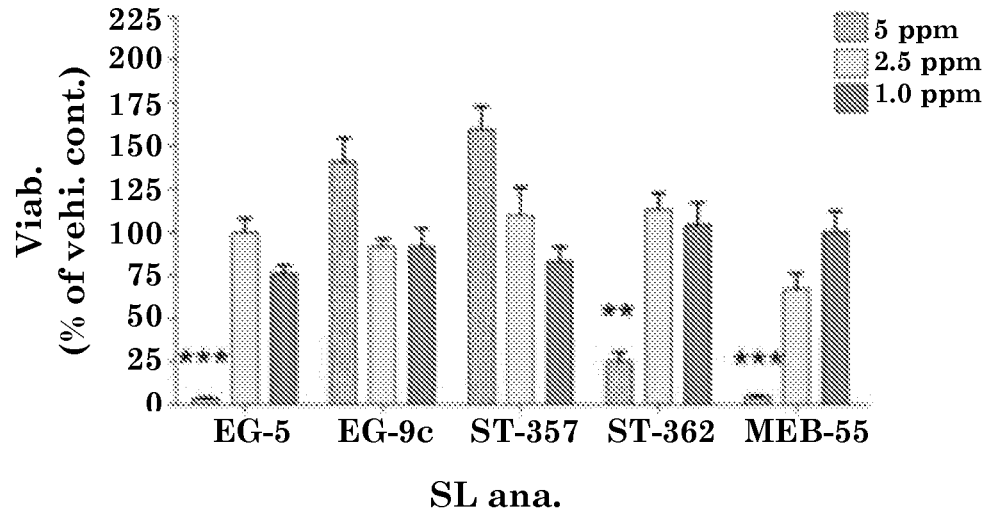

FIG. 11. depicts the effect of strigolactone analogs on primary MCF-7 mammosphere integrity and viability: (A) representative images of mammospheres after 2 days of strigolactone treatment (Magnification 100×, Scale bar, 100 uM. Insert, zoomed image). (B)-(C) statistical analysis of mammospheres numbers and viability following 5 days of strigolactone treatment.

Statistical Analysis, two tailed students t-test, p<0.05 (*), p<0.01 (), p<0.001 (*).

Abbreviations: Vehi. (Vehicle), Mam. Num. (Mammosphere Number), cont. (control), SL ana. (strigolactone analog), Viab. (Viability).

FIG. 12. shows that strigolactone analogs treatment causes G2 arrest and induces apoptosis of various cancer cell lines (A)-(C). (D)+(G) Bar graph showing the distribution of HCT116 cells in early (Annexin−/PI+, gray bars) and late (Annexin+/PI+, black bars) apoptosis following strigolactone analogs treatment. (E) Representative FACS analysis of phospho-Ser10 Histone-H3 (vertical) versus DNA content (horizontal) of HCT116 cells treated with either ST-357 (middle panels) or MEB-55 (lower panels) at the indicated doses. (F) FACS analysis (Annexin V staining) of HCT116 cells treated with strigolactone analog.

Abbreviations: Cell Cyc. Dis. (Cell Cycle Distribution), Apo. (apoptosis), Vehi. (vehicle).

FIG. 13. is an immunoblot analysis of MDA-MB-231 and HCT116 cells (A)-(F) or DU145 cells (G)-(L) showing that strigolactone analogs induce stress response: (A) immunoblot analysis of cells following treatment with ST-362 or vehicle alone (−). (B) Bar graph showing densitometric quantification of pP38 levels as shown in (A). (C) immunoblot analysis of HSP27 phosphorylation in cells treated with vehicle or ST-362 (10 ppm). (D) immunoblot analysis of protein expression levels following treating MDA-MB-231 cells with MEB-55 (10 ppm) or vehicle, for 4 hours. (E) immunoblot analysis of cells treated with ST-362 alone or together with SB. (F) immunoblot analysis of cells treated with MEB-55 alone or with SB. (G) immunoblot analysis of cells following treatment with MEB-55 or vehicle alone. (H) Bar graph showing densitometric quantification of various phosphorylated proteins as shown in (G). (I) immunoblot analysis of P38, JNK and ERK phosphorylation in cells treated with vehicle or MEB-55. (J) immunoblot analysis of pP38 following treating with ST-37 or MEB-55. (K) immunoblot analysis of pHSP27 following treating with MEB-55 alone or together with SB. (L) immunoblot analysis of pJNK and pHSP27 in cells treated with MEB-55 alone or together with SB. (M) graph showing survival of cells treated with MEB-55 alone or with SB.

Abbreviations: α-tub. (α-tubulin), Fol. Chan. (Fold change), Vehi. (Vehicle), Ac. (Acetone), SB (SB203580), hr (hour), Sur. (survival).

Figure 14:
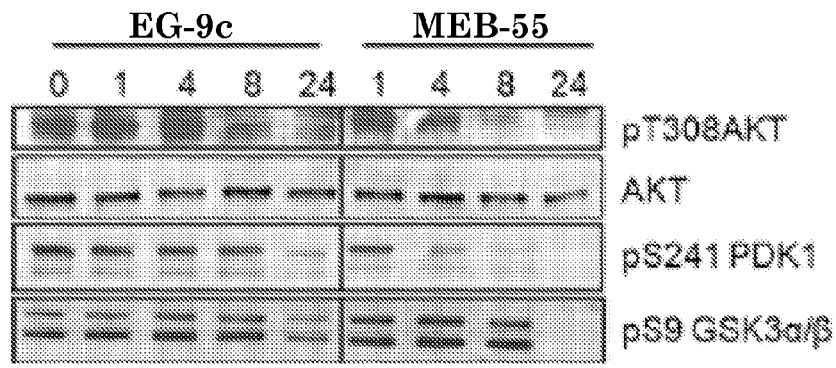

FIG. 14. is an immunoblot analysis of MDA-MB-231 cells treated with vehicle alone or with 10 ppm of EG-5 or MEB-55, showing that strigolactone analogs inhibit survival signaling.

Figure 15:
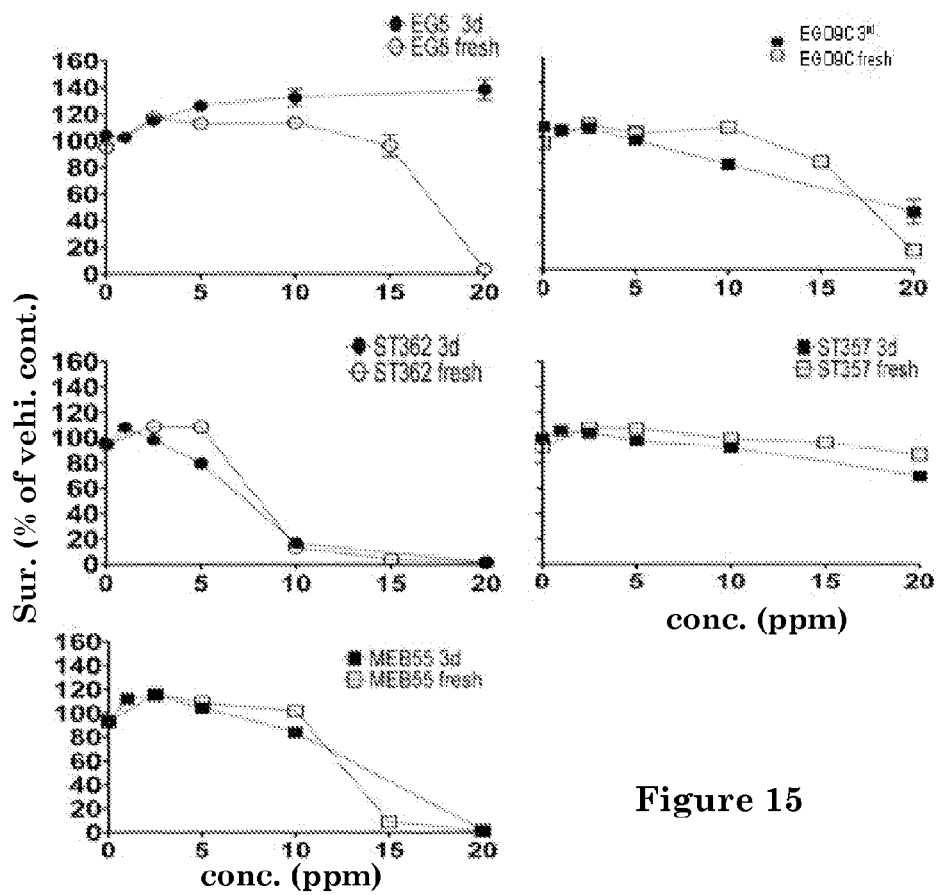

FIG. 15. shows stability of strigolactone analogs.

Abbreviations: Sur. (survival), Vehi. (Vehicle), cont. (control), conc. (concentration), fr. (fresh).

Figure 16:
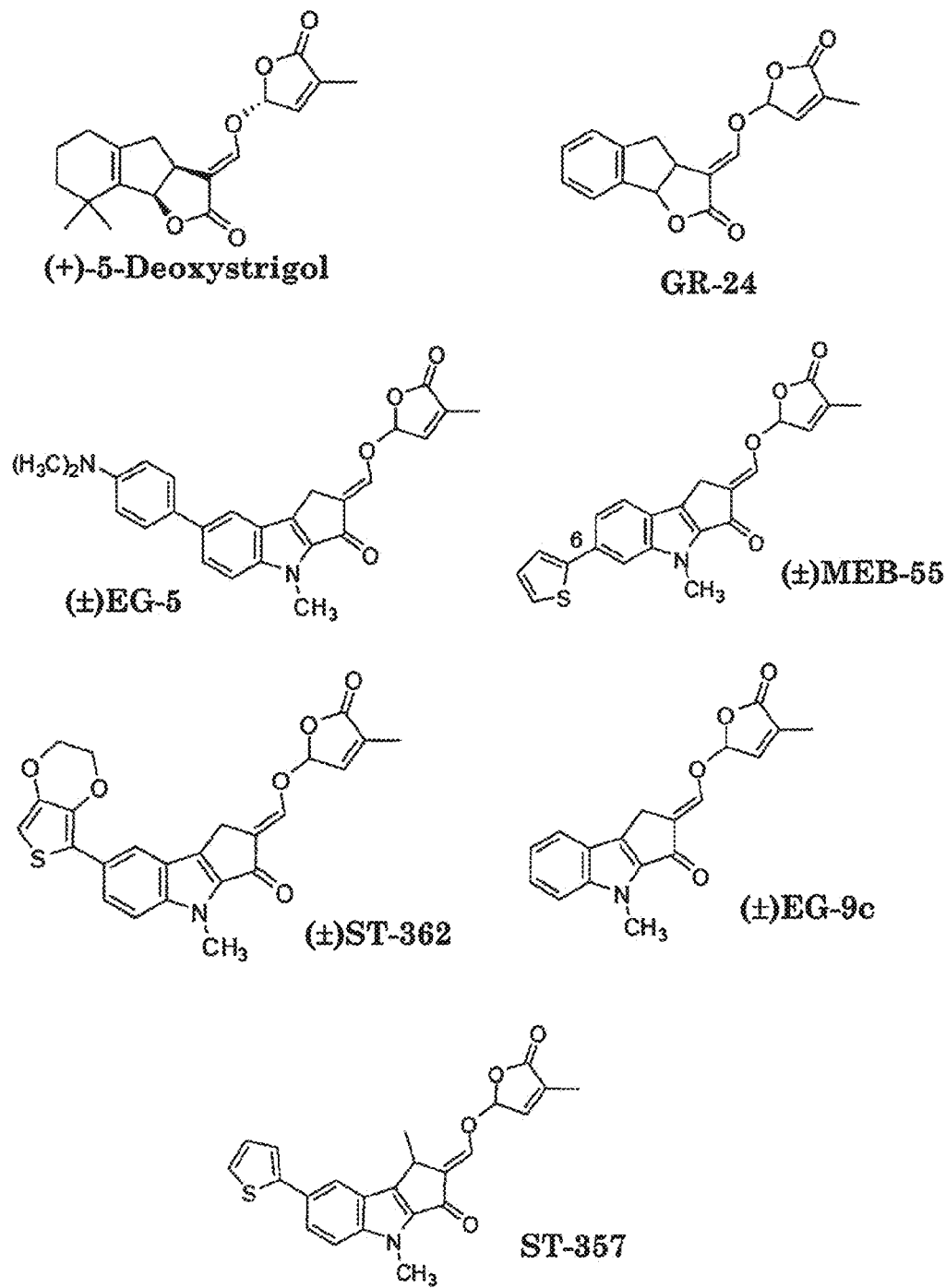

FIG. 16. is a schematic illustration of basic strigolactone, 5-Deoxystrigol, and the strigolactone analogs GR-24, EG-5, EG-9C, ST-357, ST-362 and MEB-55.

FIG. 17. shows that colon (A) or prostate (B)-(H) cells undergo G2/M arrest and apoptosis in response to strigolactone treatments: (A) immunoblot of cyclin B in HCT116 cells treated with strigolactone analog. (B) immunoblot of DU145 cells treated with MEB-5. (C) immunoblot of HCT116 cells treated with ST-362 or MEB-5. (D) immunoblot of U20S cells treated with MEB-5. (E) Quantitative RealTime PCR analysis of Cyclin B1 mRNA relative to GAPDH in A549 or HCT116 cells treated with MEB-55. (F) immunoblot of DU145 cells treated with ST-362 or MEB-55. (G) the effect of MEB-55 on cell cycle progression. (H) immunoblot of DU145 cells treated with ST-362 or MEB-55, in the presence of the proteosome inhibitor, ALLN.

Abbreviations: tub. (tubulin), Vehi. (Vehicle), cont. (control), Prop. Iod. (Propidium Iodide), hr (hour), Cell Cyc. Ph. (Cell Cycle Phases).

Figure 18:
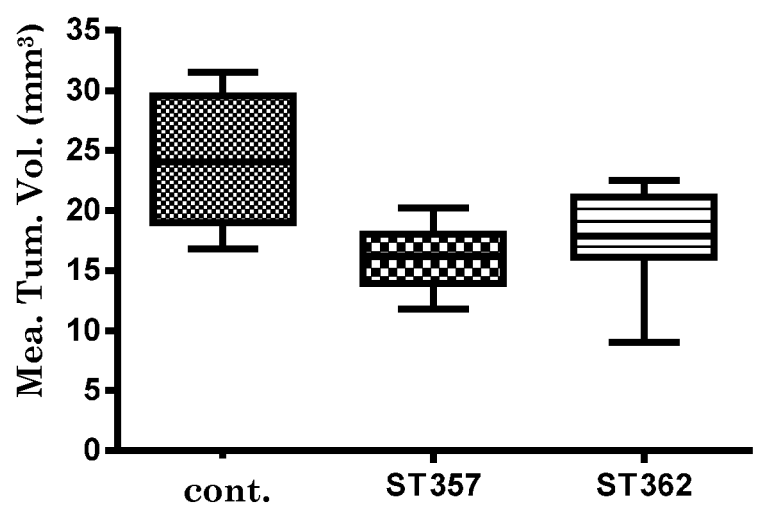

FIG. 18. is a graph showing the mean tumor volume of tumors in mice treated with ST-357 or ST-362.

Abbreviations: Mea. Tum. Vol. (mean tumor volume), cont. (control).

Figure 19:
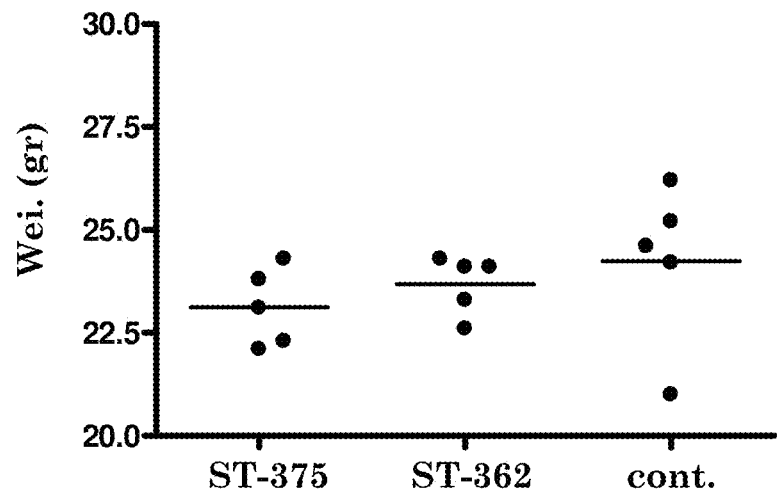

FIG. 19. is a graph showing that strigolactone analogs treatment does not effect body weight.

Abbreviations: Wei. (weight), gr (gram), cont. (control).

Figure 20:
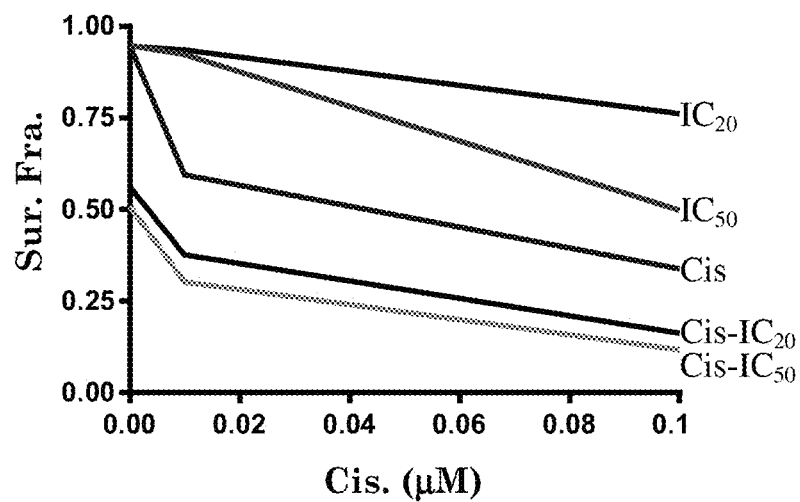

FIG. 20. is a graph showing the synergistic effect of a combined treatment of cisplatin and strigolactone analogs.

Abbreviations: Sur. Fra. (surviving fraction), cis. (cisplatin).

Figure 21:
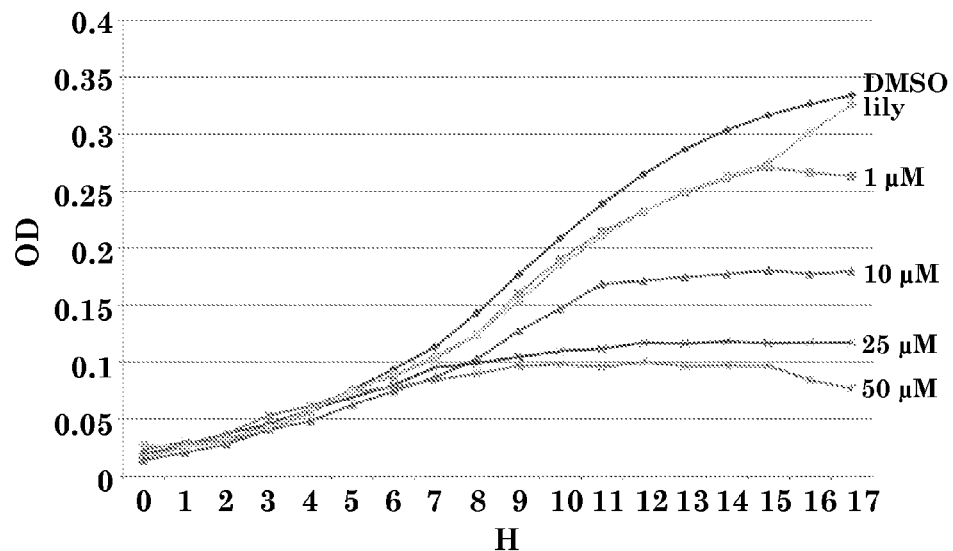

FIG. 21. is a graph showing the effect of GR-24 on *Saccharomyces cerevisiae* yeast culture growth over time.

Abbreviations: lily (culture growth media only), DMSO (solvent only), H (hours), OD (optical density), GR-24 μM concentrations are shown.

Figure 22:
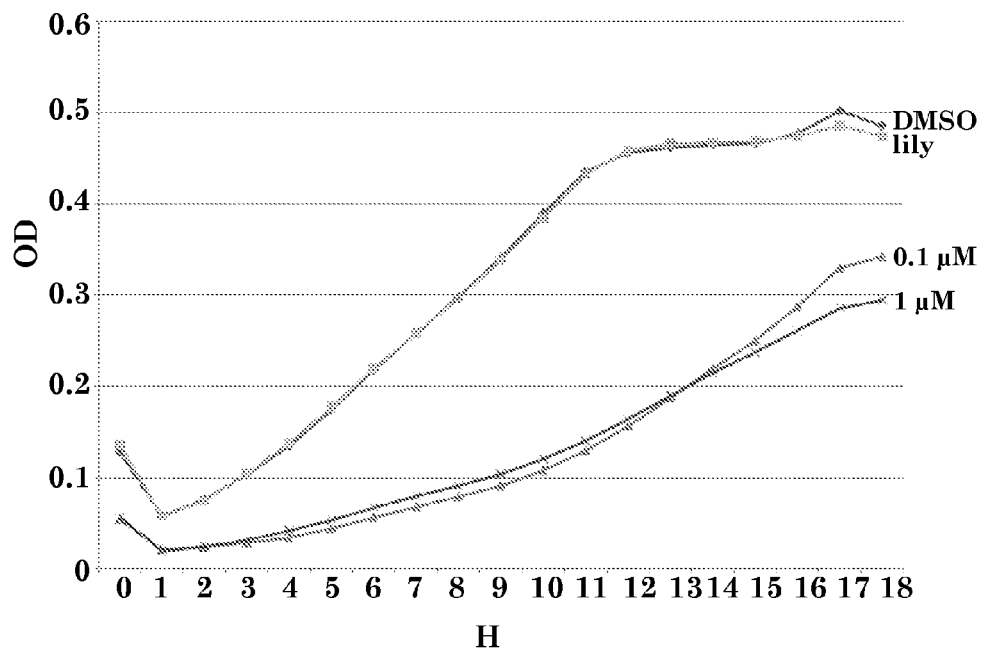

FIG. 22. is a graph showing the effect of ST-362 on *Saccharomyces cerevisiae* yeast culture growth.

Abbreviations: lily (culture growth media only), DMSO (solvent only), H (hours), OD (optical density), ST-362 μM concentrations are shown.

Figure 23:
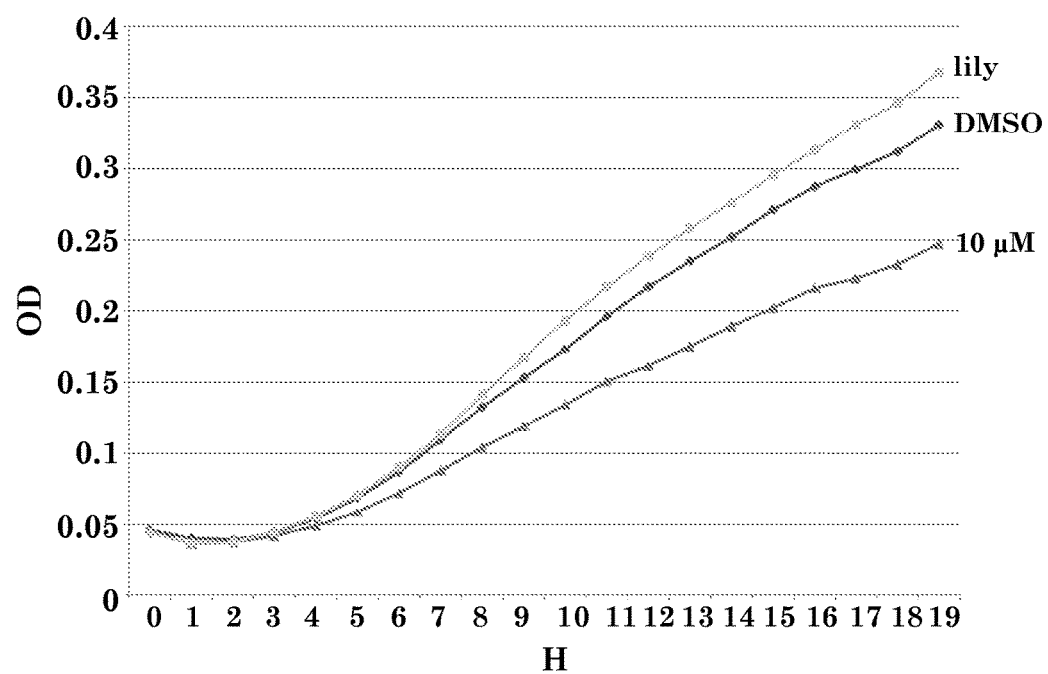

FIG. 23. is a graph showing the effect of ST-362 on *Candida oleophila* yeast culture growth.

Abbreviations: lily (culture growth media only), DMSO (solvent only), H (hours), OD (optical density), ST-362 μM concentration is shown.

DETAILED DESCRIPTION OF THE INVENTION

The examples to follow illustrate the effect of natural strigolactones (referred to herein as "strigolactones"), strigolactone analogs and substituents thereof (referred to herein as "strigolactone analogs"), as anti-proliferative agents in a variety of mammal and non-mammal systems, as well as their efficacy as growth inhibitors of human cancer cells, and their usefulness in treating various kinds of cancers, such as breast, colon, lung, and/or prostate cancers, or melanoma.

The compounds of formula X described herein show specific and marked inhibition of cancer cell growth, as well as induction of programmed death of tumor cells, and are useful in the treatment of cancer diseases.

In the description and examples to follow reference is made to compounds of formula II, referred to herein as "strigolactone analogs" and to isomers thereof (the atoms numbers are marked according to the IUPAC systematic numbering).

At least one asymmetric carbon atom may be present in the (R)-, (S)- or (R,S)-configuration, preferably in the (R)- or (S)-configuration of the compounds of formula II. The compounds of formula II may thus be present as mixtures of diastereoisomers or as racemic mixture or as pure isomers, optionally as enantio-pure isomers, that is, individual isomers or mixture of isomers thereof.

Table 1 below lists examples of strigolactone analogs of the present invention mentioning their chemical names and given codes.

group P is in position 2, group Q must be in position 3 and vice versa if group P is in position 3, group Q must be in position 2.

The term "apoptosis" refers herein to the process of programmed cell death that occurs in multicellular organisms.

The terms "MCF-7", "MDA-MB-436" "MDA-231", "T47D" and the like refer herein to different types of breast cancer cell lines.

The term "mammosphere" refers herein to a clump of mammary gland cells that forms under certain circumstances. Mammosphere culture has been used for the enrichment of breast Cancer Stem Cells (hereinafter CSCs). MCF-7 and MDA-231 cells can be propagated as 'mammospheres' under non-adherent, serum-free growing conditions.

The term "cyclin B1" (hereinafter CYCB1) refers to the regulatory subunit of M-phase promoting factor, which is

TABLE 1

| No | Chemical Name | Code |
|---|---|---|
| 1 | 3aR*,8bS*,E)-3-(((R*)-4-methyl-5-oxo-2,5-dihydrofuran-2-yloxy)-methylene)-3,3a,4,8b-tetrahydro-2H-indeno[1,2-b]furan-2-one | GR-24 |
| 2 | (±) (2E)-4-methyl-2-(4-methyl-5-oxo-2,5-dihydrofuran-2-yloxymethylene)-1,4-dihydro-2H-cyclopenta[b]indol-3-one | EG-5 |
| 3 | (±) (2E)-7-bromo-4-methyl-2-(4-methyl-5-oxo-2,5-dihydrofuran-2-yloxymethylene)-1,4-dihydro-2H-cyclopenta[b]indol-3-one | EG-7 |
| 4 | (±) (2E)-4-methyl-2-(4-methyl-5-oxo-2,5-dihydrofuran-2-yloxymethylene)-7-(4-nitrophenyl)-1,4-dihydro-2H-cyclopenta[b]indol-3-one | EG-9a |
| 5 | (±) (2E)-4-methyl-2-(4-methyl-5-oxo-2,5-dihydrofuran-2-yloxymethylene)-7-(2-thienyl)-1,4-dihydro-2H-cyclopenta[b]indol-3-one | EG-9b |
| 6 | (±) (2E)-4-methyl-2-(4-methyl-5-oxo-2,5-dihydrofuran-2-yloxymethylene)-7-[(4-dimethylamino)-phenyl]-1,4-dihydro-2H-cyclopenta[b]indol-3-one | EG-9c |
| 7 | (2E)-7-(1-methoxynaphthalen-2-yl)-1,4-dimethyl-2-((4-methyl-5-oxo-2,5-dihydrofuran-2-yloxy)methylene)-1,2-dihydrocyclopenta[b]indol-3(4H)-one | ST-23a |
| 8 | (2E)-2-[(2,5-dihydro-4-methyl-5-oxofuran-2-yloxy)methylene]-1,2-dihydro-7-[4-(dimethylamino)pheny]-1,4-dimethyl-cyclopenta[b]indole-3-(4H)-one | ST-23b |
| 9 | (2E)-1,4-dimethyl-2-((4-methyl-5-oxo-2,5-dihydrofuran-2-yloxy) methylene)-7-(thiophen-2-yl)-1,2-dihydrocyclopenta[b]indol-3(4H)-one | ST-357 |
| 10 | (2E)-2-[(2,5-dihydro-4-methyl-5-oxofuran-2-yloxy)methylene]-1,2-dihydro-7-(2,3-dihydrothieno[3,4-b][1,4]dioxin-7-yl)-1,4-dimethyl-cyclopenta[b]indole-3-(4H)-one | ST-362 |
| 11 | (±) 2E-4-methyl-2-(4-methyl-5-oxo-2,5-dihydrofuran-2-yloxymethylene)-6-thiophen-2-yl-1,4-dihydro-2H-cyclopenta[b]indol-3-one | MEB-55 |

The general terms used hereinbefore and hereinafter preferably have within the context of this disclosure the following meanings, unless otherwise indicated.

As used in the present invention, the term "$C_1$-$C_6$ alkyl" refers to straight or branched hydrocarbon chains, including substituted hydrocarbon chains such as haloalkyl, containing at least one carbon atom and at most 6 carbon atoms.

The term "alkenyl" refers herein to straight or branched hydrocarbon chains in which at least one bond is a double bond.

The term "alkynyl" refers herein to straight or branched hydrocarbon chains in which at least one bond is a triple bond.

The term "cycloalkyl" refers herein to non-aromatic cyclic compounds.

The term "heteroalkyl" refers herein to non-aromatic cyclic compounds that contain at least one non-carbon atom in the ring such as N, O or S.

The term "aryl" refers herein to ring systems in which at least one ring is an aromatic ring, either substituted or non-substituted.

The term "interchangeably" refers herein to two neighboring chemical groups that can be interchanged, that is, if essential for the initiation of mitosis. Its deregulation is involved in neoplastic transformation and it is thus useful for antiproliferative therapy.

While analyzing the impact of small interfering RNAs (siRNAs) targeted to cyclin B1 on different human tumor cell lines, cyclin B1 siRNAs reduces the protein level of cyclin B1 in HeLa, MCF-7, BT-474 and MDA-MB-435 tumor cells and thus reduces the kinase activity of Cdc2/cyclin B1 in HeLa cells and significantly suppresses the proliferation of tumor cells from different origins after transfection and increases apoptosis.

The pharmaceutically acceptable salts of compounds of formula II are formed, for example, as acid addition salts, preferably with organic or inorganic acids, from compounds of formula II with a basic nitrogen atom.

Suitable inorganic acids are, for example, halogen acids, such as hydrochloric acid or hydrobromic acid, sulfuric acid and phosphoric acid. Suitable organic acids are, for example, phosphonic acids, sulfonic acids such as methane- or ethane-sulfonic acid, benzenesulfonic acid, 2-naphthalenesulfonic acid or sulfamic acids, carboxylic acids such as acetic acid and propionic acid, glycolic acid, lactic acid, maleic acid, fumaric acid, succinic acid, adipic acid, malic acid, tartaric acid, citric acid, adamantanecarboxylic acid, furoic acid, triphenyl acetic acid, benzoic acid, salicylic acid, phthalic acid, mandelic acid, cinnamic acid or other organic protonic acids, such as ascorbic acid, amino acids, such as lysine, glutamine, aspargine, glutamic acid and aspartic acid, fatty acids such as stearic acid, palmitic acid and lauric acid.

The compounds of formula X are capable of inhibiting the growth of tumor derived cell lines, but do not inhibit the growth of normal fibroblasts. These compounds are useful, inter alia, for the treatment of neoplastic diseases, such as benign or malignant tumors. They are able to affect tumor regression and to prevent metastasic spread and the growth of micrometastases. In particular, they can be used for treating diseases such as breast, colon, lung, and prostate cancers, and melanoma.

Figure 1:
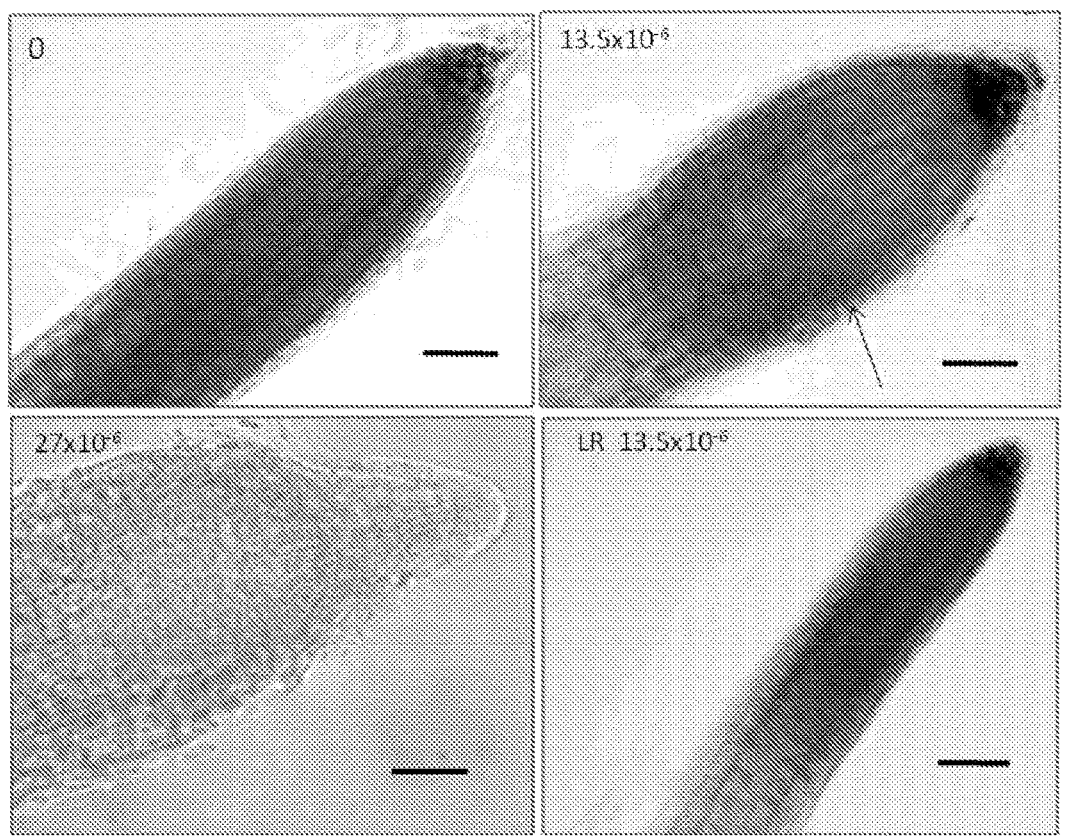
FIG. 1. depicts the effect of GR-24 on root tips. GR-24 Molar concentrations are shown. Arrow points to swollen root tip. Scale bar: 50 μm. LR—lateral root.

Impaired cell cycle progression was observed in all cancer cells in response to GR-24. In addition, increased sensitivity to GR-24 was noted in tumor stem cell cultures resulting in sphere dissociation and apoptosis at lower concentrations of GR-24. Exogenous application of GR-24 leads to alterations in cell division and differentiation in root tips. As depicted in FIG. 1, exposure of WT seedlings to 13.5 µM of exogenously supplied GR-24 leads to deformation of the root tips, causing them to look swollen; in addition, a two fold increase of GR-24 (27 µM) abolished the starch granules in the columella cells.

The experimental results provided herein indicate that the alterations in root tip morphology apparent upon GR-24 application are associated with changes in cell division in root tips.

Figure 2:
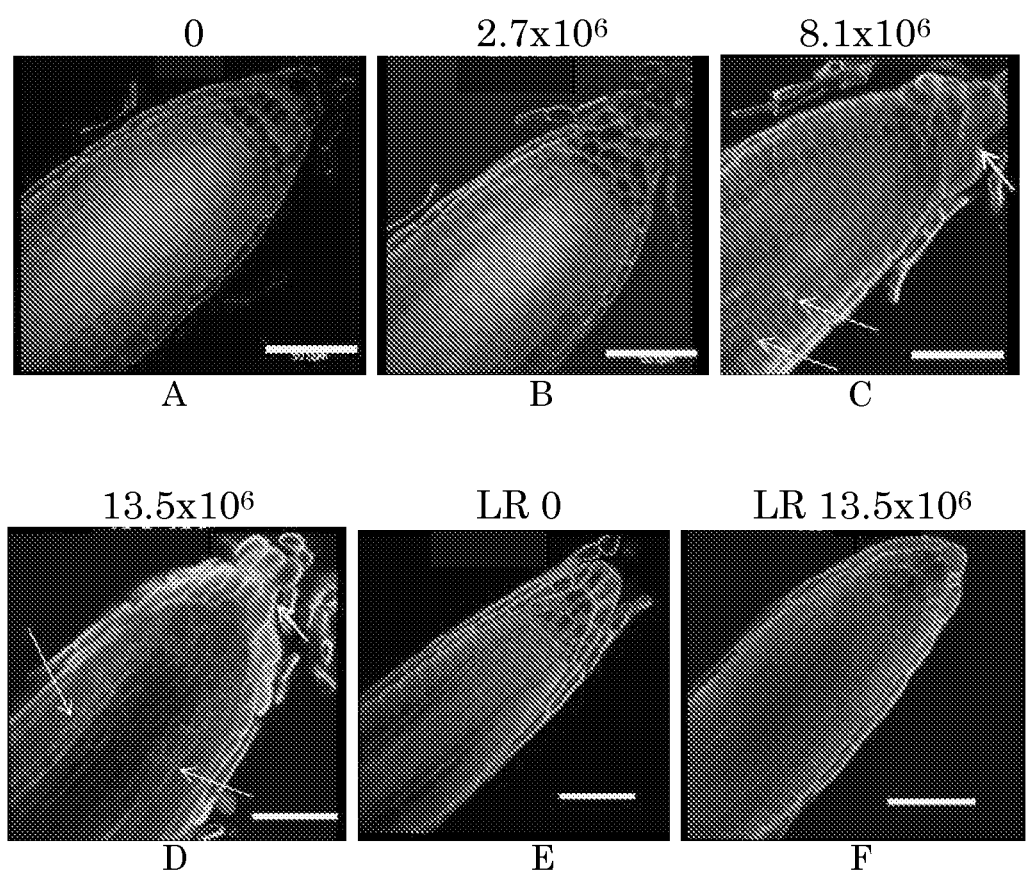
FIG. 2. depicts the effect of GR-24 on root-tip cell organization. GR-24 Molar concentrations are shown. Arrow points to sites of aberrant cell division. Scale bar: 50 μm. LR—lateral root.

As depicted in FIG. 2, examination at the cellular level shows that root-cap cells become disorganized upon GR-24 treatment, in comparison to controls. Cell division is abnormal, with randomized division of cell files in the meristematic zone of the root tips; columella cells are expanded and their organization is altered. Furthermore, lateral root meristems are less affected by GR-24 than those of the primary roots, with a reduced effect on root-tip morphology, cell division and columella-cell organization in the former.

The CYCB1 transcription levels are reduced by GR-24 treatment as determined by the level of CYCB1 gene transcription in root tips, as a measure of the level of cell division. At lower levels of GR-24 treatment (2.7 µM), CYCB1 transcription is unaffected (0.97±0.47) relative to controls. As depicted in FIG. 2, no difference in cell division between roots treated with this GR-24 concentration and controls is observed. However, under higher concentrations of GR-24 (13.5 µM), CYCB1 transcription is markedly reduced in GR-24-treated root tips (0.16±0.00) in comparison to controls. Accordingly, under these conditions, differences in cell division are observed between GR-24-treated roots and controls (FIG. 2).

Exogenous application of 3 µM of GR-24 leads to a significant increased level of GRIM REAPER (GRI) [NM_104192] gene expression, which is induced by 2.3 fold upon GR-24 treatment wherein the GRI gene expression is associated with apoptosis in Drosophila, as a cell death activator.

In contrast, said GRI gene transcription is not induced in max2-1 mutants, mutated in strigolactone signaling upon GR-24 treatment, and since max2-1 is insensitive to strigolactone analogs, it indicates that GRI expression is specific to the strigolactones and strigolactone analogs signaling pathway. The said elevation of GRI transcription, and, in accordance, reduction of CYCB1 transcription is verified by quantitative PCR experiments, as detailed in Table 2 below demonstrating the transcription levels of GRI and CYCB1 in WT and max2-1 seedlings treated with GR-24 (3 µM) versus controls.

TABLE 2

Strigolactone analogs inhibit MCF-7 monolayer growth

| Arabidopsis line | Strigolactone analog | GRI | CYCB1 |
|---|---|---|---|
| WT | GR-24 | 33.008 ± 7.121 | 0.008 ± 0.003 |
|  | ST-357 | ND | 0.460 ± 0.362 |
|  | ST-362 | ND | 0.008 ± 0.007 |
| max2-1 | GR-24 | 0.214 ± 0.193 | 0.211 ± 0.078 |

ND—not determined

The results detailed herein demonstrate that GR-24 application leads to reduction of cell cycle activity in plant roots as well as to specific induction of cell death associated gene, the latter in WT but not in strigolactone insensitive mutant.

The effect of ST-357 and ST-362 application was tested on CYCB1 transcription, wherein ST-362, similarly to GR-24, leads to a marked reduction in the level of CYCB1 transcription levels upon seedlings treatment, as detailed in Table 2. Without wishing to be bound by any particular theory, this reduction in CYCB1 transcription shows that the strigolactone analog ST-362 leads to reduction of cell cycle activity in plant roots, similarly to the effect of GR-24.

The $IC_{50}$ values are defined herein as that concentration of active ingredient at which the number of cells per well at the end of the incubation period is only 50% of the number of cells in the control cultures. The $IC_{50}$ values thus determined are, for the compounds of formula II, approximately from 0.1 to 50 µmoliliter. The $IC_{50}$ value of the compound GR-24 for breast cancer cells both luminal (estrogen receptor positive) and basal (estrogen receptor negative) is in the range of micromolar concentration.

Figure 3A:
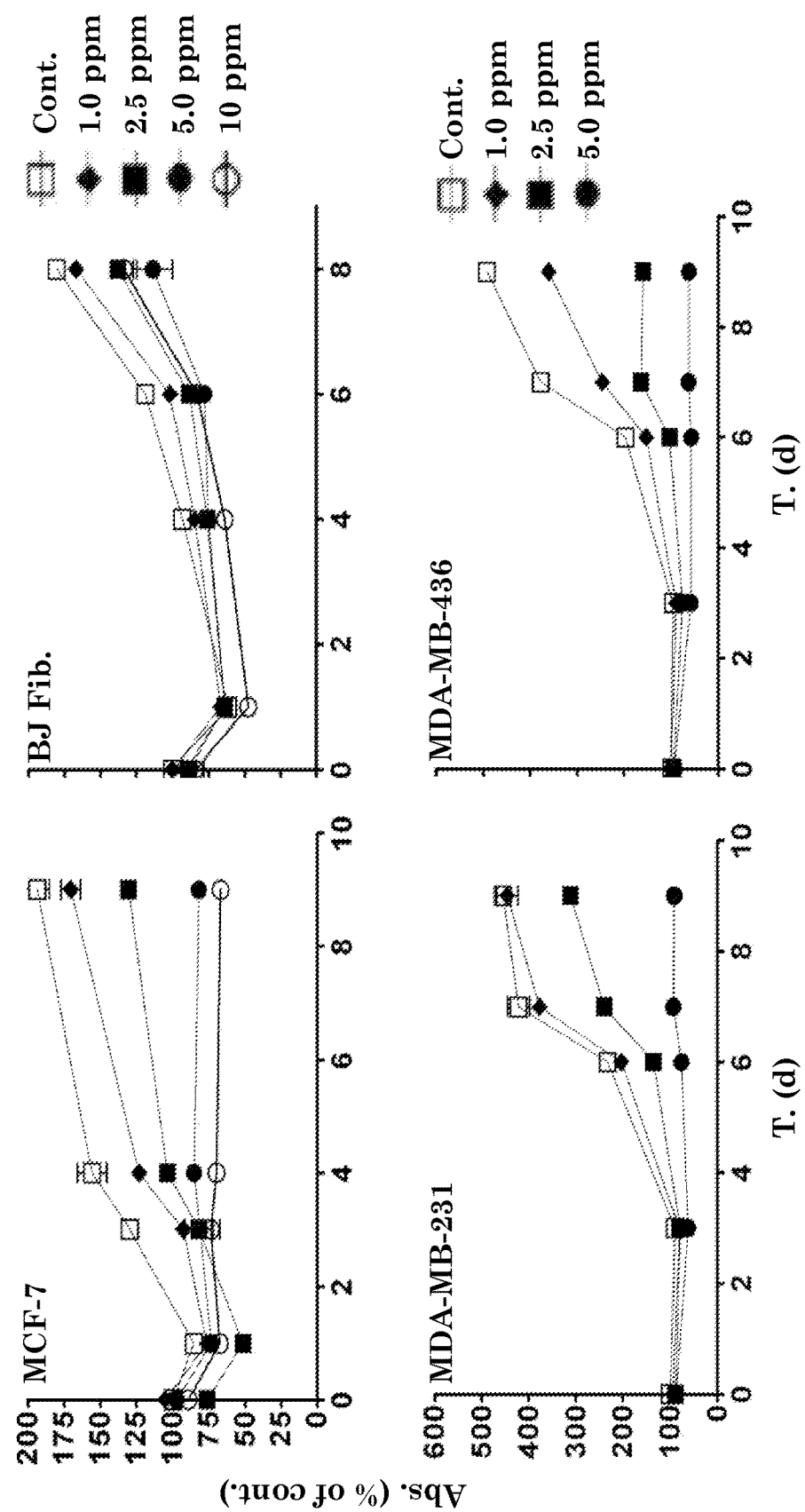
FIG. 3. shows the effect of GR-24 on breast cancer cell line proliferation: (A) absorbance graphs of MDA-MB-231, MDA-MB-436, MCF-7 and BJ 'normal' fibroblasts exposed to GR-24. (B) a graph showing absorbance (560 nm) after 7 days exposure to GR-24.

As detailed herein below in the Experimental section, GR-24 inhibits the growth of human breast cancer cell lines. The effect of GR-24 on long-term cancer cell line growth was assessed by crystal violet assay. MCF-7 (estrogen receptor (ER+), tumorigenic, non-metastatic), MDA-MB-231, MDA-MB-436 (ER−, metastatic) and BJ fibroblasts (normal, non-neoplastic line), were treated with GR-24 at a dose range of 0.5 to 10 ppm (1.65-33 µM). Growth was monitored for up to 10 days. Concentrations of 2.5-5 ppm of GR-24 resulted in a significant reduction in growth compared to vehicle treated controls. BJ fibroblasts showed no significant reduction in growth over this time period, even at concentrations of up to 10 ppm as depicted in FIG. 3A. The concentration of GR-24 at which 50% of long-term proliferation was inhibited ($IC_{50}$) after 7 days is demonstrated in FIG. 3B, wherein optical densities at day 7 are plotted as a percentage of vehicle controls. $IC_{50}$ concentrations for MDA-MB-231, MDA-MB-436 and MCF-7 cells were 6.7 ppm (22.1 µM), 5.7 ppm (18.8 µM) and 5.7 ppm (18.8 µM) respectively.

Figure 5A:
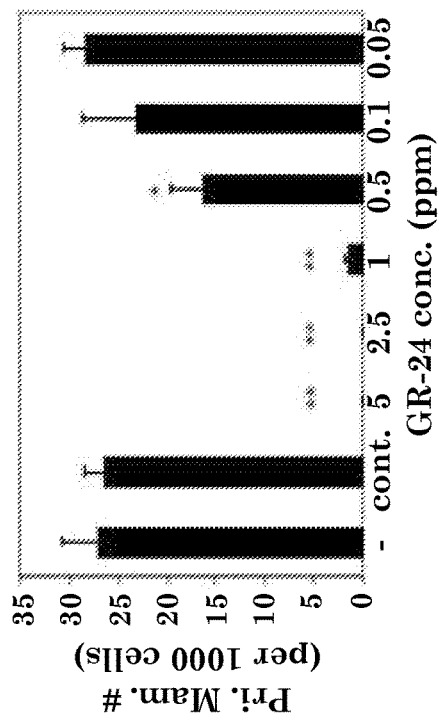
Figure 5A:
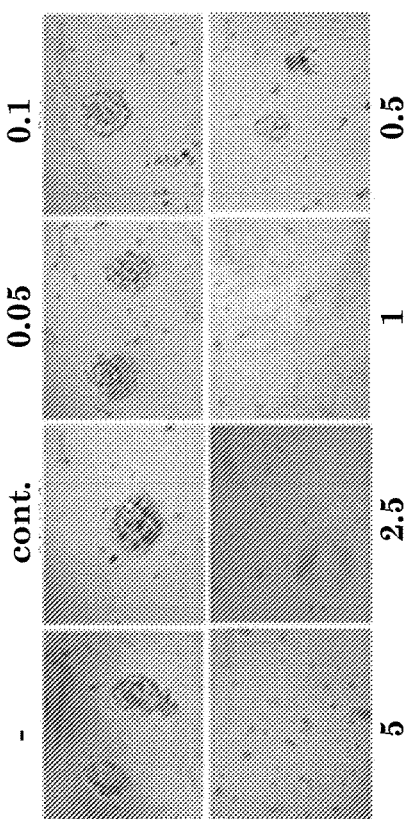
Figure 5B:
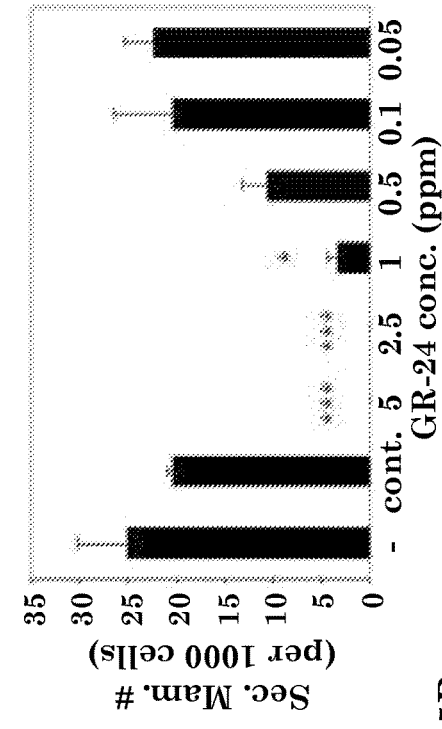
Figure 5B:
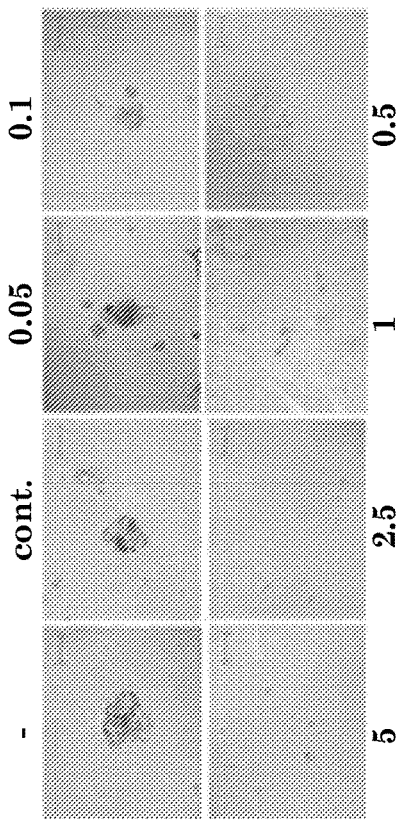
Figure 5C:
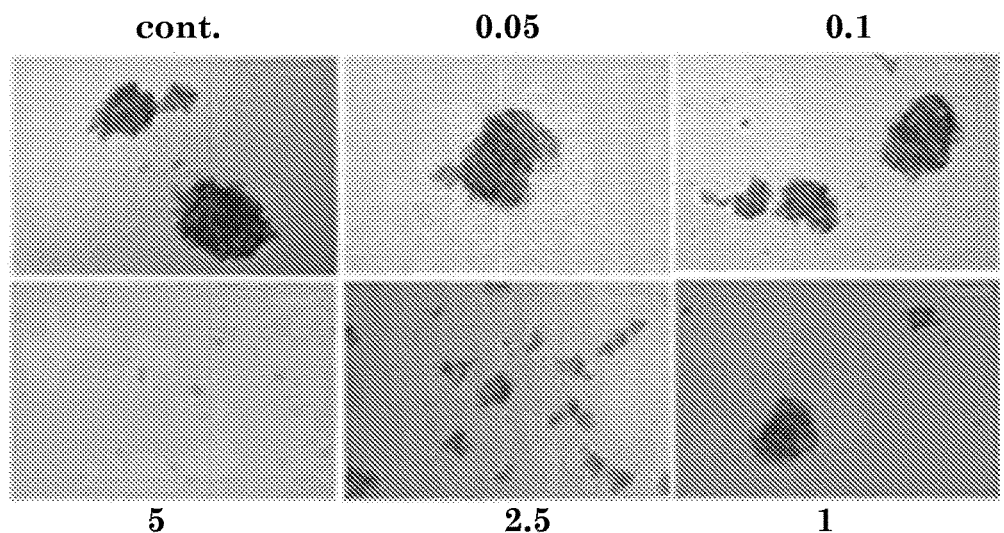

As further detailed herein below in the Experimental section, GR-24 induces G2-arrest and apoptosis in cancer cells. To investigate the effect of GR-24 on cell cycle progression, DNA content analyses were carried out by Propidium Iodide (PI) staining using flow cytometry as depicted in FIG. 4. MCF-7, MDA-MB-231 and MDA-MB-436 cells were treated with concentrations of 5, 2.5 and 0.5 ppm GR-24 for 48 hours. FIG. 4 demonstrates the percentages of cells in each phase of the cell cycle. GR-24 treatment causes a dose dependant increase in the percentage of cells in G2 phase and a concomitant decrease in the percentage of cells in G1 phase in all assayed cancer cell lines. At higher concentrations (5 ppm), GR-24 causes an increase in the sub-G1/apoptotic fraction indicating an increased apoptosis. Conversely, treatment of the immortalized, non-transformed mammary cell line, MCF10A, with GR-24 results in an increase in the cells arrested at the G1 phase of the cell cycle and not in the G2/M phase while no increase in apoptosis was observed. As further detailed herein below in the Experimental section, GR-24 inhibits the growth and reduces viability of breast cancer stem cells. Tumor Initiating Cells (hereinafter TICs) or Cancer Stem Cells (CSCs) that are intrinsically resistant to conventional chemo- and radiation-therapies are able to regenerate the cellular components of the original tumor eradicated by the said treatments, and ultimately lead to recurrence. To determine if GR-24 could inhibit MCF-7 mammosphere formation, MCF-7 cells were grown as mammospheres in the presence or absence of GR-24, as depicted in FIG. 5A. Mammosphere formation was completely inhibited in the presence of 0.5-2.5 ppm of GR-24, and severely attenuated at 1 ppm, ($p<0.01$), 5 fold below the concentration required to inhibit monolayer growth, as shown in FIG. 4. At 0.5 ppm concentrations, growth is inhibited to a lesser degree albeit mammospheres are often smaller (<50 μM) than vehicle treated controls ($p<0.05$). Similar results were obtained when secondary MCF-7 mammospheres were grown in the presence of GR-24 as demonstrated in FIG. 5B. Another breast cancer cells line, MDA-MB-231, was tested as depicted in FIG. 5C. At 5 ppm, GR-24 completely blocked MDA-MB-231 mammosphere formation. At 2.5 ppm, mammopheres growth was severely attenuated, with mammospheres being substantially smaller (<50 μM) compared to vehicle control groups. The concentrations of GR-24 necessary to block MCF-7 and MDA-MB-231 mammosphere formation were 5.7 and 2.7 fold lower respectively than the $IC_{50}$ doses for monolayer growth.

Without wishing to be bound by any particular theory, the mammospheres surprisingly exhibit a greater sensitivity to the growth inhibitory effects of GR-24 versus monolayer culture while TICs have been shown to be inherently resistant to chemotherapy as shown, e.g., by Xiaoxian Li et al., J. Nat. Cancer Inst. (JNCI), Vol. 100(9): 672-679, 2008.

Ginestrier C. et al., Cell Stem Cell, 1: 555-567, 2007, have reported that normal and cancer human mammary epithelial cells with increased aldehyde dehydrogenase activity (ALDH) have stem/progenitor properties and that high ALDH activity identifies the tumorigenic cell fraction, capable of self-renewal and of generating tumors that recapitulate the heterogeneity of the parental tumor. PE Burger and R Gupta, Stem Cells, 27(9): 2220-8, 2009, shows that high levels of aldehyde dehydrogenase 1 (hereinafter ALDH1) activity are present in a subset of prostate epithelial cells that co-express a number of antigens found on stem/progenitor cells of other origins (CD9, Bcl-2, CD200, CD24, prominin, Oct 3/4, ABCG2, and nestin). Almost all of these cells expressing high levels of ALDH1 activity also express Sca-1 and a third of them express high levels of this antigen. The cells with high levels of ALDH activity have greater in-vitro proliferative potential than cells with low ALDH activity.

Tumors contain small population of Cancer Stem Cells (CSC) that are responsible for its maintenance and relapse. Analysis of these CSCs may lead to effective prognostic and therapeutic strategies for the treatment of cancer patients. Feng Jiang et al., Mol. Cancer Res., 7(3): 330-8, 2009, demonstrates the identification of CSCs from human lung cancer cells using Aldefluor assay followed by fluorescence-activated cell sorting analysis. Isolated cancer cells with relatively high aldehyde dehydrogenase 1 (ALDH1) activity display in-vitro features of CSCs, including capacities for proliferation, self-renewal, and differentiation, resistance to chemotherapy, and expressing CSC surface marker CD133. In-vivo experiments show that the ALDH1-positive cells could generate tumors that recapitulate the heterogeneity of the parental cancer cells. ALDH1 has thus been shown to be a functional marker in the isolation of TICs of various cancer types. An Aldefluor kit is usually used, which is designed for optimal identification and isolation of stem cells through specific interaction with human ALDH1. Thus, the cells are suspended in Aldefluor assay buffer, containing uncharged ALDH1-substrate and BODIPY-aminoacetaldehyde (BAAA), which is incubated followed by taking up BAAA by living cells through passive diffusion and then converted by intracellular ALDH into a negatively charged reaction product BODIPY-aminoacetate, which is retained inside cells expressing high levels of ALDH1, causing these cells to become brightly fluorescent.

Figure 6A:
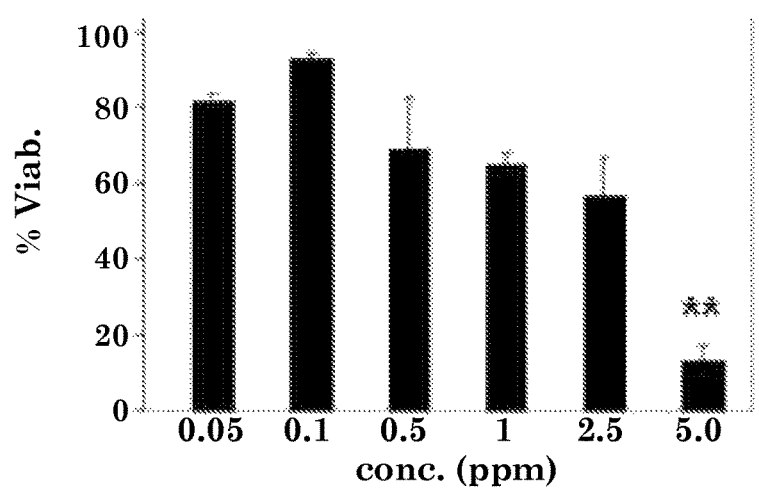
Figure 6B:
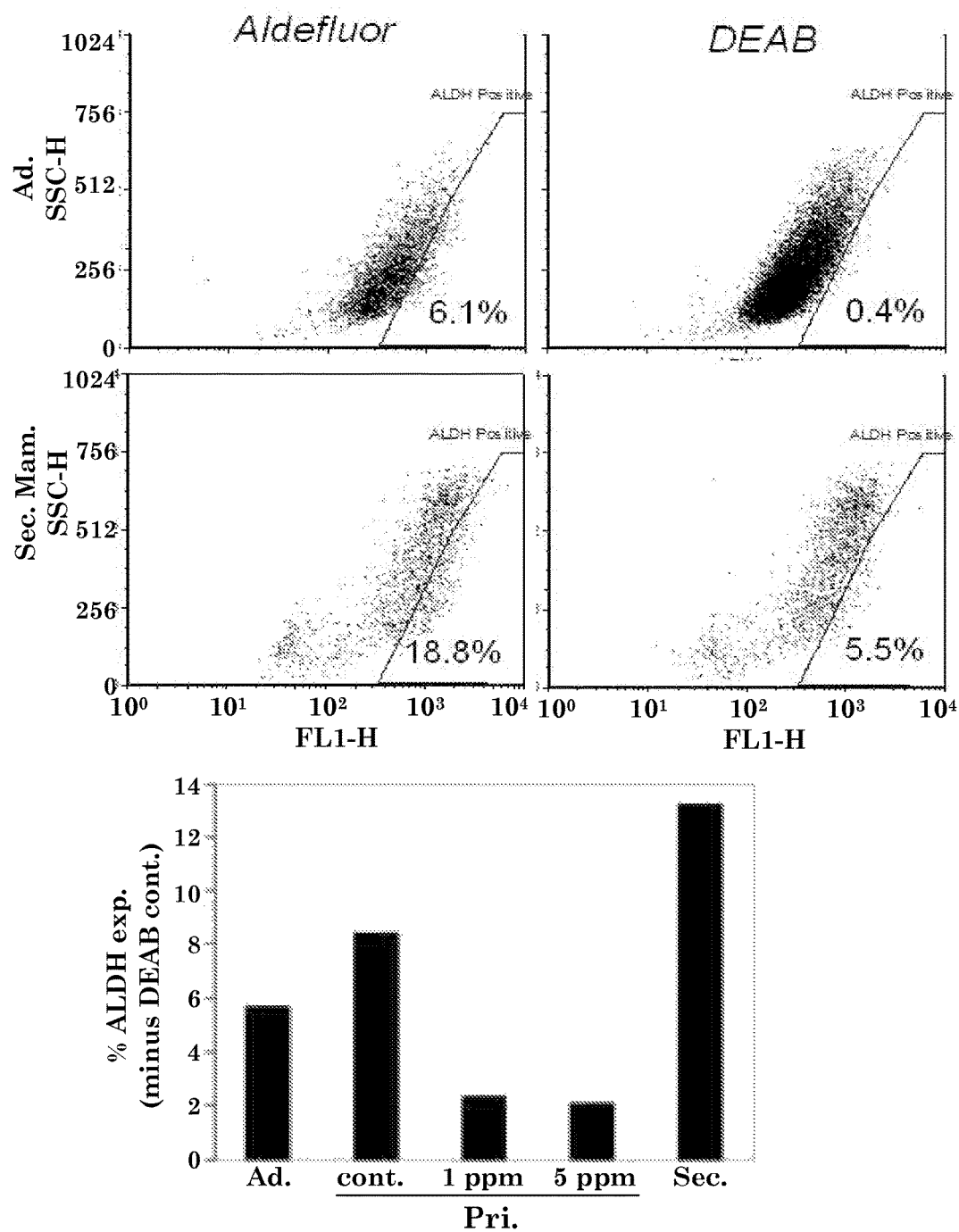

As further detailed herein below in the Experimental section, the effect of GR-24 on mammosphere viability and on stem cells marker expression (ALDH1) was assessed by 2,3-bis(2-methoxy-4-nitro-5-sulfophenyl)-5-[(phenylamino)-carbonyl]-2H-tetrazolium inner salt (hereinafter XTT) assay (ATCC). At 5 ppm, GR-24 reduces the viability by approximately 80% (98.4%+3.4 to 16.4%+4.6). At 2.5 ppm, where mammosphere formation is completely inhibited, viability remains at 68.6%+12.4, indicating that increased cell death cannot explain the inhibition in mammosphere formation at this concentration. To further investigate GR-24 induced inhibition of mammosphere formation, the expression of breast stem cell markers were examined. Secondary mammospheres were assayed for ALDH activity to ensure enrichment versus adherent cultures. Secondary mammospheres exhibit a 2.4 fold enrichment of ALDH activity, as depicted in FIG. 6B. Primary mammospheres exhibit an increase in ALDH activity from 6% to 8%. GR-24 treatment of primary mammospheres reduces ALDH activity from 6% to 2%.

Without wishing to be bound by any particular theory, the reduction in ALDH activity suggests that GR-24 inhibits mammosphere formation in part by regulating cancer stem cell markers.

As further detailed herein below in the Experimental section, the strigolactone analogs ST-357, ST-362, EG-9c, EG-5 and MEB-55 are effective growth inhibitors of various types of cancer cell lines, as demonstrated by testing the ability of said strigolactone analogs to inhibit the growth of MCF-7 and MDA-MB-231 cells. MCF-10A cells were used as non-tumorigenic line and various cell lines derived from other types of solid tumors were compiled including colon (HCT116, HT29, SW480), prostate (PC3, DU145, LNCaP), lung (A549), osteosarcoma (U20S) and Melanoma (T11) cell lines. A non-adherent leukemic cancer cell line, K562, was also included to further diversify the cohort (FIG. 7). Cell lines exhibit substantial variation in their response to each strigolactone analog, however all lines were growth inhibited by the strigolactone analogs treatment, with an $IC_{50}$ concentration of from 2.9 to 12.8 ppm for MEB-55 and ST-362, and from 3.9 to 18.3 ppm for EG-5, EG-9c and ST-357. Interestingly the osteosarcoma derived line, U20S, exhibited a similar sensitivity to all five strigolactone analogs ($IC_{50=2.7}$ to 4.5 ppm), while the hormone dependent prostate line, LNCaP was growth inhibited by all, except EG-9c.

TABLE 3

IC$_{50}$ concentrations of strigolactone analogs

| Tumor cell Lines | IC$_{50}$ (ppm) at 72 h. | | | | |
|---|---|---|---|---|---|
| | EG-5 | EG-9C | ST-357 | ST-362 | MEB-55 |
| Breast | | | | | |
| MCF10A | >15 | >15 | >15 | >15 | >15 |
| MCF-7 | 17.5 | 17.3 | >20 | 8.1 | >12.8 |
| T47D | 8.8 | >10 | >10 | 8.6 | 5.0 |
| MDA-MB-231 | 7.5 | >10 | 5.0 | 2.9 | 3.9 |
| MDA-MB-436 | ND | >10 | ND | 5.9 | 8.3 |
| Prostate | | | | | |
| PC3 | >15 | >15 | 5.4 | >15 | 8.8 |
| DU145 | >15 | 15 | >15 | 7.5 | 12.8 |
| LNCaP | 13 | >20 | 14.4 | 9.8 | 12 |
| Colon | | | | | |
| HT-29 | >15 | >15 | >15 | 7.3 | 8.2 |
| HCT116 | >15 | >15 | >15 | 6.0 | 12.8 |
| SW480 | >15 | >15 | >15 | 2.9 | 9.7 |
| Leukemia | | | | | |
| K562 | >15 | >15 | >15 | 4.3 | 8.1 |
| Lung | | | | | |
| A549 | 18.3 | 13.5 | 10.6 | 6.7 | 6.9 |
| Osteosarcoma | | | | | |
| U20S | 3.9 | 4.5 | 4.5 | 2.8 | 2.7 |

As further detailed herein below in the Experimental section, strigolactones and strigolactone analogs inhibit growth through a G2-phase arrest and cause apoptosis at higher concentrations wherein the GR-24 treatment causes an increase in the percentage of MCF-7 and MDA-MB-231 cells in G2-phase. Cells were treated with strigolactone analogs to determine whether or not they alter cell cycle progression in the same way. Dose dependant increases in the percentage of cells in G2 phase were observed. At concentrations 25% above the IC$_{50}$/72 h, increased apoptosis was observed in MDA-MB-231 cells with increased percentages of cells in the subG1 fraction. Hoechst staining was used to analyze changes in the nucleus. ST-362 treatment at 10-15 ppm results in increased nuclear condensation and fragmentation, changes indicative of apoptosis. To determine if continual strigolactone analog exposure is required for growth inhibition and reduced cell survival, MDA-MB-231 cells were treated with either ST-362 or MEB-55 at 10 ppm and 5 ppm for 2, 4 and 24 hours. At each time point the strigolactone analog was removed and media replaced with fresh growth media. After a total of 24 hours, an XTT assay was carried out. A significant decrease in viability was induced after 4 hours of the strigolactone analog treatment (p<0.01). No significant changes were observed after 2 hours. Continual exposure (24 h) to each strigolactone analog induced a greater reduction in cell viability (p<0.001) compared to the 4 hours exposure, indicating that a long term treatment strategy is more effective at reducing cancer cell viability (FIG. 9).

As further detailed herein below in the Experimental section, the strigolactone analogs ST-357, ST-362, EG-9c, EG-5 and MEB-55 are able to completely block mammosphere formation at concentrations of 5 ppm and above (FIG. 10). ST-362 and MEB-55 are able to block mammosphere growth at 2.5 ppm. ST-357 shows significant reduction in mammosphere growth at 2.5 ppm (p<0.01). ST-357, ST-362 and MEB-55 significantly inhibit mammosphere formation at 1 ppm (p<0.01). The potency of the above mentioned strigolactone analogs being inducers of G2 arrest is depicted in FIG. 8 in monolayer MCF-7 cultures. However, like GR-24, the doses required to inhibit mammosphere formation are lower than that required to inhibit proliferation in monolayer cultures (5 fold lower for ST-362 and MEB-55; 3 fold lower for ST-357). To determine if the sensitivity to strigolactone analog treatment was specific to mammosphere formation or whether it extended to the integrity and survival of mature mammospheres, MCF-7 mammospheres were grown in the absence of any strigolactone analog and after 7 days (or once mammospheres had reached a mean diameter of over 100 μM), strigolactone analogs were added to the growth media as depicted in FIG. 11 at the indicated doses. After 48 hours, mammospheres treated with ST-362, ST-357 and MEB-55, at doses of 2.5-5 ppm, exhibited a looser morphology and appeared to be dissociating. Representative images of mammospheres treated with 5 ppm concentration are shown in FIG. 11A.

Thus, in one aspect of the invention there is provided a use of strigolactones and/or strigolactone analogs that are compounds of formula X, or individual isomers or mixtures of isomers and pharmaceutically acceptable salts of such compounds thereof, optionally in combination with one or more other pharmaceutically active compounds, for the preparation of an antineoplastic pharmaceutical composition for the treatment of a disease which responds to an inhibition of cell growth, wherein the disease is a neoplastic disease.

Additionally, provided herein is the use of strigolactones and/or strigolactone analogs of formula X, or individual isomers or mixtures of isomers and pharmaceutically acceptable salts of such compounds thereof, optionally in combination with one or more other pharmaceutically active compounds, for the preparation of pharmaceutical compositions for the treatment of breast, lung, prostate and colon cancer and melanoma.

The abovementioned medicaments are further suitable for treating warm-blooded animals suffering from a tumoral disease, by administering to warm-blooded animals requiring such treatment an effective, tumor-inhibiting amount of a compound of formula X or a pharmaceutically acceptable salt thereof.

In addition, the pharmaceutical compositions of the invention are suitable for use in the therapeutic treatment of the human or animal body. Effective doses are administered to a warm-blooded animal of approximately 70 kg body weight according to species, age, individual condition, mode of administration and the individual syndrome.

Examples of compounds of formulas II or the salts thereof that can be used for producing a medicament for preparing pharmaceutical compositions for use in the therapeutic treatment of the human or animal body are: 3aR*,8bS*,E)-3-(((R*)-4-methyl-5-oxo-2,5-dihydrofuran-2-yloxy)-methylene)-3,3a,4,8b-tetrahydro-2H-indeno[1,2-b]furan-2-one, (±) (2E)-4-methyl-2-(4-methyl-5-oxo-2,5-dihydrofuran-2-yloxymethylene)-1,4-dihydro-2H-cyclopenta[b]indol-3-one, (±)(2E)-7-bromo-4-methyl-2-(4-methyl-5-oxo-2,5-dihydrofuran-2-yloxymethylene)-1,4-dihydro-2H-cyclopenta[b]indol-3-one, (±)(2E)-4-methyl-2-(4-methyl-5-oxo-2,5-dihydrofuran-2-yloxymethylene)-7-(4-nitrophenyl)-1,4-dihydro-2H-cyclopenta[b]indol-3-one, (±) (2E)-4-methyl-2-(4-methyl-5-oxo-2,5-dihydrofuran-2-yloxymethylene)-7-(2-thienyl)-1,4-dihydro-2H-cyclopenta[b]indol-3-one, (±)(2E)-4-methyl-2-(4-methyl-5-oxo-2,5-dihydrofuran-2-yloxymethylene)-7-[(4-dimethylamino)-phenyl]-1,4-dihydro-2H-cyclopenta[b]indol-3-one, (2E)-7-(1-methoxynaphthalen-2-yl)-1,4-dimethyl-2-((4-methyl-5-oxo-2,5-dihydrofuran-2-yloxy)methylene)-1,2- dihydrocyclopenta[b]indol-3(4H)-one, (2E)-2-[(2,5-dihydro-4-methyl-5-oxofuran-2-yloxy)methylene]-1,2-dihydro-7-[4-(dimethylamino)pheny]-1,4-dimethylcyclopenta[b]indole-3-(4H)-one, (2E)-1,4-dimethyl-2-((4-methyl-5-oxo-2,5-dihydrofuran-2-yloxy) methylene)-7-(thiophen-2-yl)-1,2-dihydrocyclopenta[b] indol-3(4H)-one, (2E)-2-[(2,5-dihydro-4-methyl-5-oxofuran-2-yloxy)methylene]-1,2-dihydro-7-(2,3-dihydrothieno[3,4-b][1,4]dioxin-7-yl)-1,4-dimethyl-cyclopenta[b]indole-3-(4H)-one, (±), 2E-4-methyl-2-(4-methyl-5-oxo-2,5-dihydrofuran-2-yloxymethylene)-6-thiophen-2-yl-1,4-dihydro-2Hcyclopenta[b]indol-3-one.

Further provided is a method of using a compound of formula X, or individual isomers or mixtures of isomers and pharmaceutically acceptable salt of such a compound thereof for the preparation of a pharmaceutical composition for killing cancer stem cells. Also provided are methods of treating a subject who has been treated for cancer with a compound of formula X, or individual isomers or mixtures of isomers and pharmaceutically acceptable salt of such a compound thereof. The method of the invention may in various instances kill cancer stem cells and reduce the risk of recurrence of cancer in the subject.

Provided herein are pharmaceutical compositions comprising an antiproliferative effective amount, especially, but not limitatively, an amount effective in the therapy of neoplastic conditions, of the active ingredient of formula X together with pharmaceutically acceptable carriers that are suitable for topical, enteral, for example oral or rectal, or parenteral administration, and may be inorganic or organic, solid or liquid.

Further provided is a pharmaceutical composition comprising the compounds of formula X as described herein, and additional pharmaceutically accepted additives or excipients. Excipients that can be employed include any excipients known in the art for producing solid dosage forms such as glucose, lactose, mannitol, sorbitol, erythritol, maltodextrin, regular or pregelatizined starch, povidone, polyvinylpyrrolidone, carboxymethylcellulose sodium, hydroxyethyl cellulose, hydroxypropyl methyl cellulose, gelatin, guar gum, xanthan gum, citric acid, sodium silico aluminate, magnesium stearate, polyethylene glycol, propylene glycol, polysorbate 20, 40, 60 or 80, titanium dioxide, talc, and the like.

Preparation of compounds of formula X is known in the art and therefore is not described herein in detail, for the sake of brevity. The compounds of formula II (i.e. strigolactone analogs) can be prepared as described, e.g., by Prandi et al., Eur. J. Org. Chem., 2011, 3781-93; Asami T & Ito S., Design and Synthesis of Function Regulators of Plant Hormones and their Application to Physiology and Genetics, J. Synthetic Org. Chem. Japan, 2012, 70:36-49; Malik H. et al., A new efficient synthesis of GR-24 and dimethyl A-ring analogues, germinating agents for seeds of the parasitic weeds *Striga* and *Orobanche* spp., Tetrahedron, 2010, 66:7198-7203; Mwakaboko A. S. et al., Single step synthesis of strigolactone analogues from cyclic keto enols, germination stimulants for seeds of parasitic weeds, Bioorg. & Med. Chem., 2011, 19:5006-5011; Boyer F D, et al., Structure-activity relationship studies of strigolactone-related molecules for branching inhibition in garden pea: molecule design for shoot branching, Plant Physiology, 2012.

Natural strigolactones, represented herein by, e.g. formula I, can be prepared as described, e.g., by Xie et al., Annu. Rev. Phytopathol., 2010, 48: 93-117, and references therein; Yoneyama et al., Plant Growth Regul., 2011, 65: 495-504; and Ueno et al., J. Agric. Food Chem., 2011, 59: 9226-9231; Chen V X et al., Stereochemistry, Total Synthesis, and Biological Evaluation of the New Plant Hormone Solanacol. Chemistry—a European Journal, 2010, 16:13941-13945; Kitahara S. et al., First synthesis of (+/−)-sorgomol, the germination stimulant for root parasitic weeds isolated from *Sorghum bicolor*, Tetrahedron Lett., 2011, 52:724-726; Reizelman A. et al., Synthesis of all eight stereoisomers of the germination stimulant strigol, Synthesis-Stuttgart, 2000, 1944-1951; Reizelman A. et al., Synthesis of the germination stimulants (+/−)-orobanchol and (+/−)-strigol via an allylic rearrangement, Synthesis-Stuttgart, 2000, 1952-1955; Sasaki M., Synthesis and biological activity of strigolactones, J. Pesticide Science, 2009, 34:315-318.

The following examples further illustrate the invention, and should not be construed as in any way limiting its scope.

It is noted that "strigolactone analogs" as used herein, includes all forms of strigolactones of formula II, including, their pre-form, prodrugs, derivatives, recombinants, or any acceptable form thereof which have activity similar to native strigolactones.

It is noted that "strigolactones" as used herein, includes all forms of natural strigolactones, including those of formula I, including, their pre-form, prodrugs, derivatives, recombinants, or any acceptable form thereof which have activity.

The term "prodrug" means that upon administration, the compound undergo chemical conversion by metabolic processes before becoming pharmacologically active substance. In general, such prodrugs will be functional derivatives of the present compounds, which are readily convertible in-vivo into active strigolactones.

The compositions according to the invention may be used advantageously for treating neoplastic conditions or symptoms caused therefrom. The compositions of the invention may be used to treat persons (or animals) suffering from neoplastic conditions (e.g. cancer), wherein the patient is orally administered a therapeutically active dose of strigolactones analogs.

The strigolactones are, in another aspect of the invention, advantageously used for treating all cancer types, e.g. lung, colon, breast, skin, melanoma etc. Said treating may lead to disappearance or mitigation of all or part of the symptoms associated to cancer.

In a specific embodiment, the strigolactones or strigolactone analogs and the compositions comprising them, are stable for at least one month to one year. The term "stable" as used herein means that the active ingredients maintain their biological activity.

To term "effective amount" of an active agent includes an amount effective to treat, reduce, alleviate, ameliorate, eliminate or prevent one or more symptoms of the disease sought to be treated or the condition sought to be avoided or treated, or to otherwise produce a clinically recognizable favorable change in the pathology of the disease or condition. Active agents can be presented in the dosage form in effective amounts, or in a number of the dosage forms applied at about the same time in amounts that total effective amounts.

The term "patient" includes human and non-human animals. The patient to be treated is preferably a mammal.

The terms "treatment", "treating" and "treat", as used herein, include their generally accepted meanings, i.e., the management and care of a patient for the purpose of preventing, prohibiting, restraining, alleviating, ameliorating, slowing, stopping, delaying, or reversing the progression or severity of a disease, disorder, or pathological condition, described herein, including the alleviation or relief of symptoms or complications, or the cure or elimination of the disease, disorder, or condition.

The following examples are set forth to further illustrate the strigolactones and analogs thereof of the invention. The below examples, however, should not be construed as limiting the present invention in any manner.

EXAMPLES

Statistical Analysis

Results are presented as Average±SD of replicate analyses and are either representative of, or inclusive of at least two independent experiments. Statistical analyses were performed using student's t-test (2-tailed, paired) versus vehicle controls and are regarded as being significant when P<0.05 (*). Higher powers (p<0.01, p<0.001) are also employed and indicated in each figure legend. $IC_{50}$ doses for strigolactone analogs were calculated by interpolation of the sigmoidal dose response curves (Graphpad Prism 4.0 software). Briefly, linear regression was performed between relevant y-axis data points and interpolation calculated for x-axis unknowns.

Example 1

Germination of the Seeds of *Arabidopsis thaliana*

Seeds of homozygous lines of *Arabidopsis thaliana* wild type (WT; Columbia; Col-0) and max2-1 mutant (http://abrc.osu.edu/) were surface-sterilized and germinated on 1/2 Murashige and Skoog (MS) plates supplemented with 1% sucrose and solidified with 0.7% agar. Plates were incubated vertically in the dark at 4° C. for two days to synchronize germination. Three days after germination, seedlings were gently transferred using forceps to 1/2 MS plates containing various concentrations of GR-24 as a mixture of four diastereomers: (±)-GR-24 and (±)-2'-epi-GR-24. The root tip of the transferred seedling was marked on the plates. The plates remained unsealed to prevent accumulation of gases (e.g., ethylene), and were positioned in an upright 45° position, and incubated at 22° C. with a light intensity of 50-60 mol photons m-2 s-1 provided by white fluorescent tubes and under a photoperiod of 16 hours exposure to light/8 hours in the dark for 6-12 days.

GR-24 treatments were conducted at concentrations ranging from $2.7 \times 10^{-6}$ to $13.5 \times 10^{-6}$ M. ST-357 and ST-362 treatments were conducted at a concentration of $3 \times 10^{-6}$ M.

GR-24, ST-357 and ST-362 were initially dissolved in acetone to give a 4.5 mM, 10 μM and 10 μM solutions, respectively, which were then further diluted with double-distilled sterile water (DDW). Hence, in addition to non-treated roots, experimental controls included roots treated with acetone at the concentrations used in the respective GR-24, ST-357 and ST-362 treatments. In each of the experiments, non-treated roots were compared to the respective acetone control. Where no difference was observed between the various controls, non-treated roots are shown. Where differences were recorded between non-treated and acetone controls, the comparison was made between GR-24, ST-357 and ST-362-treated and acetone-treated roots.

Example 2

Determination of Root-tip Structure and Cellular Morphology

For examination of root-tip cellular morphology and starch granules in columella cells, WT roots were grown on GR-24 and control plates as described in Example 1. Following 6 days of growth on these plates, roots were stained with iodine-potassium iodide (Lugol's solution, Sigma-Aldrich Corp., St. Louis, Mo.). Concentrated Lugol's solution (5 g iodine and 10 g potassium iodide mixed with 85 ml distilled water) was used, followed by washing with double-distilled water. Using a Leica DMLB light microscope (Leica Microsystems GmbH) equipped with a Nikon DS-Fi1 camera, pictures were taken of root tips from each treatment. Experiments were repeated four times; within each treatment, four root tips were examined per experimental repeat (FIG. 1).

For examination of the order and structure of root-cap cells, WT roots were grown on GR-24 and control plates as described in Example 1. Following to 6 days of growth on said plates, root tips were stained with Aniline Blue Solution (Sigma-Aldrich) for 5 minutes, immediately followed by staining with Calcofluor solution [100 mg Calcofluor White (Sigma-Aldrich) in 5 ml distilled water]. Stained roots were examined immediately using a confocal microscope (Olympus IX81, Tokyo, Japan). Experiments were repeated four times; within each treatment, four root tips were examined per experimental repeat (FIG. 2).

Example 3

Determination of Genes Transcription Level Using Quantitative PCR

RNA was extracted from seedlings grown and treated as described in Example 1. Quantitative PCR was performed by amplifying fragments of genes of interest (Tables 6 & 7). *Arabidopsis* 15S ribosomal RNA (GenBank accession no. AT1G04270.1) served as the reference gene for the amount of RNA, and was amplified using specific primers (forward) 5'-CAAAGGAGTTGATCTCGATGCTCTT-3' and (reverse) 5'-GCCTCCCTTTTCGCTTTCC-3'. The experiment was performed in 5-6 biological replicates; each replicate included 8 plants, on which 3 technical repeats were performed. Means and standard error were determined from all biological replicates.

Primers were designed using PrimerQuest software (Integrated DNA Technologies). RNA was extracted using Trizol (Invitrogen, Carlsbad, Calif., USA) using the manufacturer's protocol. 1 μg RNA was reverse-transcribed in a total volume of 20 μl using the Superscript First strand cDNA synthesis kit (Invitrogen). PCR was performed in triplicate using an ABI-Prism 7900 instrument (Applied Biosystems, Foster City, Calif.) and SYBR Green I detection (Applied Biosystems) according to the manufacturer's protocol. The expression of each target gene was normalized to the expression of GAPDH RNA and is presented as the ratio of the target gene to GAPDH RNA, expressed as 2-ΔCt, where Ct is the threshold cycle and ΔCt=Ct Target–Ct GAPDH.

Example 4

Preparation of Crystal Violet Monolayer Growth Assays

Cells were seeded at 1500 (MDA-MB-231, MDA-MB-436 and BJ fibroblasts) or 4000 cells per well of 96 well plates. The following day media was replaced with phenol-free DMEM supplemented with 10% charcoal-stripped Fetal Bovine Serum (hereinafter FBS) and the indicated doses of the strigolactone analogs or vehicle (acetone) alone as control. At the indicated time points, individual plates were fixed and stained with crystal violet-methanol solution (50 µl per well) for 15 minutes, washed several times with distilled water and plates were air dried overnight. Sodium citrate solution (0.1M) was used to solubilize bound crystal violet and optical densities were measured at 560 nm (Glomax®-Multi Detection plate reader, Promega).

Example 5

Hoechst 33342 Staining

MDA-MB-231 cells were seeded out into 96 well plates in triplicate at 3000 cell per well. The following day media was replaced with phenol-free DMEM supplemented with 10% charcoal-stripped FBS and the indicated final concentrations of the strigolactone analogs or vehicle (acteone) alone. After 48 hours, the medium was aspirated off and 100 µl of Hoechst dye (2 µg/ml), diluted with the medium, was added to the cells and incubated for 15 minutes. Stained cells were observed under a fluorescence microscope (Zeiss Instruments, Thornwood, N.Y.).

Example 6

Strigolactone analogs are potent inhibitors of self-renewal and survival of breast cancer cell lines grown as mammospheres and even a short exposure leads to irreversible effects on mammosphere dissociation and cell death. Immunoblot analysis revealed that strigolactone analogs induce activation of the stress response mediated by both P38 and JNK1/2 MAPK modules and inhibits PI3K/AKT activation. Taken together this study indicates that strigolactones are promising anticancer agents whose activities may be achieved through modulation of stress and survival signaling pathways. Strigolactone analogs inhibit cancer cell proliferation and induce apoptosis (in the low micromolar range). Strigolactone analogs are potent inhibitors of mammosphere formation and cancer stem-like cell survival. In addition, strigolactone analogs inhibited hormone responsive and hormone independent breast cancer cell lines. Immunoblot analysis revealed that strigolactone analogs activated the stress induced MAPKs, P38 and JNK1/2 and inhibited PDK1 and AKT.

Taken together this study indicates that strigolactones and strigolactone analogs are promising anticancer agents whose mechanism of action may involve stress and survival signaling modulation.

Methods

Cell Culture:

Cells were grown at 37° C. in a humidified 5% $CO_2$-95% air atmosphere. MCF-7, MDA-MB-231, MDA-436, HCT116, SW480, PC3 and BJ fibroblasts (ATCC, Manassas) were maintained in Dulbecco's Modified Eagle's Medium (hereinafter DMEM) supplemented with 10% FCS. HT-29, LNCaP, DU145, PC3 and A549 cells were maintained in RPMI supplemented with 10% FCS (Sigma). MCF-10A were maintained in DMEM supplemented with 5% horse serum (Atlanta Biologicals), 20 ng/ml epidermal growth factor (EGF) (Sigma), 10 µg/ml insulin (Sigma) and 500 ng/ml hydrocortisone (Sigma).

Mammosphere Growth:

Adherent cells were gently trypsinized, (0.05% trypsin/EDTA) washed twice in PBS and filtered through a 40 µM cell sieve to obtain a single cell suspensions. Cells were diluted to a concentration of 10,000 cell/ml in serum-free phenol-red free MEBM (MEGM Bulletkit, Lonza) supplemented with 5 µg/ml bovine insulin, 20 ng/ml recombinant epidermal growth factor, 20 ng/ml basic fibroblast growth factor (Gibco), 1×B27 supplement, 0.5 µg/ml hydrocortisone (MEGM Bulletkit, Lonza). For MDA-MB-231 mammosphere cultures serum-free phenol red-free CnT-27 medium with growth additives (CellnTEC Advanced cell systems, Bern, Switzerland) was used as previously described. 0.1 ml was seeded per well of a Ultralow attachment 96 well plates. The following day the indicated doses of GR-24 (ppm) or vehicle alone (0.6% acetone f/c) were added. Media was replenished every 3-4 days. Self-renewal capacity of the mammospheres was determined by re-plating and producing further generations of mammospheres. Secondary mammospheres were cultivated by dissociation (trypsinization with gently vortexing) of 10-14 day old primary mammospheres. Single cell suspensions were obtained as described above.

Strigolactone Treatments:

The strigolactone analogs were solubilized in acetone (Sigma) at stock concentrations of 1666.67 ppm (GR-24, MEB-55, ST-362, EG-9c) and 7500 ppm (EG-5, ST-357). Cells were treated at the indicated doses by diluting the strigolactone analog to the required highest concentration in the appropriate growth medium. Serial dilutions were performed for subsequent lower concentrations. SB203580 and SP600125 were purchased from Cell Signaling Technology (Danvers, Mass.). All inhibitors were solubilized in DMSO according to the manufacturer's instructions.

Crystal Violet Growth Assays:

Cells (MDA-MB-231, MDA-MB-436 and BJ fibroblasts) were seeded at 1500 or 4000 cells per well of 96 well plates. The following day media was replaced with phenol-free DMEM supplemented with 10% charcoal-stripped FBS and the indicated doses of GR-24, Strigolactone analogs or vehicle (acetone) alone as control. At the indicated time points, individual plates were fixed and stained with crystal violet solution (0.5% crystal violet and 25% methanol) for 15 min, washed several times in distilled water and air dried overnight. Sodium citrate solution (0.1M) was used to solubilize bound crystal violet and optimal densities were measured at 560 nm (Glomax®—Multi Detection plate reader, Promega).

XTT Viability Assay:

Cells were seeded into a 96 well plates at 1500 cells per well (MCF-10, PC3, DU145, MDA-MB-231, MDA-MB-436, HT-29, SW480), 1000 cells per well (K562) or 4000 cells per well (MCF-7, HCT116) in triplicate in normal growing media (with the exception of K562, a non-adherent leukemic cell line which was seeded in phenol-free DMEM supplemented with 10% charcoal-stripped FBS). The following day media was replaced with phenol-free DMEM supplemented with 10% charcoal stripped FBS and the indicated final concentrations of strigolactone analog or vehicle (acetone) alone. Cells were incubated for 3 days, at which time XTT (2,3,-bis(2-methoxy-4-nitro-5-sulfophenyl)-5-[(phenylamino)-carbonyl]-2H-tetrazolium inner salt) reduction was used to quantify viability according to manufacturer's instruction (ATCC). Cells were incubated with XTT reagent for 2-3 hours at 37° C. in a humidified 5% $CO_2$-95% air atmosphere. Absorbance was recorded by a photometer SPEKTRAFluor Plus, Tecan (Salzburg, Austria) at 450 nm with 750 nm of reference wavelength. Cell survival was estimated from the equation: % cell survival=100×(At−Ac), where At and Ac are the absorbencies (450 nm) of the XTT colorimetric reaction (ATCC) in treated and control cultures respectively minus non-specific absorption measured at 750 nm. Absorbance of medium alone was also deducted from specific readings.

Cell Cycle Analysis:

Adherent cells were trypsinyzed, washed twice with PBS and filtered through a 40 μM cell sieve. DNA content was assessed by flow cytometry. Cells were seeded at densities of $1.5 \times 10^5$ cells (MDA-MB-231, MDA-MB-436), or $4 \times 10^5$ cells (MCF-7 and MCF10A), or $2 \times 10^5$ cells (SW480, HT-29), or $5 \times 10^5$ cells (HCT116), per well in DMEM with 10% FBS in 6-well plate culture dishes. The following day, the media was replaced with phenol-free DMEM supplemented with 10% charcoal-stripped FBS with the indicated concentrations of GR-24 or vehicle alone (acetone). After 48 hours, cells were washed twice with PBS (pH 7.4), centrifuged at 360 g for 10 minutes at 4° C., and fixed in chilled ethanol (70%; v/v in PBS) with gentle vortex mixing. To determine their DNA contents, the cells were stained with 40 μg/ml propidium iodide (hereinafter PI) and analyzed using a FACSCalibur flow cytometer and CellQuest analysis software (Becton Dickinson, San Jose, Calif.). Where phospho-Histone-H3 staining was carried out, cells were incubated with polyclonal antibody against phosphoHistone H3 and then with secondary Goat anti-rabbit IgG-conjugated to FITC prior to PI staining.

AnnexinV Staining

Cells were cultured for 48 hours under the same conditions as those used for the DNA content/cell cycle analysis. All the cells were collected and resuspended in 100 μl 1× Annexin V Binding Buffer (BD Biosciences, San Jose, Calif., USA). 2 μl FITC-Annexin V (BD Biosciences) was added and incubated for 10 min in the dark (room temperature). Cells were then stained with PI (Sigma, Saint Louis, Mo., USA) to a final concentration of 5 μg/ml and the cells were incubated at room temperature for 15 min in the dark. Then, 400 μl of Annexin V binding buffer were added and flow cytometry was performed using a BD FACSCalibur flow cytometer. Cells were considered to be apoptotic if they were Annexin V+/PI− (early apoptotic) and Annexin V+/PI+ (late apoptotic). Each analysis was performed using at least 20,000 events.

Aldeflour Expression:

MCF-7 mammospheres were trypsinized, gently vortexed and passed through a 40 uM cell filter to produce single cell suspensions. Cells ($5 \times 10^5$) were washed and re-suspended in growth media (Lonza). To identify the Aldefluor-stained cell population with ALDH1 enzymatic activity, the Aldefluor kit (Stem Cell Technologies), which is designed for optimal identification and isolation of stem cells through specific interaction with human ALDH1 was used. Briefly, cells were suspended in Aldefluor assay buffer containing uncharged ALDH1-substrate, BODIPY-aminoacetaldehyde (BAAA), and incubated for 45 min at 37° C., with gently vortexing every 15 min. BAAA is taken up by living cells through passive diffusion and then converted by intracellular ALDH into a negatively charged reaction product BODIPY-aminoacetate, which is retained inside cells expressing high levels of ALDH1, causing the cells to become brightly fluorescent. Fluorescent ALDH1-expressing cells were detected in the green fluorescence channel (520-540 nm) of a FACScan instrument (BD Biosciences). A set of cells were stained using the identical conditions with the specific ALDH inhibitor, diethylaminobenzaldehyde (DEAB), to serve as a negative control for the experiment. PI (Sigma) fluorescence was detected using the orange fluorescence channel. Cells incubated with BAAA and DEAB were used to establish the baseline fluorescence of cells and ALDH1-positive fraction. Data were analyzed by using Cell Quest software (BD Biosciences).

Immuno-Blotting:

Cell lysates were prepared using a lysis buffer containing: 50 mM Tris-HCl (pH 7.5), 125 mM NaCl, 0.5% NP-40, 0.1% SDS, 0.25% sodium deoxycholate, 1 mM EDTA, 50 mM NaF, 1 mM sodium orthovanadate, 2.5 mM sodium pyrophosphate, 1 mM sodium β-glycerophosphate, 1 mM PMSF, and a protease inhibitor cocktail (Roche Molecular Biochemicals) and cleared by centrifugation. Protein concentration was determined using the BCA Protein Assay (Pierce), and 20-50 μg of lysate were separated in a 4-12% SDS-PAGE gel. After transfer, membranes were blocked for 15-30 min at room temperature in 5% BSA (Sigma) in Tris-buffered saline containing 0.1% Tween-20. Primary antibody was incubated for either 1.5 hours at room temperature or overnight at 4° C. Secondary antibody was incubated for 30-45 min at room temperature, and proteins were visualized with West Pico Stable (Pierce). All antibodies were used at 1:1000 dilution unless otherwise stated. pT308AKT, AKT, pT180/Y182, pT183/Y185 P38MAPK, pP38MAPK, pT202/Y204 pERK1/2, ERK1, pT183/Y185, pJNK1/2, JNK1, pT71ATF2, pT581MSK1, pT14 Cdc2, Cdc2, pT68Chk2 (cell signaling), pT334MAPKAPK, pS82HSP27 (Cell Signaling Technology, Danvers, Mass.), α-tubulin (Biomarkers, 1:50,000), Cyclin B1 (Santa Cruz Biotechnologies) and horseradish peroxidase-conjugated anti-rabbit IgG and anti-mouse IgG (1:5,000, Pierce).

Immunoblot Quantification

Densitometric quantifications were carried out using ImageJ software (NIMH).

Results

GR-24 Inhibits the Growth of Human Breast Cancer Cell Lines

The effect of GR-24 (FIG. 3) on long-term cancer cell line growth was assessed by crystal violet assay. MCF-7 (estrogen receptor positive (ER+), tumorigenic, nonmetastatic), (A) MDA-MB-231, MDA-MB-436 (ER negative (−), metastatic) and BJ fibroblasts (normal, non-neoplastic line) were treated with GR-24 at a dose range of 0.5 to 10 ppm (1.65-33 μM). Growth was monitored for up to 10 days. At the indicated time points, plates were stained with crystal violet. Data are reported as the Percent Absorbance (560 nm) of vehicle control. Average±standard deviations (SD). Student's t-test (2-tailed, paired) was used to evaluate GR-24 treated groups with vehicle (control) groups at final time point and regarded as being significant if $p<0.05$ (*), very significant if $p<0.01$ (), extremely significant if $p<0.001$ (*). (B) Is a graph showing the light absorbance reading (560 nm) after 7 days exposure to the indicated doses of GR-24. Data expressed as a percentage of vehicle controls. Average of triplicate samples+SD. Horizontal line (---) marks 50% reduction in Absorbance (560 nm) relative to vehicle controls. The Table on the right shows inhibitory concentrations required for 50% reduction in growth after 7 days ($IC_{50}/72d$), and calculated by performing linear regression with interpolation between relevant y-axis data points (GraphPad Prism Software).

Figure 3B:
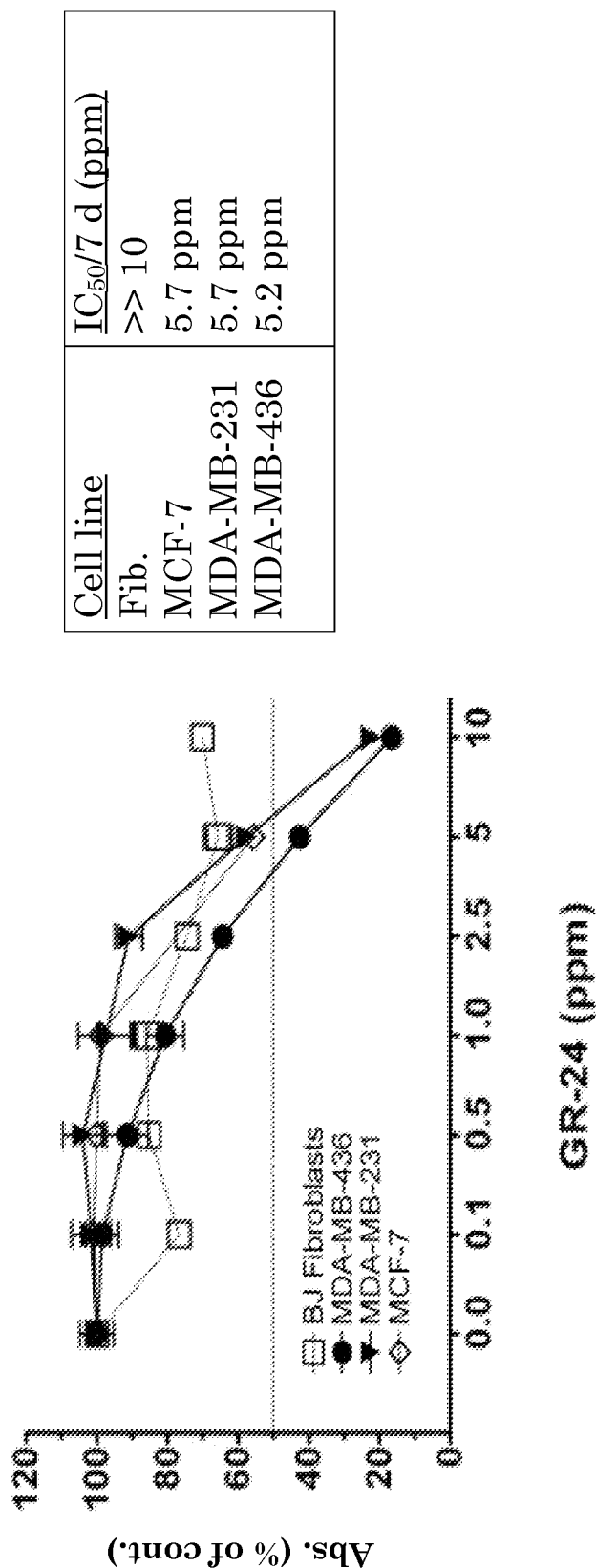

Concentrations of 2.5-5 ppm of GR-24 resulted in a significant reduction in growth compared to vehicle treated controls in MCF-7, MDA-MB-231 and MDA-MB-436. BJ fibroblasts showed no significant reduction in growth over this time period (FIG. 3). A small reduction was observed at the highest concentration (10 ppm), however this was minor when compared to the growth inhibition achieved by the same concentration of GR-24 in MCF-7 and MDA-MB-231 cells. To determine the concentration of GR-24 at which 50% of long-term proliferation was inhibited ($IC_{50}$) after 7 days, optical densities at day 7 were plotted as a percentage of vehicle controls (FIG. 3B) and concentrations were calculated by interpolation. $IC_{50}$ concentrations for MDA-MB-436, MDA-MB-231 and MCF-7 cells were 5.2 ppm (17.2 µM), 5.7 ppm (18.8 µM) and 5.7 ppm (18.8 µM) respectively (FIG. 3B).

GR-24 Induces G2/M-arrest and Apoptosis

To investigate the effect of GR-24 on cell cycle progression, total DNA content analyses were carried out by propidium iodide staining using flow cytometry. MCF-7, MDA-MB-231 and MDA-MB-436 cells were treated with 5 and 10 ppm of GR-24 for 48 hours and the non tumorigenic breast cell line MCF10A was used as a control. GR-24 treatment causes a dose dependent increase in the percentage of cells in G2/M phase and a concomitant decrease in the percentage of cells in G1 phase in all tumorigenic cell lines but no change was observed in the cell cycle distribution of MCF10A cells upon GR-24 treatment (FIG. 4). At higher concentrations (10 ppm), GR-24 caused an increase in the sub-G1/apoptotic fraction of MDA-MB-231 (4.6 fold) and MDA-MB-436 cells (3.4 fold) compared to vehicle controls, indicating increased apoptosis. MCF-7 cells showed no change in the subG1 fraction at 10 ppm (FIG. 4).

GR-24 Inhibits the Growth and Reduces Viability of Breast Cancer Stem-like Cell Enriched Mammosphere Cultures Tumor Initiating Cells (TICs) or Cancer Stem Cells (CSCs) are intrinsically resistant to conventional chemo- and radiation-therapies. These cells are able to regenerate the cellular components of the original tumor eradicated by such treatments, and ultimately lead to recurrence. The ability to target this cell population is important to develop effective treatment regimes. Mammosphere culture has been used widely for the enrichment of breast CSCs. MCF-7 cells can be propagated as 'mammospheres' under non-adherent, serum-free growing conditions. To determine if GR-24 could inhibit MCF-7 mammosphere formation, MCF-7 cells were grown as mammospheres in the presence or absence of GR-24 (FIG. 5A). Mammosphere formation was completely inhibited in the presence of 2.5-5 ppm of GR-24, and severely attenuated at 1 ppm, (p<0.01), 5 fold below the concentration required to inhibit monolayer growth (FIG. 5). At 0.5 ppm concentrations, growth was inhibited to a lesser degree however mammospheres were often smaller (<50 uM) than vehicle treated controls (p<0.05). Similar results were obtained when secondary MCF-7 mammospheres were grown in the presence of GR-24 (FIG. 5B). To assess the generality in mammosphere growth inhibition by GR-24, another breast cancer cells line, MDA-MB-231, was tested (FIG. 5C). At 5 ppm, GR-24 completely blocked MDA-MB-231 mammosphere formation. At 2.5 ppm, mammopheres growth was severely attenuated, with mammospheres being substantially smaller (<50 uM) compared to vehicle control groups. Importantly, the concentrations of GR-24 necessary to block MCF-7 and MDA-MB-231 mammosphere formation were 5.7 and 2.7 fold lower respectively than the $IC_{50}$ doses for monolayer growth. Mammospheres therefore exhibit a greater sensitivity to the growth inhibitory effects of GR-24 versus monolayer culture. This is an interesting finding since mammosphere cultures reportedly are enriched with TICs and those have been shown to be inherently resistant to chemotherapy.

Effect of GR-24 on Mammosphere Viability and Stem Cells Marker Expression

Mammosphere viability was assessed by XTT assay (ATCC). 5 days after addition of the indicated concentrations of GR-24, cell viability was determined. At 5 ppm, GR-24 reduced viability by approximately 80% (98.4%+3.4 to 16.4%+4.6) (FIG. 6A). Interestingly at 2.5 ppm where mammosphere formation is completely inhibited, viability remains at 68.6%+12.4, suggesting that timing of inhibition is critical. To further investigate GR-24 induced inhibition of mammosphere formation, the expression of breast stem cells markers were examined.

Aldehyde Dehydrogenase (ALDH1) has been shown to be a functional marker in the isolation of TICs in many cancer types and MCF-7 TICs can be selected on the basis of their ALDH activity in combination with other surface markers. ALDH activity was enriched in primary mammosphere relative to adherent culture and secondary mammosphere culture reached further enrichment (FIG. 6B): Adherent MCF-7 cells and 8 days old secondary mammospheres were prepared as single cells suspensions and ALDH expression was analyzed according to manufacturer's instructions (Aldefluor kit, Stem Cell echnologies, Vancouver, Calif.): the right graph shows the percentage of ALDH positive cells in either adherent MCF-7 cultures, primary (Adh), primary mammospheres grown in the presence of either 5 ppm, 1 ppm GR-24 or vehicle alone (cont.) (0.6% Acetone) and 8 day old secondary mammospheres (sec.). Secondary mammospheres exhibit a 2.4 fold enrichment for ALDH activity. Primary mammospheres exhibit an small increase of 6% to 8% positivity for ALDH expression. GR-24 treatment causes a reduction in ALDH expression from 6% to 2%. This data suggests that GR-24 is a potent inhibitor of mammosphere formation and down-regulation of ALDH by GR-24 may account for this activity. Furthermore, this data suggests that strigolactones are a potent inhibitor of mammosphere formation.

Strigolactone Analogs are Effective Growth Inhibitors of a Diverse Range of Cancer Derived Cell Lines An additional five synthetic strigolactone analogs were obtained (FIG. 16) and tested for their ability to inhibit the growth of colon, prostate, lung, osteosarcoma, melanoma and leukemia cancer derived cell lines. MCF-10A cells were included as an example of a non-tumorigenic line. XTT viability assays were carried out in the presence of the indicated doses of strigolactone analogs following 3 days of treatment. Resulting differences in absorbance readings following strigolactone analogs treatment reflect changes in proliferation and cell survival (FIG. 7A-C): Cells were seeded into 96 well plates in normal growing media. The following day media was replaced with phenol-free DMEM supplemented with 10% charcoal-stripped serum and the indicated doses of strigolactone analog or vehicle (cont.) alone. Viability was assayed after 3 days (XTT, ATCC). $IC_{50}$ concentrations are indicated (Table 3 above). Cell lines exhibited substantial variation in their response to each strigolactone analog, however growth of all cancer cell lines was inhibited by strigolactone analogs treatment. ST-362 and MEB-55 were the most potent strigolactone analogs. $IC_{50}$ concentrations of ST-362 started as low as 2.9 ppm (MDA-MB-231) and for MEB-55, as low as 3.9 ppm (MDA-MB-231). The non-tumor cell line, MCF10A, was resistant to the effects of strigolactone analog treatment up to a concentration of 15 ppm, with the exception of ST-362, which caused a 20% reduction in viability between day 10 and 14. EG-9C was the least effective strigolactone analog in all cell lines tested ($IC_{50}$>10-15 ppm), with the exception of A549 wherein a value of $IC_{50=4.3}$ ppm was measured. A549 cells also show sensitivity to EG-5, MEB-55, ST-357 and ST-362, at $IC_{50=4.8}$-6.5 ppm. ST-357 was a potent growth inhibitor of PC3 ($IC_{50=5.3}$ ppm) and MDA-MB-231 ($IC_{50=5.0}$ ppm) cells. Some cell lines exhibited increased XTT absorbance at lower dose concentrations. Vehicle volumes in controls were matched with those in the highest dose only and total vehicle volumes were not matched for lower doses. Sensitivity to vehicle levels probably accounts for the suppressed viability observed in controls in relation to the lower doses in some cell lines.

TABLE 4

IC$_{50}$ concentrations of strigolactone analogs in cancer cells lines

| Tumor Cell Lines | IC$_{50}$ (ppm) at 72 hours | | | | |
|---|---|---|---|---|---|
| | EG-5 | EG-9C | ST-357 | ST-362 | MEB-55 |
| Breast | | | | | |
| MCF10A | >15 | >15 | >15 | >15 | >15 |
| MCF-7 | 17.5 | 17.3 | >20 | 8.1 | >12.8 |
| T47D | 8.8 | >10 | >10 | 8.6 | 5.0 |
| MDA-MB-231 | 7.5 | >10 | 5.0 | 2.9 | 3.9 |
| MDA-MB-436 | ND | >10 | ND | 5.9 | 8.3 |

Inhibitory concentrations required to achieve 50% inhibition (IC$_{50}$) in viability after 3 days of strigolactone analogs treatment. Values were calculated by linear interpolation (Graphpad Prism 4.0).

To assess strigolactone analogs stability in aqueous solution, each strigolactone analog was diluted to the desired concentration in media and stored at 4° C. for 3 days, at which time the strigolactone analog containing media was overlayed onto MCF-7 cells seeded into 96 well plates in phenol free DMEM supplemented with 5% charcoal stripped serum. After 3 days growth and viability was assessed (XTT, ATCC) and results compared to cells treated with freshly diluted strigolactone analog (FIG. 15) (absorbance readings presented as % of controls. Average+SD). All strigolactone analogs retained similar levels of activity over this time period, with the exception of EG-5 which completely failed to inhibit MCF-7 growth. For this reason all strigolactone analogs were diluted fresh from acetone stocks into media to desired concentrations and overlayed onto cells within 1 hour. Where necessary, media was refreshed every 3 days.

Strigolactone Analogs Inhibit Cell Cycle Progression and Induce Apoptosis

GR-24 treatment causes an increase in the percentage of MCF-7, HCT116, MDA-MB-231, DU145, A549, SW480 and HT-29 cells in G2/M-phase and apoptosis in MDA-MB-231, MDA-MB-436 and HCT116 cells. To determine whether these additional strigolactone analogs also induce a similar mechanism of growth inhibition, cell cycle analysis was carried out. Results show a dose dependent increase in the percentage of cells in G2/M phase (FIG. 12): Cells were treated for 48 hours with different concentrations of strigolactone analogs in phenol free-DMEM supplemented with 10% charcoal stripped serum and strigolactone analog at either IC$_{50}$/72 h or ~IC$_{50}$/72 h+25% concentrations. At concentrations 25% above the IC$_{50}$/72 h, there was evidence of increased apoptosis in MDA-MB-231 cells with increased percentages of cells in the subG1 fraction. MCF-7 cells were less sensitive to the effects of strigolactone analogs at the doses tested. BJ fibroblasts were not sensitive to the effects of strigolactone analogs at the doses tests (Table 4 above).

Figure 12A:
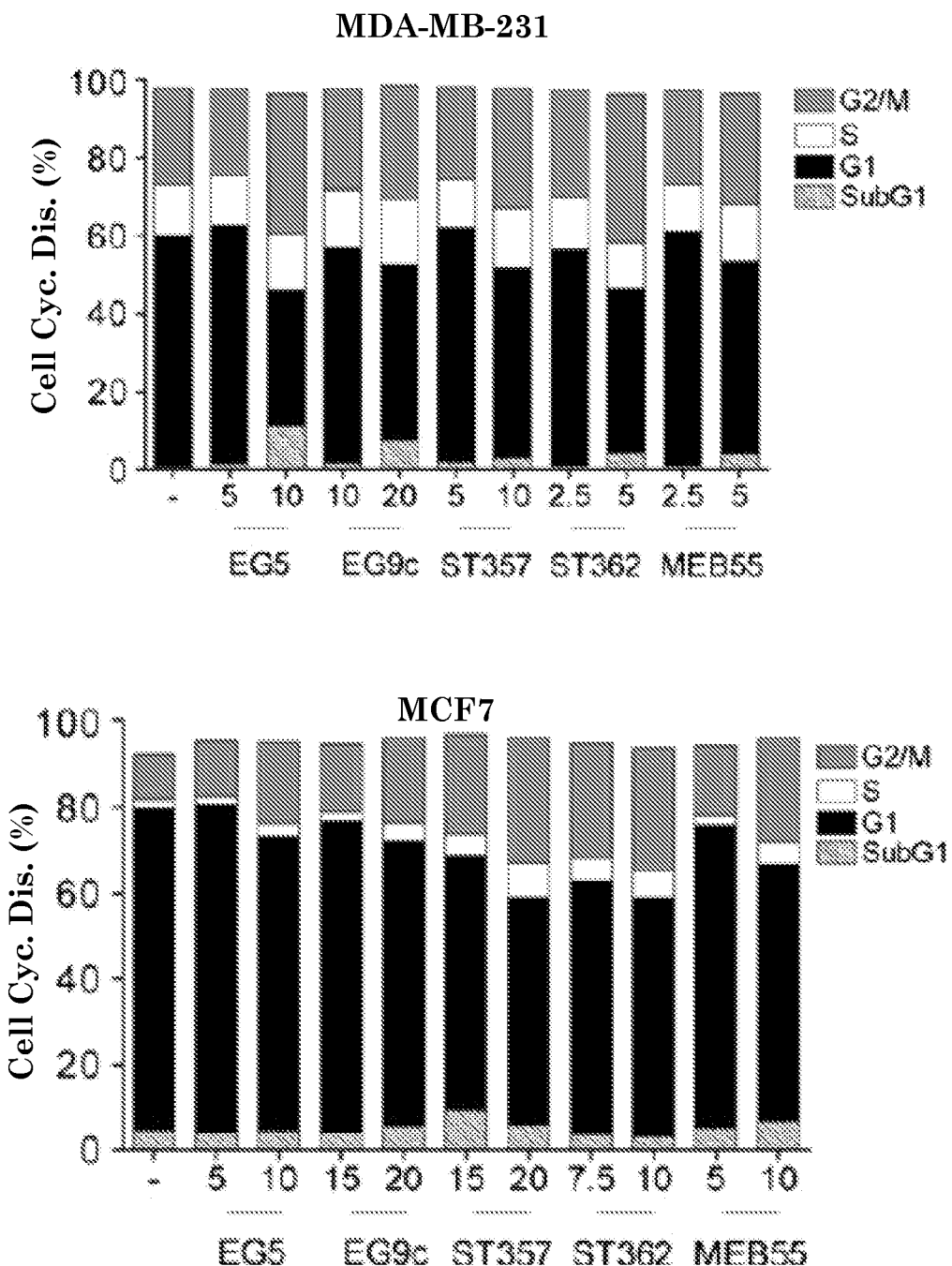
Figure 12B:
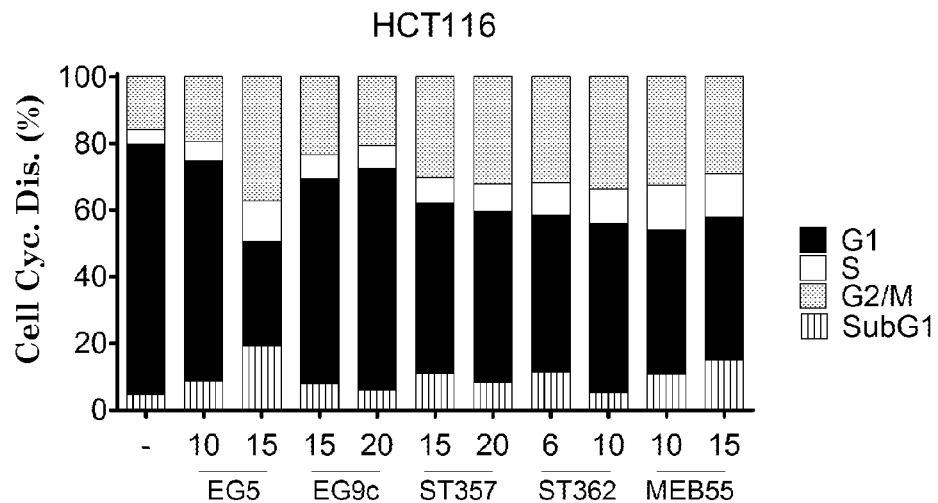
Figure 12C:
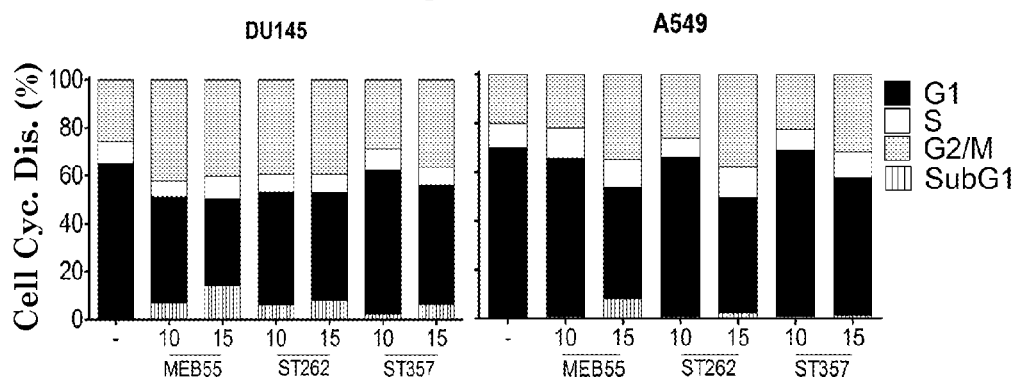
Figure 12C:
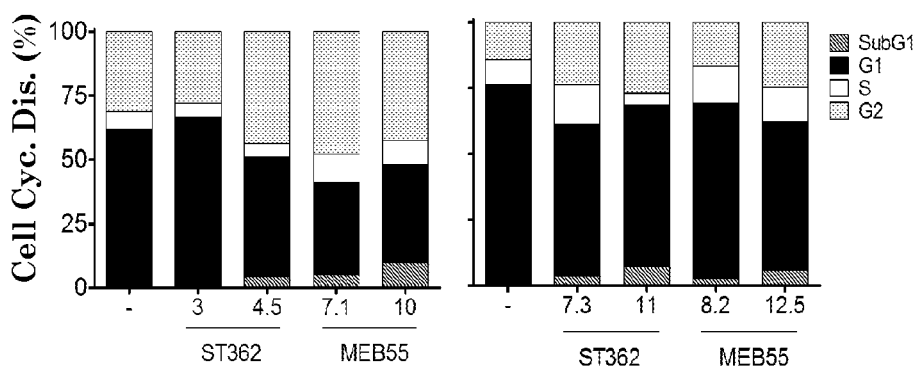
Figure 12D:
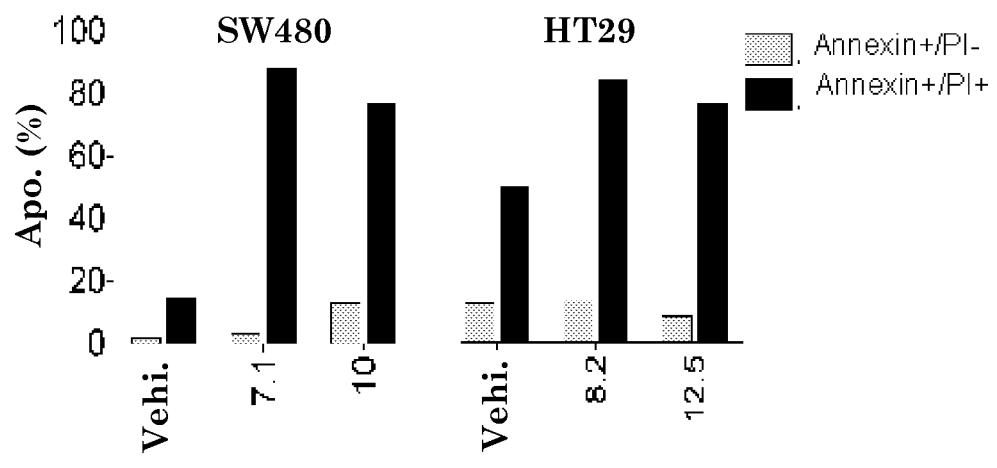
Figure 12E:
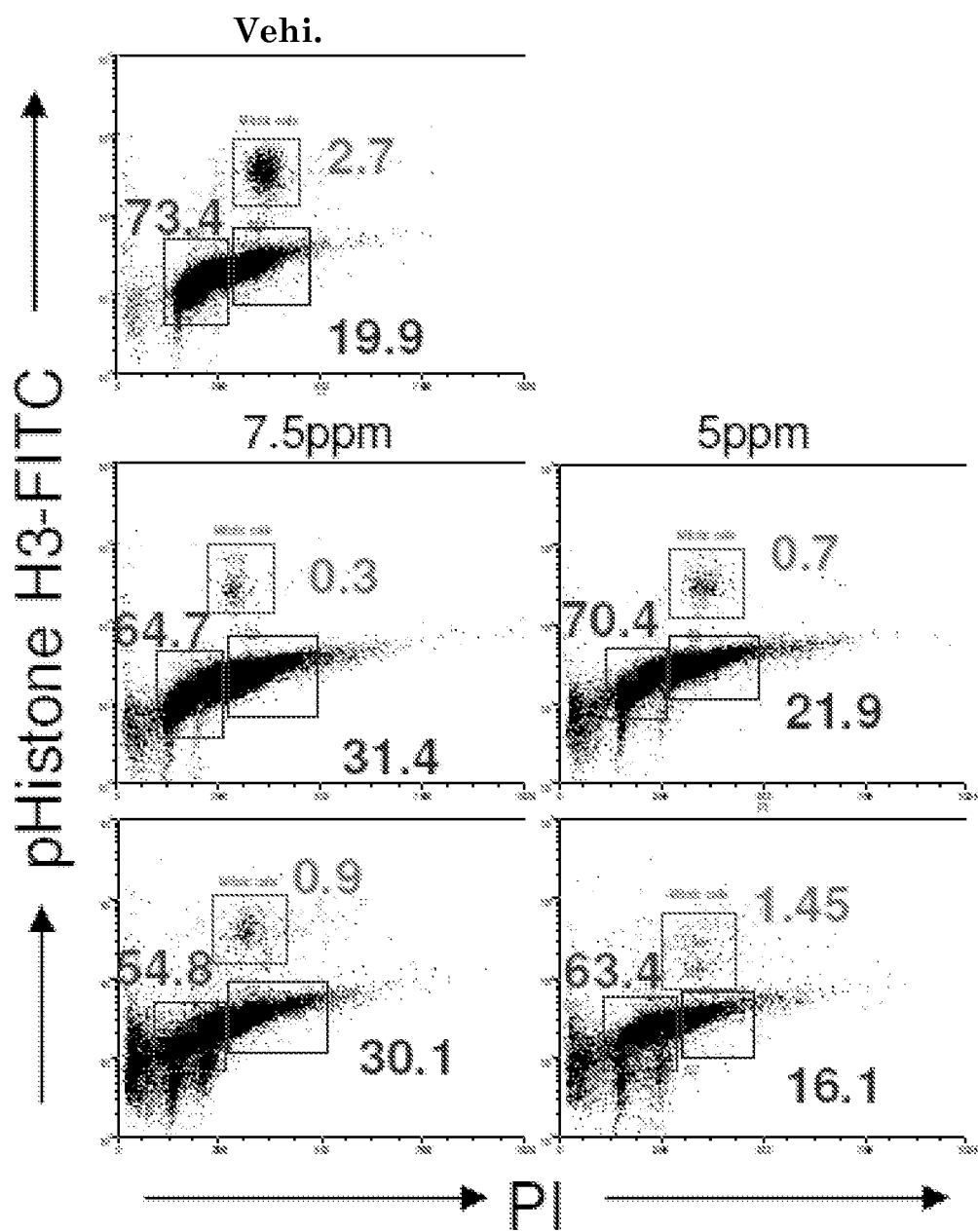
Figure 12F:
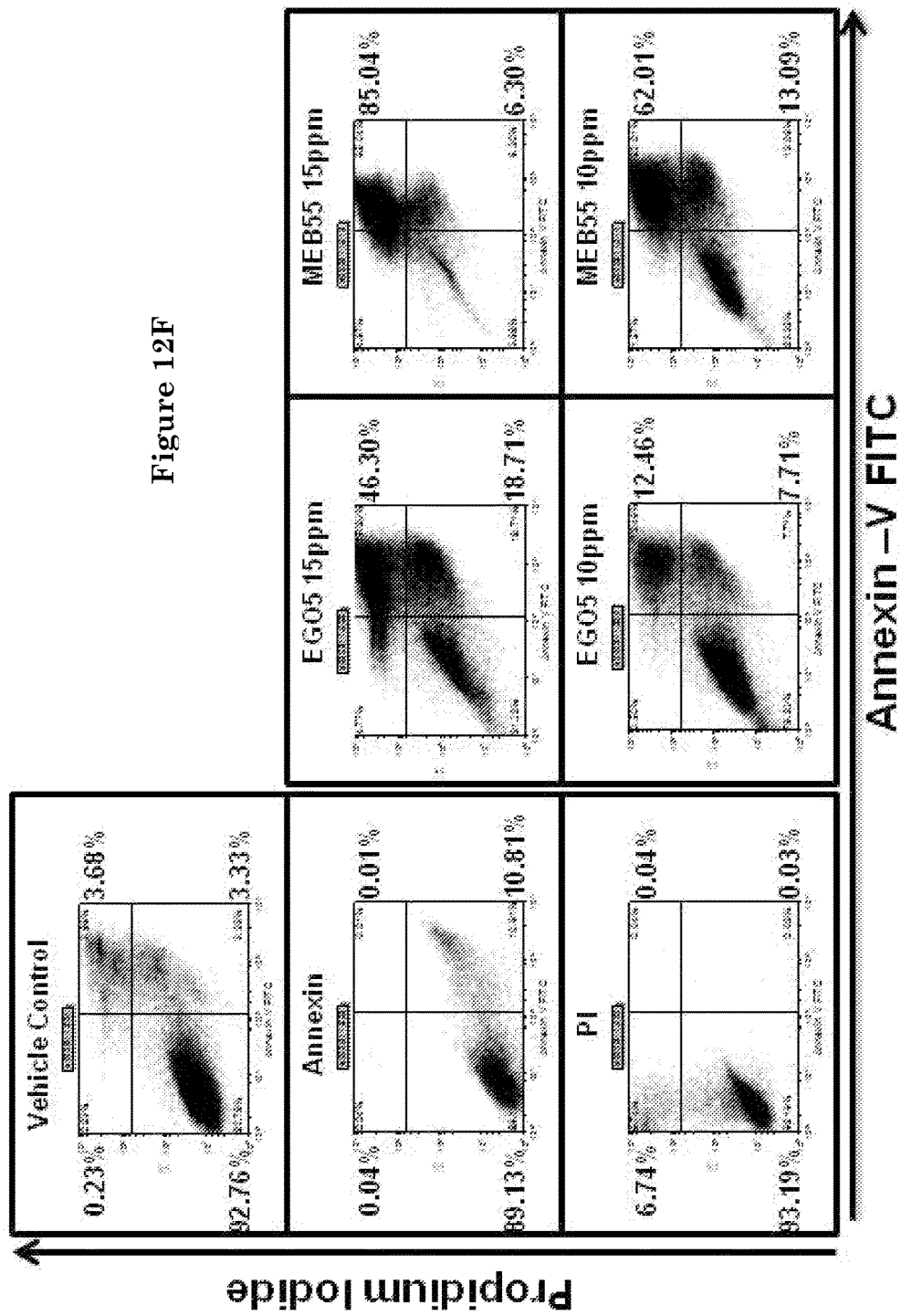
Figure 12G:
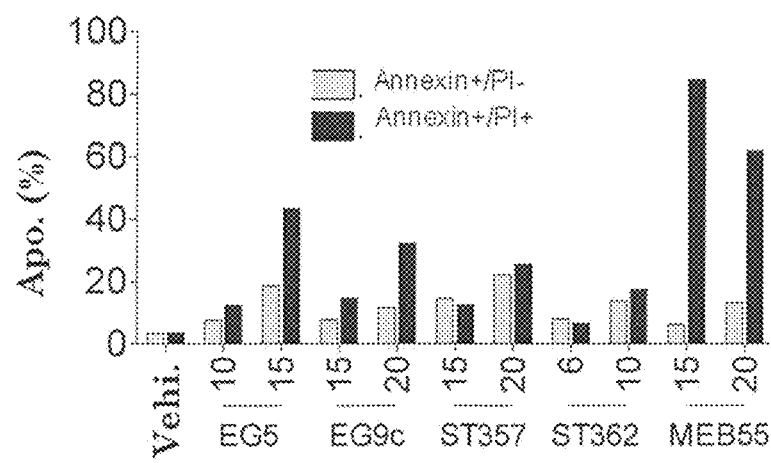

Chromosome condensation at mitosis is accompanied by phosphorylation of histone H3. Accordingly, in order to determine if cells were arresting at G2 or M phase, HCT116 cells were analyzed for pS10 Histone H3 following strigolactone analogs exposure. Results (FIG. 12E) show that there was a dose-dependent decrease in the percentage of cells staining positive for pHistone H3 following strigolactone treatment (2.7% in vehicle controls and 0.3% and 0.7% in cells treated with 7.5 ppm and 5 ppm ST-357 respectively and 0.9% and 1.45% in cells treated with 7.5 ppm and 5 ppm MEB-55 treatment respectively) indicating of a reduction in the distribution of cells in M-phase (FIG. 12E). To further quantify whether the growth inhibition observed in-vitro following strigolactone treatment was due in part to apoptosis, HCT116 cells were dual stained with Annexin V and PI (Prodidium Iodide). Annexin V staining indicate the inversion of the inner leaflet of the plasma membrane an early event of apoptosis. Late apoptosis is characterized by loss of membrane integrity and cells become permeable to PI. As shown in FIG. 12F, strigolactone analogs treatment of HCT116 cells increased the percentage of early (Annexin V+/PI−) and late (Annexin V+/PI+) apoptotic cells in a dose dependent manner: HCT116 cells were seeded out at 4×10$^5$ cells per well into two 6-well plates in 10% DMEM media. The following day the media was replaced with phenol-red free DMEM supplemented with 10% charcoal stripped serum and the indicated strigolactone analog. The doses used represent the IC$_{50}$ and IC$_{50}$+25%. Cells were incubated for 48 hours and then co-stained with annexin-V and PI (FIG. 12F). Following treatment with 10 ppm and 15 ppm MEB-55, the percentage of late apoptotic cell increased from 3.6% to 62% and 85% respectively (FIG. 12F, lower panel). Following 10 ppm and 15 ppm EG-9c treatment the fraction of late apoptotic cells increased to 12.5% and 43.3% respectively (FIG. 12F, middle panel). This data is also presented in the form of a bar graph (FIG. 12G), together with results for the other strigolactone analogs, EG-5, ST-357 and ST-362. Dual Annexin V/PI staining analysis was also carried out on two other colon cancer cell lines, (SW480, HT29) following strigolactone treatment. Increased apoptosis was also observed in these lines following MEB-55 treatment in a dose dependent manner (FIG. 12D).

Figure 9A:
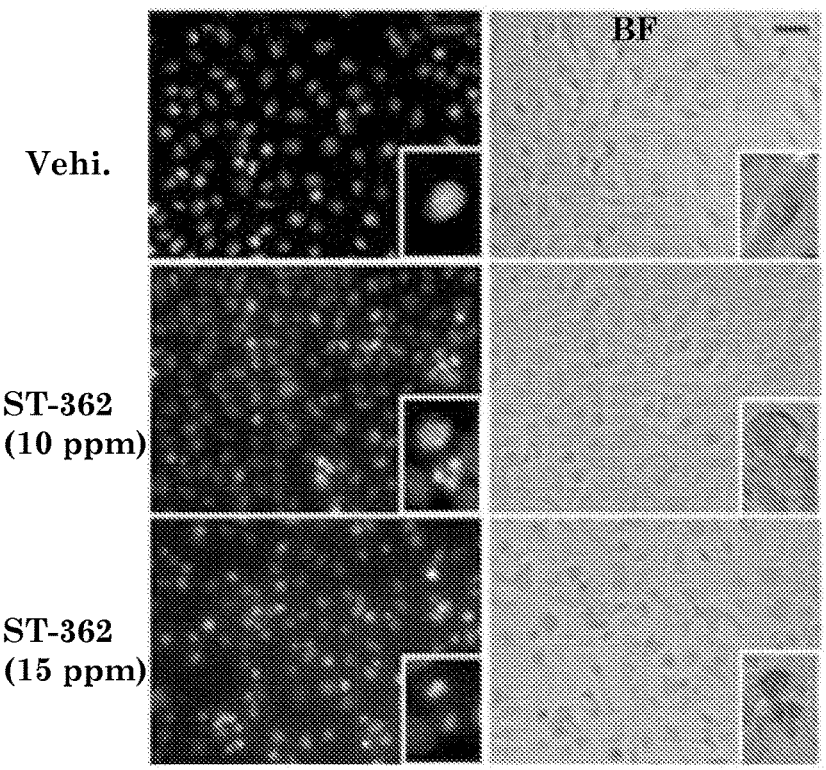
Figure 9B:
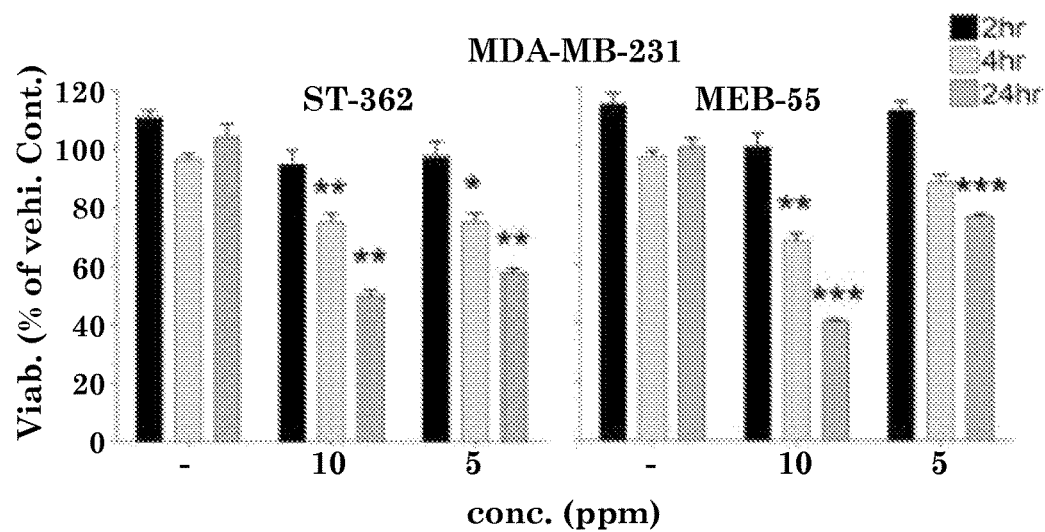
Figure 9C:
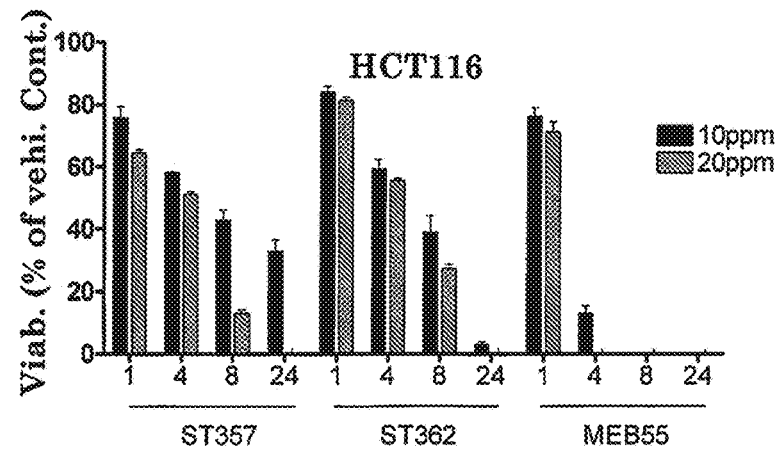

Hoechst staining was used to analyze changes in the nucleus. ST-362 treatment at 5-10 ppm resulted in increased nuclear condensation and fragmentation changes indicative of apoptosis (FIG. 9A). To determine if continual strigolactone analog exposure is required for growth inhibition and reduced cell survival, MDA-MB-231, HCT116 and U20S cells were treated with either ST-357, ST-362 or MEB-55 at 5 ppm, 10 ppm or 20 ppm for 1, 2, 4, 8 or 24 hours. At each time point the strigolactone analog was removed and the media was replaced with fresh growth media without strigolactone analog. The cells were then fixed in 1% paraformaldehyde and stained with Hoechst33342, showing evidence of cell shrinkage, nuclear condensation and nuclear fragmentation is observed, as well as eccentric nuclei, (insert in FIG. 9A). In addition, viability of MDA-MB-231 cells was assessed after 24 hours by using an XTT assay (FIG. 9B). ST-362 and MEB-55 induce a non-reversible reduction in cell viability in a dose-dependent and incubation time dependent manner: MDA-MB-231 breast cancer cells were treated with the indicated concentrations of strigolactone analog (FIG. 9B). After 2, 4 or 24 hours the media was removed, cells were washed and media was replaced with growth media minus strigolactone analog. Cell viability was assessed at 24 hours: A significant decrease in viability was induced as early as 4 hours of strigolactone analog treatment ($p<0.01$). No changes in cell viability were observed after a 2 hours exposure. Continual exposure (24 hours) to each strigolactone analog induced a greater reduction in cell viability ($p<0.001$) compared to 4 hours exposure. These results indicate that strigolactone analogs induce non-reversible and time dependent decreases in cell viability. Therefore, it can be concluded that strigolactones also induce non-reversible and time dependent decreases in cell viability.

Figure 9D:
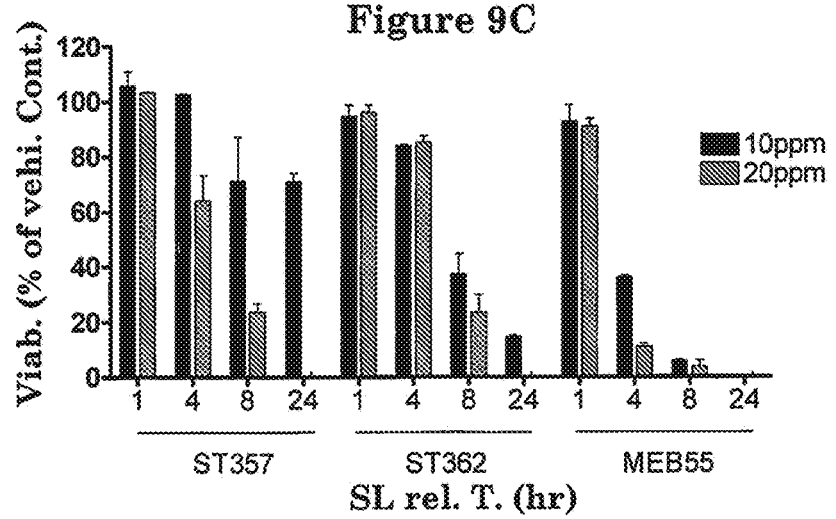
Figure 9E:
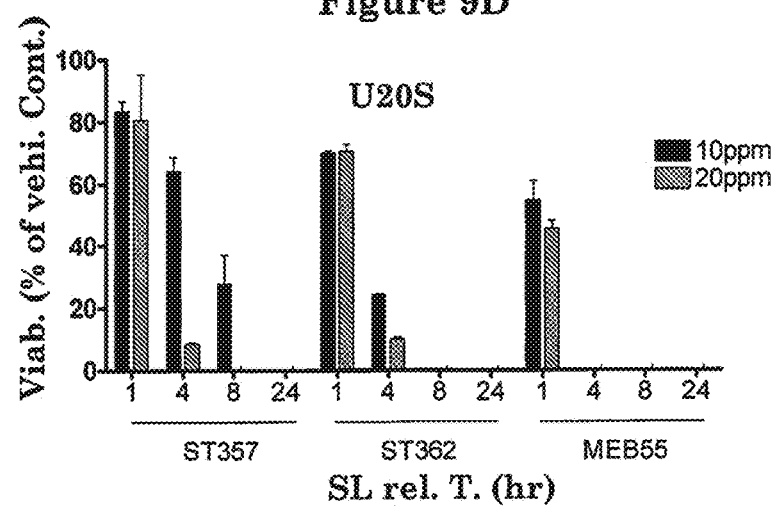

In HCT116 cells (FIG. 9C), ST357, ST362 and MEB55 produced a modest decrease in viability after 1 hour (10 ppm; 75%, 82% and 75%, 20 ppm; 63%, 80%, and 68%, respectively). After 4 and 8 hours of treatment, ST-362 (20 ppm) reduced cell viability from 60% to 30%. ST-357 decreased viability from 50% to 10%. MEB-55 was the most potent analog tested, producing a dramatic decrease in viability at 4 hours (10 ppm, 18% and 20 ppm, 0%). Similar results were observed in DU145 cells (FIG. 9D). U2OS cells exhibited a greater sensitivity to strigolactone analogs treatment between 1 and 4 hours (FIG. 9E), which correlates with the lower $IC_{50}$ values in this cell line (the Table in FIG. 7). After 1 hour, viability was decreased from 80%, 65% and 52% in ST-357, ST-362 and MEB-55 treated cells at 10 ppm concentrations, and to 77%, 65% and 40% at 20 ppm concentrations, respectively. However after 4 hours, viability was reduced from 62%, 25% and 0% in ST-357, ST-362 and MEB-55 treated cells at 10 ppm concentrations and 10%, 11% and 0% at 20 ppm concentrations, respectively. These results show that the damaging effects of strigolactone treatment are induced after short exposure times and are non-reversible upon strigolactone removal.

TABLE 5

Cell Cycle Analysis of cell lines treated with strigolactone analogs

| Cell Line | Strigolactone analog (dose/ppm) | SubG1/ Apoptosis | Cell Cycle Distribution (%) | | |
|---|---|---|---|---|---|
| | | | G1 | S | G2 |
| BJ fibroblast | Vehicle | 0.21 | 84.25 | 2.510 | 10.17 |
| | EG-5 (10) | 0.49 | 82.29 | 4.480 | 10.50 |
| | ST-362 (5) | 0.72 | 83.42 | 1.580 | 12.86 |
| | MEB-55 (5) | 0.57 | 78.96 | 5.930 | 11.54 |
| MDA-MB-231 | Vehicle | 0.41 | 60.43 | 13.02 | 24.08 |
| | EG-5 (10) | 11.32 | 34.74 | 14.59 | 35.70 |
| | ST-362 (5) | 4.17 | 42.17 | 11.90 | 37.93 |
| | MEB-55 (5) | 3.88 | 49.61 | 14.51 | 28.33 |

Effect of strigolactone analog treatment on cell cycle progression of BJ fibroblasts and MDA-MB-231 cells. Flow cytometry analysis of total DNA content was used to evaluate the number of cells in different phases of the cell cycle, including subG1 peak detection following strigolactone analogs treatment. Cells were treated with the indicated doses of EG-5, ST-362 and MEB-55 for 48 hours. Data is representative of two independent experiments.

MCF-7 Mammosphere Growth is Inhibited by Strigolactone Treatment

Given the similar effects the other strigolactone analogs had on breast cancer cell line growth compared to GR-24, we anticipated that the strigolactone analogs would also have similar effects on MCF-7 primary mammosphere formation (FIG. 10): MCF-7 cells were seeded in MEBM media into low attachment, 96 well plates in duplicate at 3000 cells per well. The same day the indicated doses of strigolactone analogs were added. After 7 days representative images were taken. All five strigolactone analogs completely block mammosphere formation at concentrations of 5 ppm and above (FIG. 10A). ST-362 and MEB-55 also block mammosphere growth at 2.5 ppm. ST-357 shows a significant reduction in mammosphere growth at 2.5 ppm (p<0.01). ST-357, ST-362 and MEB-55 also significantly inhibit mammosphere formation at 1 ppm (p<0.01). These data are consistent with these strigolactone analogs being the most potent inhibitors of MCF-7 monolayer growth (FIG. 7, Table 2). Like GR-24, the doses required to inhibit mammosphere formation are lower than that required to inhibit proliferation in monolayer cultures (5 fold lower; ST-362 and MEB-55, 3 fold lower; ST-357). To determine if the sensitivity to strigolactone analogs treatments was specific to mammosphere formation or whether it extended to the integrity and survival of mature mammospheres, MCF-7 mammospheres were grown in the absence of strigolactone analogs and after 7 days (or once mammospheres had reached a mean diameter of over 100 uM), strigolactone analogs were added to the growth media (FIG. 10) at the indicated doses. MCF-7 cells were seeded in MEBM media into low attachment, 96 well plates in duplicate at 3000 cells per well and primary mammospheres left to grow for 7 days. At which time the indicated doses of strigolactone analogs were added to the media. FIG. 11A is a representative image of mammospheres treated with 5 ppm concentrations, showing dissociation after 2 days of exposure to strigolactone analogs. Mammospheres treated with EG-9C showed a less dramatic morphological change, which correlates with the reduced potency of this strigolactone analog to inhibit mammosphere formation (FIG. 11A). Following 5 days of treatment, mammospheres were monitored visually after 24 and 48 hours. No changes were observed following 24 hours of strigolactone analogs treatment. After 48 hours, mammospheres treated with ST-362, ST-357 and MEB-55, at doses of 5 and 2.5 ppm, exhibited a looser morphology and appeared to be dissociating (FIG. 11B): mammosphere numbers (>100 μM) were counted and data presented as percentage of vehicle treated control (FIG. 11B). At 5 ppm concentrations EG-5, EG-9C, ST-357, ST-362 and MEB-55 reduce mammosphere numbers from 86.7+6.8 (vehicle control) to 23+5, 38+6.2, 6+2, 8.3+3.5 and 9.3+1.5%, respectively. At 2.5 ppm concentrations, mammosphere numbers were reduced to 35+6.9 (EG-5), 52+12.3 (EG-9C), 22+8.5 (ST-357), 6+1.7 (ST-362) and 20.7+8.6 (MEB-55). As expected, these results correlate closely with the analogs ability to inhibit mammosphere formation (FIG. 5). XTT viability assays were also carried out on dissociated mammospheres. At concentrations of 5 ppm, EG-5, ST-362 and MEB-55 reduced viability to 3.7+0.5, 25.5+8.8 and 4.6+1.1% respectively.

Strigolactone Analogs Activate Stress-activated MAPKs and Inhibit Survival Signaling To investigate the signaling mechanisms elicited by strigolactone analogs in cancer cells, MDA-MB-231, DU145 and HCT116 cells were treated with strigolactone analogs for 1, 4 or 8 hours and lysates were analyzed by immuno-blotting. The family of MAPK enzymes plays a pivotal role in cell growth, survival and cellular stress responses. The best characterized MAPKs fall into three families: (i) the mitogen activated extracellular signal regulated kinases (ERK1/2) which are activated in response to positive proliferation signals, (ii) c-Jun amino (N)-terminal kinases (JNK1/2/3) and (iii) p38 isoforms (p38α, β, γ, δ), all are activated by environmental stress stimuli such as DNA damage, UV irradiation and inflammatory cytokines.

Figure 13A:
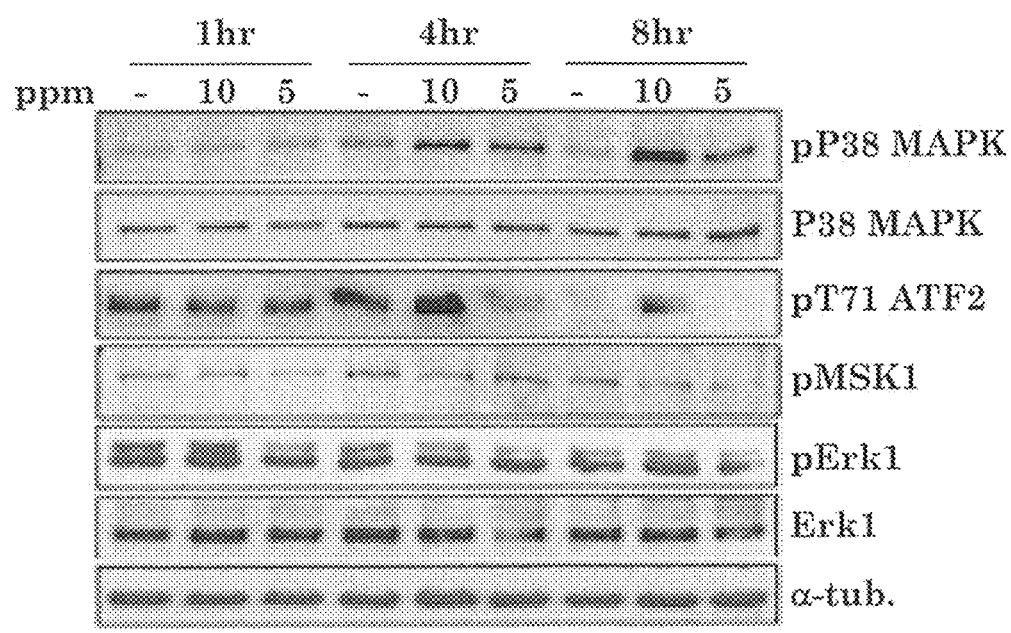
Figure 13B:
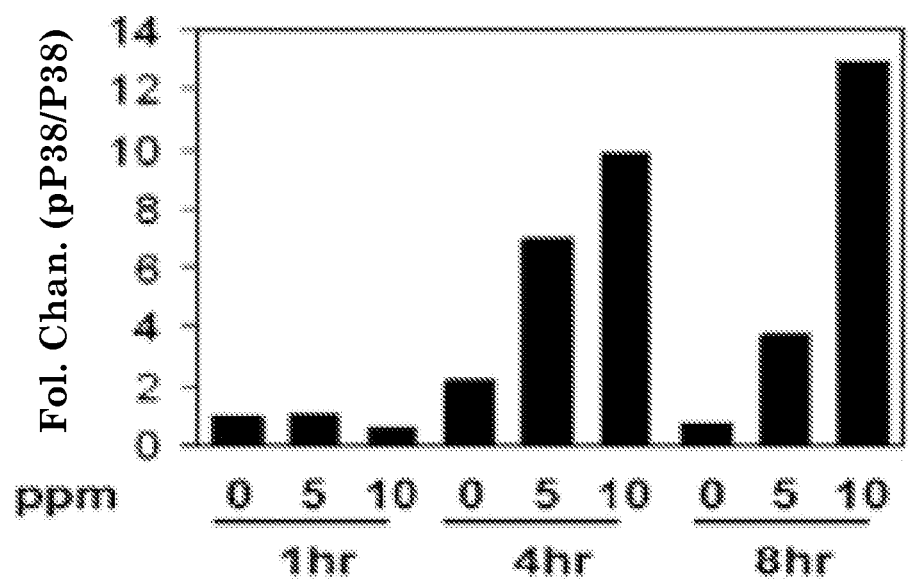
Figure 13C:
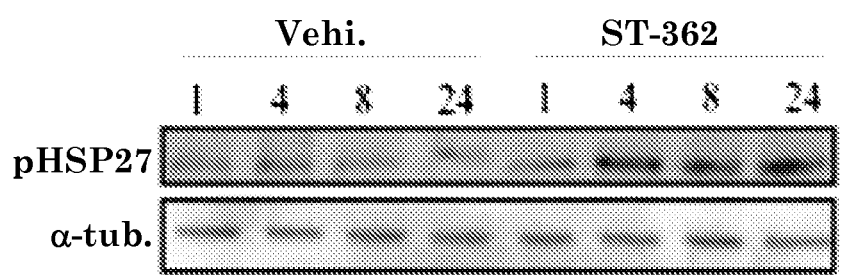
Figure 13D:
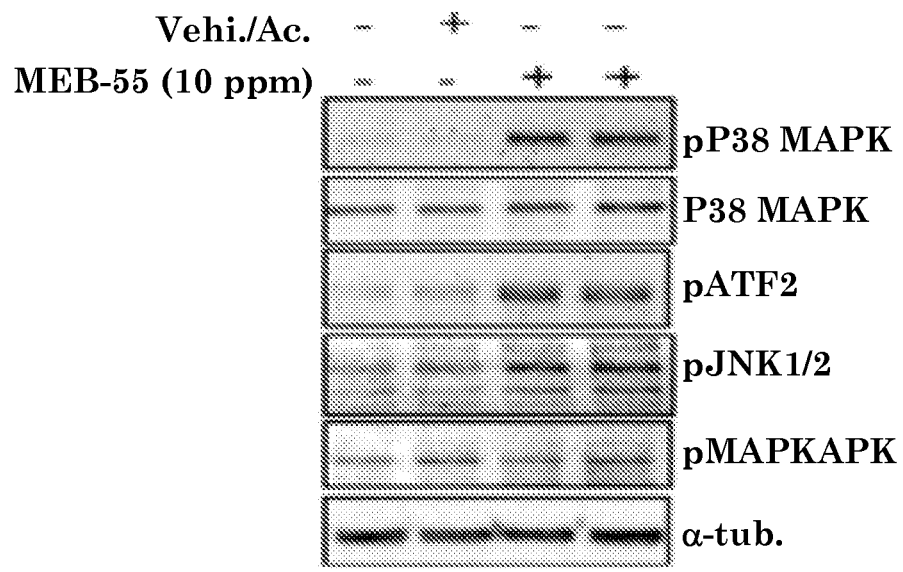
Figure 13E:
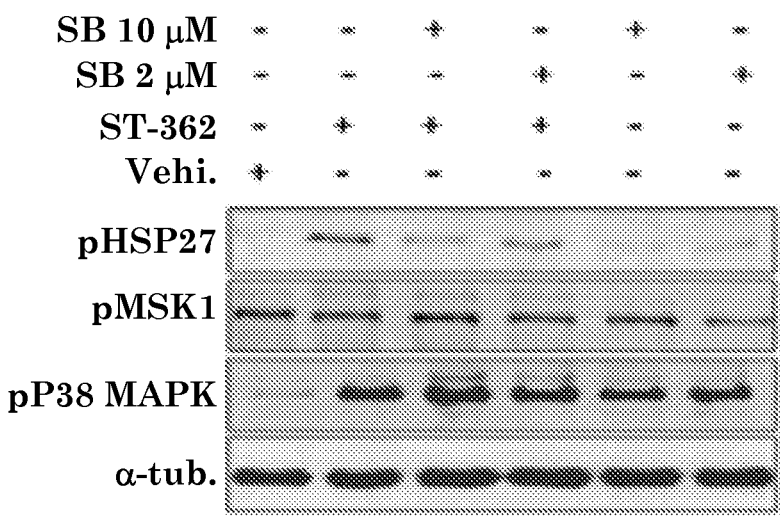
Figure 13F:
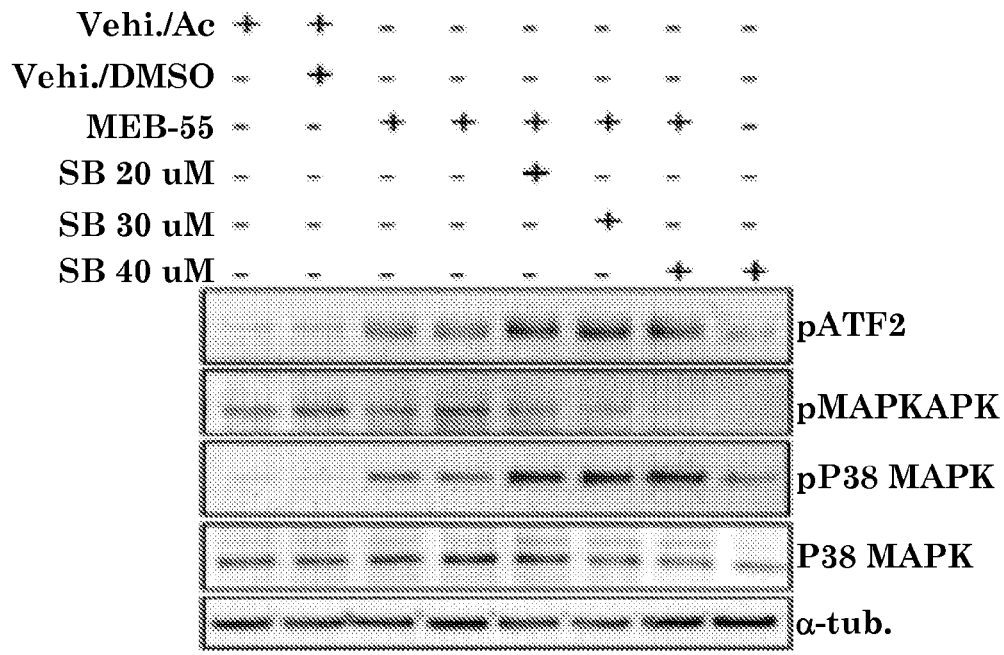

Immunoblot analysis of MDA-MB-231 and HCT116 cells treated with strigolactone analogs was performed. FIG. 13A shows immunoblot analysis of MDA-MB-231 cells following treatment with ST-362 at either 10 or 5 ppm concentration or vehicle alone (−) for the indicated time: there is no change in the total protein levels of ERK1/2 (FIG. 13A) although some dose-independent changes were noted in pERK1/2. However, ST-362 induced a time dependent and dose dependent increase in pP38 levels which was first evident after 4 hours of strigolactone analogs exposure. At 4 hours and 8 hours, pP38 levels increased 5 fold and 13 fold respectively following ST-362 treatment compared to vehicle controls (FIG. 13B—a bar graph showing densitometric quantification of pP38 levels as shown in FIG. 13A). To determine if pP38 levels translated into activation of downstream signaling, nuclear P38 substrates, Activating Transcription Factor 2 (ATF2), which belongs to the ATF/cAMP response element-binding (CREB) protein family of basic region leucine zipper proteins, MSK1 (Mitogen and Stress activated protein Kinase), and heat shock protein 27, HSP27, were analyzed. Phosphorylation of ATF2 and HSP27 was induced in MDA-231 cells in response to MEB-55 or ST-362 (FIG. 13A and FIG. 13C). Levels were markedly increased between 4 and 8 hours after ST-362 treatment and therefore followed a similar time course of activation as pP38 MAPK. There was no change in pMSK1. Importantly, pT581 MSK1 is also a target of ERK1/2, whose phosphorylation was unchanged following strigolactone analog treatment. MEB-55 and ST-362 were also able to induce phosphorylation of P38 ATF2 and HSP27 after 4 hours in MDA-231 cells (FIG. 13D and FIG. 13F). Significant cross talk exists between P38 and JNK1/2 and both modules share subsets of MAPKKKs. Strigolactone analogs treatment also resulted in increased pJNK1/2 after 4 hours (FIG. 13D).

To determine if P38 was directly responsible for the strigolactone induced phosphorylation of ATF2 and HSP27, MDA-231 cells were pretreated with a pharmacological P38 inhibitor, SB203580, for 1 hour prior to the addition of strigolactone analogs, and the cells were treated with ST-362 or MEB-55 alone or together with SB203580 for 4 hours. SB203580 function was confirmed by immuno-blotting for pT334 MAPKAPK, a direct P38 target. pT334 MAPKAPK phosphorylation was decreased in a dose dependent manner following SB203580 exposure (FIG. 13E). pT334 MAPKAPK was not increased upon MEB-55 treatment, like pMSK1 (FIG. 13A and FIG. 13D), indicating that strigolactone treatment induces activation of only specific subset of P38 targets. Pretreatment of MDA-231 cells with SB203580 at concentrations of 2 µM and 10 µM for 1 hour prior to the addition of strigolactone analogs is sufficient to inhibit HSP27 phosphorylation (FIG. 13F) induced by ST-362 and MEB-55, but even 20 µM to 40 µM SB203580 did not inhibit ATF2 phosphorylation following strigolactone analogs treatment (FIG. 13E) and instead resulted in a dose independent increase in pATF2 levels.

pP38 MAPK levels were also increased in SB203580 treated cells, a phenomenon also reported on the reagent datasheet (Cell Signaling Technology, Danvers, Mass.). These results show that P38 is not responsible for ATF2 phosphorylation in this system. ATF2 can also be phosphorylated on T69 and T71 directly by JNK1/2 and by Ras-ERK1/2 pathway. Since ERK1/2 activation did not change upon strigolactone exposure (FIG. 13A), JNK1/2 seems the likely candidate.

Figure 13G:
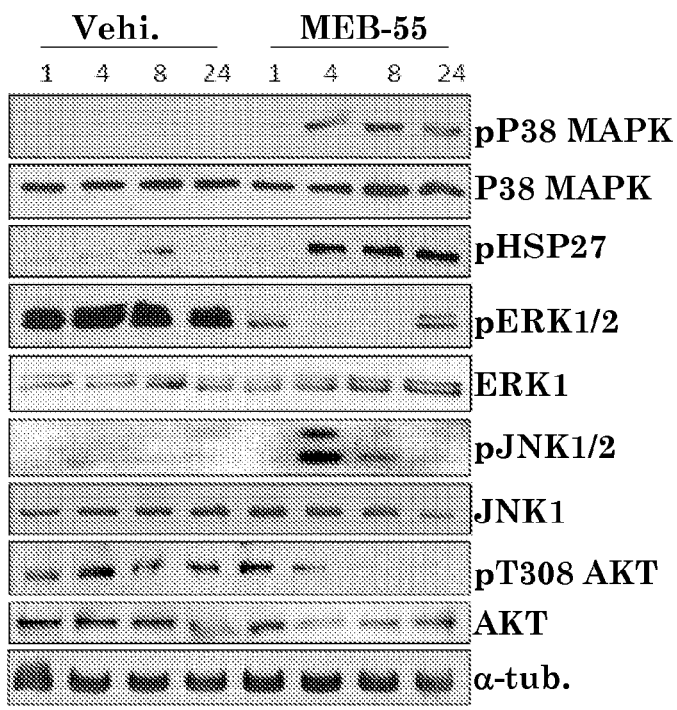
Figure 13H:
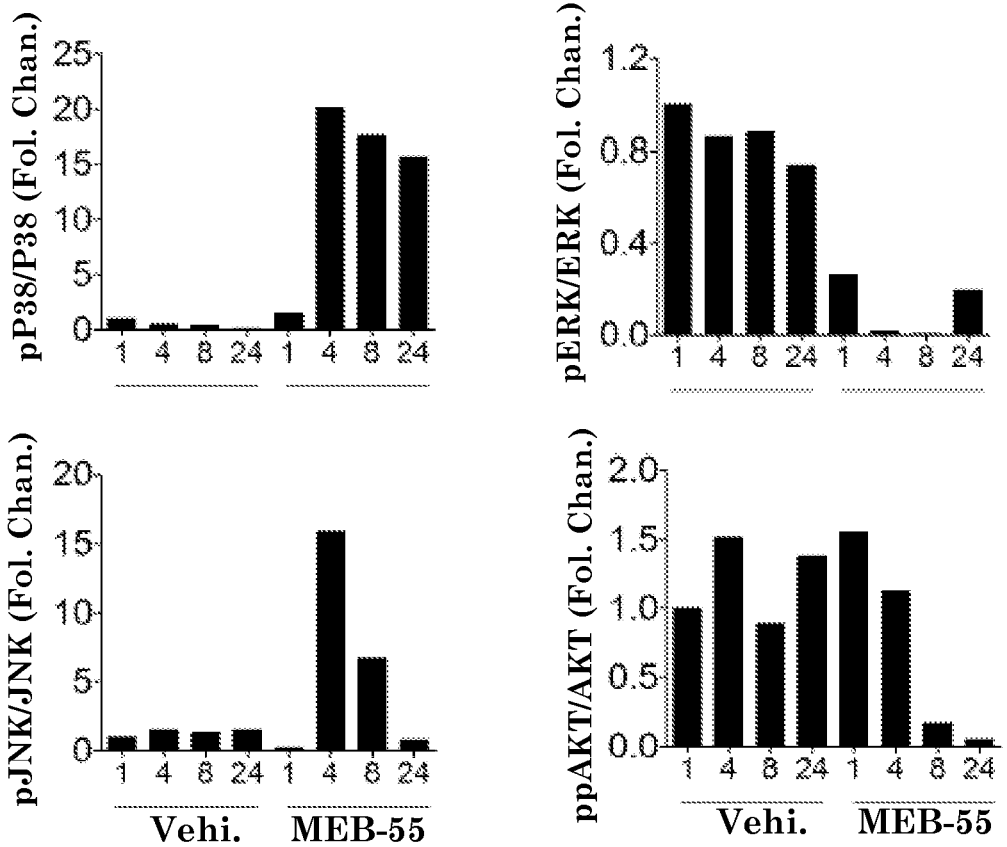
Figure 13I:
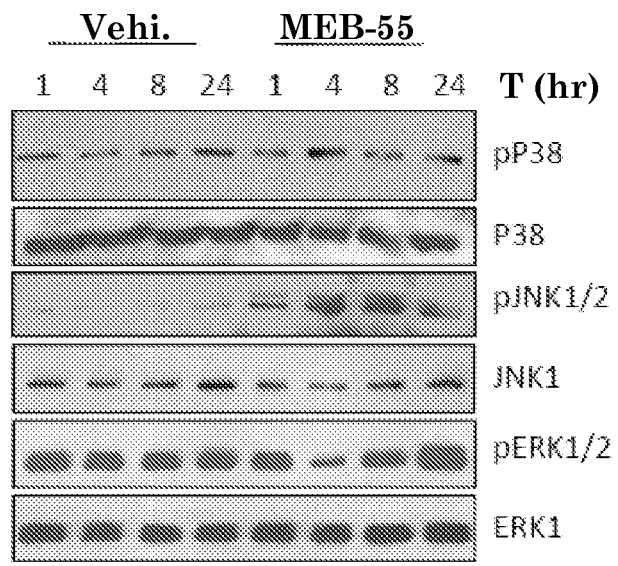

MEB-55 induces a time dependent increase in pP38 which was first evident at 4 hours of strigolactone analogs treatment and remained elevated at 24 hours (FIG. 13G & 14H). HSP27, a downstream target of P38, is phosphorylated directly at Ser15, Ser78 and Ser82 by MAPKAP kinase 2 as a result of the activation of the p38 MAP kinase pathway. In response to MEB-55, pSer82 HSP27 levels were increased in a similar time-dependant manner as pP38. JNK1/2 displayed an acute and robust (15 fold increase) phosphorylation at 4 hours which decreased by 50% at 8 hours and returned to basal levels at 24 hours. In contrast, pERK1/2 levels were reduced 4 fold after 1 hour of treatment which decreased further between 4 and 8 hours and remained suppressed at 24 hours. Likewise, pAKT levels were decreased 6 fold at 8 hours and decreased to undetectable levels at 24 hours. The activation of MAPKs was also examined in the 'normal' BJ-fibroblast line, (FIG. 13I). pP38 levels remained largely unchanged in BJ fibroblast cells following strigolactone treatment. pERK1/2 levels were decreased only at 4 hours but returned to baseline at 8 hours and actually increased above baseline at 24 hours, showing a different kinetic of response than DU145 cells (FIG. 13I).

FIG. 13J is an immunoblot analysis of P38 and pP38 in HCT116 cells following treatments with ST-357 or MEB-55 for 4 hours.

To determine if stress activated MAPK activation was required for strigolactone analogs induced growth inhibition and apoptotic induction, pharmacological inhibitors of P38 (SB203580) and JNK1/2 (SP600125) were utilized. DU145 and U20S cells were treated with ST-362 or MEB-55 alone or together with SB203580. Immuno-blot analysis of pHSP27 confirmed that SB203580 was able to completely inhibit strigolactone analogs induced P38 activation (FIG. 13K). Similar analysis with SP600125 only partially reduced the activation of JNK1/2 kinase whilst increased concentrations of SP600125 were toxic to the cells (FIG. 13L). In a subsequent colony survival assays, U20S cells were either pre-treated with 50 µM SB203580 for 2 hours or treated with different doses of ST-362 alone for 6 hours. Cells were then trypsinized and then re-seeded in a limited dilution of $2 \times 10^3$ cells/well in a 6 well plates. Cells were allowed to form colonies for 14 days by which cells were fixed and stained with crystal violet and 70% EtOH. Colonies of 50 cells or more were counted and survival curves are presented in FIG. 13M. While increasing concentrations of ST-362 reduced cell survival, pre-treatment of cells with SB203580 was partially able to enhance cell survival and rescue the strigolactone analogs inhibitory function.

Strigolactone Analogs Inhibit the Survival Signaling Pathway

The PI3K/AKT pathway regulates a wide range of cellular functions including survival and proliferation. AKT activation requires phosphorylation of two critical residues, S473 near the carboxyl terminus which is considered a requirement for subsequent T308 phosphorylation and maximal AKT activation. pT308 AKT levels decreased dramatically between 4 and 8 hours in cell treated with MEB-55 and remained low at 24 hours (FIG. 14). Cells treated with the less potent strigolactone analog, EG-5, displayed a slight delay in the inhibition of AKT phosphorylation, occurring between 8 and 24 hours. GSK3α/β activity is inhibited by phosphorylation on S9. pS9/21GSK3α/β did not correlate closely with pAKT, however decreased pGSK3α/β was observed after 24 hours (FIG. 14). PDK1 phosphorylates AKT on T308, which is itself activated by phosphorylation on S241. Levels of pS241 PDK1 were reduced upon strigolactone treatment and correlated closely with reduced AKT phosphorylation observed in strigolactone treated cells (FIG. 14). These results show that strigolactone analogs inhibit the survival signaling pathway.

Colon Cells Undergo G2/M Arrest and Apoptosis in Response to Strigolactone Treatment Cell cycle progression from G2 to mitosis (M) is accompanied by an accumulation of Cyclin B1. Cyclin B1 complexes with Cdk1(Cdc2) to form the Maturation Promoting Factor (MPF) which is involved in the early events of mitosis such as chromosome condensation, nuclear envelope breakdown, and spindle pole assembly.

Figure 17A:
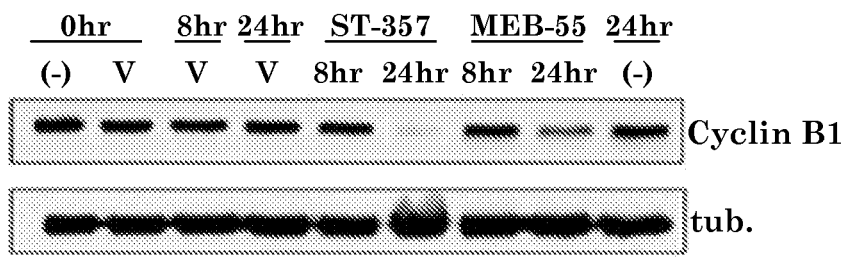

HCT116 cells were seeded out at $4 \times 10^5$ cells per well into three 6-well plates in 10% DMEM media. The following day the media was replaced with growth media supplemented with the indicated strigolactone analog (10 ppm) or vehicle alone (vehi.). Cells were incubated for either 8 or 24 hours. Resulting lysates were immunoblotted for cyclin B1 and tubulin as loading control (FIG. 17A).

Figure 17B:
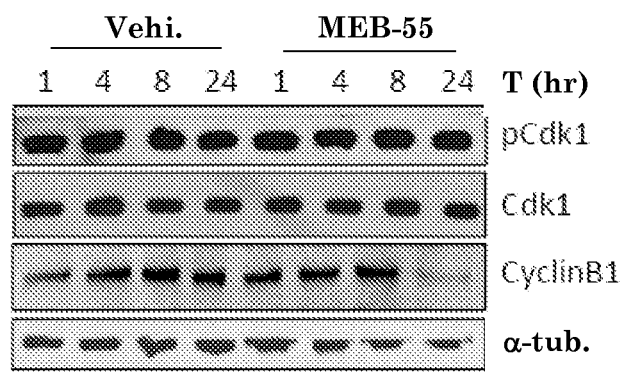
Figure 17C:
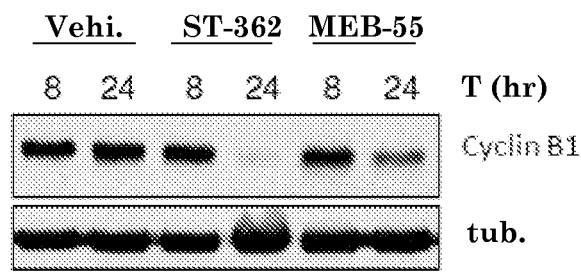
Figure 17D:
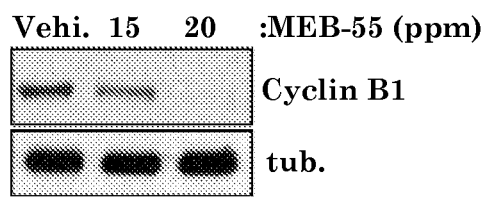
Figure 17E:
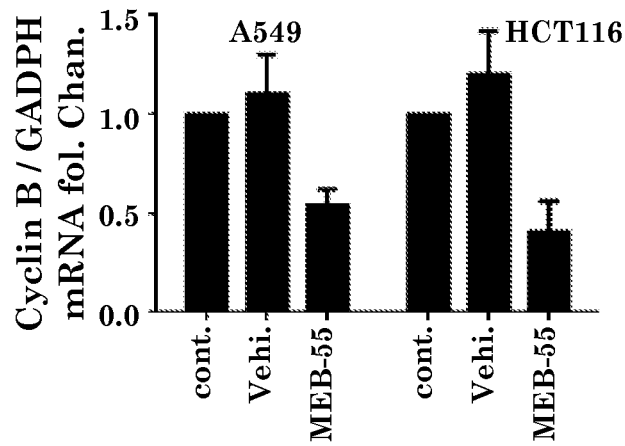

Western blot analysis of cyclin B1 levels in DU145 (FIG. 17B), HCT116 (FIG. 17C) and A549 (FIG. 17D), show that Cyclin B1 levels are decreased 5-10 fold following 24 hours of strigulactone analogs treatment. No change in cyclin B1 levels were detected at earlier time points. The dephosphorylation of Cdk1 (Cdc2) at Thr14 is a critical event for its activation, permitting mitotic entry. Cdk1 protein levels remained unaltered, as did pT14Cdc2 levels (FIG. 17B). Quantitative Real-time PCR was carried out to determine whether Cyclin B1 inhibition was partially at the transcriptional level. A two fold decrease in Cyclin B1 mRNA were observed in HCT116 and A549 cells that were treated with 10 ppm of MEB-55 compared to vehicle controls (FIG. 17E).

Figure 17F:
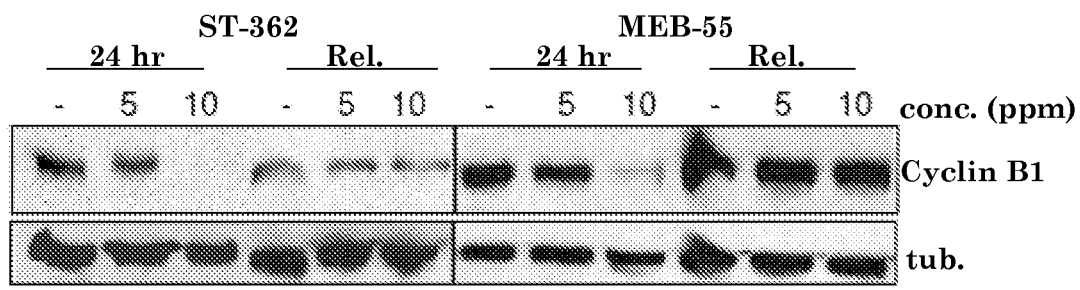
Figure 17G:
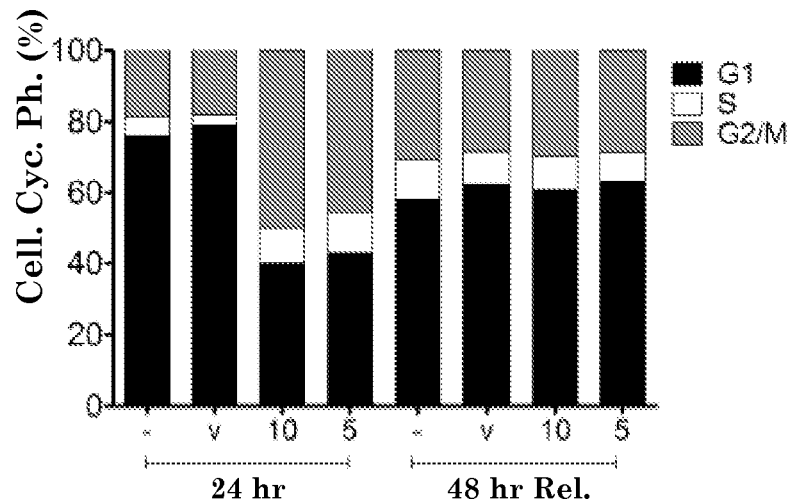

To determine whether the inhibition of Cyclin B1 was reversible, DU145 cells were treated with either ST-362 or MEB-55 for 24 hours, cells were then washed in PBS and media replaced with normal growth media without strigulactone analogs for a further 24 hours. MEB-55 and ST-362 treatment reduced Cyclin B1 levels in a dose dependant manner and Cyclin B1 protein levels returned to that of vehicle alone controls after strigolactone removal (FIG. 17F). To determine whether the strigolactone analogs induced G2 arrest, is also reversible upon strigolactone removal, DU145 cells were treated with MEB-55 for 24 hours, washed twice in PBS and then over-layed with fresh growth media minus MEB-55 and incubated for a further 48 hours (FIG. 17G). Results show that at concentrations of 5 and 10 ppm, MEB-55 induced an increase in the G2/M fraction from 18% to 46% and 50% respectively. 48 hours following strigolactone analogs removal the G2/M fraction decreased in both 5 and 10 ppm treated cells to 29% compared to control cells whose G2/M fraction has also increased at this time to 30.7% (untreated) and 28.5% (vehicle control).

Figure 17H:
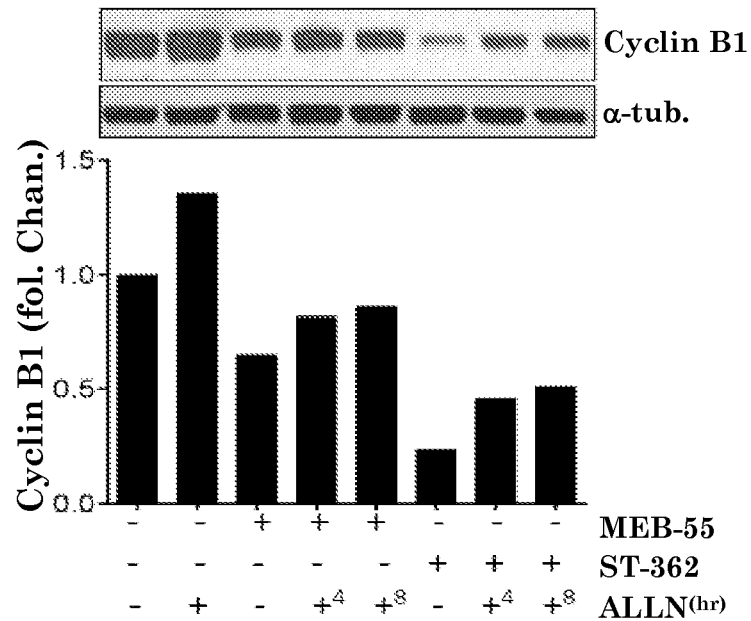

During cell cycle progression, Cyclin B1 levels are regulated by APC/C dependant proteosomal degradation at the metaphase-anaphase transition. To determine whether strigolactone analogs inhibit cell cycle progression through modulation of Cyclin B1 stability, DU145 cells were treated with either MEB-55 or ST-362 for 24 hour. The proteosome inhibitor, ALLN, was then added to the media for a further 4 or 8 hours (FIG. 17H). Results show that ALLN treatment induces a partial rescue (ST-362; 2 fold, MEB-55; 1.3 fold) of Cyclin B1 levels following strigolactone analogs treatment. However, Cyclin B1 levels remains lower than in control lysates, indicating that strigolactone analogs regulate Cyclin B1 levels only partially through enhanced degradation.

Strigolactones and other strigolactone analogs possess inhibitory effects towards breast cancer cells lines growth and survival. All the demonstrated strigolactone analogs induce a G2/M arrest with varying degrees of apoptosis in breast cancer cells lines. Non-tumor 'normal' lines (MCF10A and BJ fibroblasts) displayed only limited growth inhibition and only at the highest dose ranges tested, suggesting that tumorigenic cells are more sensitive to the growth inhibitory effects of strigolactone analogs and that strigolactone analogs induce different responses in cancer and normal cells. Furthermore strigolactone inhibitory effects were not limited to breast cancer cells and colon, lung and prostate cancer cells, but also exhibit increased sensitivity to growth inhibition effects of strigolactone analogs. ST-362 and MEB-55 induce a non-reversible reduction in cell viability after only 4 hours which correlated with phosphorylation of p38 MAPK, JNK1/2 and inhibition of AKT. p38 and JNK1/2 are stress activated MAPKs which play a crucial role in stress signaling cascade and are associated with cell cycle arrest and apoptosis in some cell systems. p38 MAPK has been reported to bind to and activate p53 and cause p53 induced apoptosis. Although, strigolactone analogs were able to induce apoptosis in cells expressing both wild-type (MCF-7) and mutant (MDA-MB-231, MDA-MB-436, T47D) p53, MCF-7 cells were less sensitive. While HSP27 phosphorylation was blocked by p38 pharmacological inhibitor, it did not block the increase in ATF2 phosphorylation, which also could be activated by JNK1/2.

The differential response of cells to strigolactone analogs (cytostatic versus cytotoxic) was dose dependent but may also be determined by cell cycle stage. The $IC_{50}$ doses for all exemplified strigolactone analogs were 2-3 fold lower for MDA-MB-231 cells versus MCF-7 cells. This correlates with the elevated proliferation rate of the MDA-MB-231 line (S-Phase fraction, 14-18% versus 2-4% in MCF-7) and further supports a cancer therapeutic role for strigolactone analogs based on their ability to target rapidly dividing cells. Breast cancer cells grown as 'stem-like cell enriched' mammospheres exhibited an increased sensitivity to strigolactone analogs compared to cells grown in monolayer. Strigolactone analogs reduce mammosphere growth and induced mammosphere dissociation, which correlated with their ability to decrease viability. The similar effects of strigolactone analogs towards plant stem cells indicate universal mechanisms of action, and due to their structural similarity to natural strigolactones, indicate that the latter act in a similar manner.

Strigolactone Analogs Induced Gene Expression Changes

To further elucidate the transcriptional program by which strigolactone analogs may affect growth and survival of cancer cells, U20S cells were treated with ST-362 or MEB-55 (5 ppm) for either 6 or 24 hours to permit early and late gene expression changes to be distinguished. U20S cells were selected based on their enhanced sensitivity to strigolactone treatment (see FIG. 7). After 6 hours of strigolactone analogs exposure, a marked stress response was observed with elevated expression of heat shock proteins (HSPA6, HSPA7, HSP1A, HSP1B, HSPB8) and associated genes, HSPA1L, AHSA1. Strigolactone analogs exposure also induced changes in the expression of genes involved in metabolic functions (SLC3A2, SLC44A2, SLC31A2, SLC7A11, ABCB1, CYP24A1, PTGS2/COX2, ALDH1B1) and transcription factors (ATF3, FOX01, FOXD1). Up-regulation of cytokines (CCL3L3, GDF15) and growth factors (PGF), and down-regulation of TGFBR11 was also noted. Apoptosis regulating genes were also identified, including DDIT3, $BIRC_3$ and BAG3. DDIT3 encodes a member of the CCAAT/enhancer-binding protein (C/EBP) family of transcription factors and functions as a dominant-negative inhibitor by forming heterodimers with other C/EBP members and preventing their DNA binding activity. DDIT3 is induced by stress, including DNA damage and DDIT3 over-expression can induce cell cycle arrest. After 6 hours, MEB-55 treatment was associated with increased expression of p21cip (CDKN1A), Cyclin F (CCNF), Cyclin A2 (CCNA2) and decreased expression of CDK6, whereas ST-362 induced only a modest down-regulation of Cyclin B1 (CCNB1). Therefore, changes in the expression profile of cell cycle regulators, was not a global hallmark of strigolactone exposure. The only exception was Cyclin G2 (CCNG2) whose expression was elevated in both ST-362 and MEB-55 treatment groups. Cyclin G2 is an unconventional cyclin homolog which is linked to growth inhibition and whose expression is induced by DNA damaging chemotherapeutics.

Strigolactone analogs treatment for 24 hours was marked by an up-regulation of genes involved in RNA processing and translation (RN7SK, SNORD3A, SNORD3C, SNORD 3D) and altered expression of genes involved in cellular adhesion (LAMA1, AMPH, ITGA2, SPP1/OPN1, ESM1, CYR61). ESM1 expression was the second (21.2-fold) and third (6.9-fold) most up-regulated gene in MEB-55 and ST-362 treated groups respectively. ESM1 is a secretory proteoglycan, whose expression is up-regulated by inflammatory cytokines. Altered expression of ESM1 has also been shown to induce cell cycle arrest. In contrast to the 6 hours time point, 24 hours of strigolactone analogs treatment was not associated with an up-regulation of heat shock proteins, with a single heat shock protein (HSPA5) being down-regulated in both ST-362 and MEB-55 treatment groups. Several metabolic genes exhibited altered expression patterns (DHRS2, SLC7A11, DUSP5, SCG5, ABCA13), as well as transcription factors (E2F2, $EGR_1$) and growth factors (TGFB1, CTGF). $BIRC_3$, which encodes a member of the IAP family of proteins and is an inhibitor of apoptosis, remained up-regulated in 24 hours treatment groups. Surprisingly, the only gene involved in cell cycle regulation, altered in both ST-362 and MEB-55 treatment groups after 24 hours was KIF20A, which is a mitotic kinesin involved in cytokinesis. Only ST-362 treatment was associated with down-regulation of the other mitotic kinesins (KIF23, KIF4A, KIF11, KIFC1, KIF2C, IF15) and cell cycle regulators, including cyclins (CCNB2, CCNA2, CCNF) and cell cycle regulatory proteins (CCNBP1, CDKN3, CDC2, CDCA3, CDC20, CDC25C, CDCA2). Cyclin B1 also remained down-regulated at 24 hours by ST-362 alone.

Tables 5 and 6 below provides a list of selected genes that are expressed during the treatment of cells with strigolactone analogs for 6 and 24 hours, respectively:

TABLE 6

Differentially expressed genes in strigolactone treated cells following 6 hours

| Function | SYMBOL | DEFINITION | Fold-Change Control vs ST362 | p-value | Fold-Change Control vs MEB55 | p-value |
|---|---|---|---|---|---|---|
| Stress Response | HSPA6 | heat shock 70 kDa protein 6 (HSP70B') | 79.8 | 2.55E−05 | 158.7 | 1.09E−05 |
| | HSPA7 | heat shock 70 kDa protein 7 (HSP70B) | 23.3 | 0.00029098 | 55.7 | 7.45E−05 |
| | HSPA1B | heat shock 70 kDa protein 1B | 9.2 | 2.21E−06 | 12.4 | 1.05E−06 |
| | HSPA1A | heat shock 70 kDa protein 1A | 7.3 | 6.92E−07 | 12.4 | 1.05E−06 |
| | HSPB8 | heat shock 22 kDa protein 8 | 2.7 | 1.43E−05 | 3.6 | 3.18E−06 |
| | HSPA1L | heat shock 70 kDa protein 1-like | 2.7 | 0.00238603 | 3.9 | 0.00044493 |
| | AHSA1 | AHA1, activator of heat shock 90 kDa protein ATPase homolog 1 | 2.1 | 0.0136702 | 2.6 | 0.0044504 |
| Growth Factors | PGF | placental growth factor. | 6.2 | 0.0001284 | 7.0 | 8.86E−05 |
| | FGF2 | fibroblast growth factor 2 (basic) | | | 2.1 | 0.00212148 |
| Cytokines/ Signaling | GDF15 | growth differentiation factor 15. | 7.6 | 3.16E−05 | 19.0 | 3.66E−06 |
| | CCL3L3 | chemokine (C-C motif) ligand 3-like 3 | 3.7 | 0.0371505 | | |
| | TGFBR2 | transforming growth factor, beta receptor II | −2.0 | 0.0158406 | −2.3 | 0.00859784 |
| Apoptosis | DDIT3 | DNA-damage-inducible transcript 3 | 6.2 | 0.00096125 | 14.1 | 0.00012623 |
| | BAG3 | BCL2-associated athanogene 3 | 4.6 | 3.87E−05 | 7.7 | 7.20E−06 |
| | BIRC3 | baculoviral IAP repeat-containing 3 | −2.4 | 0.00864687 | −3.2 | 0.150132 |
| Cellular Adhesion | GEM | GTP binding protein overexpressed in skeletal muscle | 2.4 | 0.00147308 | 4.9 | 1.53E−05 |
| | CLDN12 | claudin 12 | 2.3 | 0.00116056 | 2.5 | 0.00075847 |
| Cell Cycle | CCNB1 | cyclin B1 | −2.1 | 0.00562257 | NA | |
| | CCNG2 | cyclin G2 | 3.6 | 1.59E−05 | 3.1 | 3.16E−05 |
| Metabolism | SLC3A2 | solute carrier family 3 | 3.6 | 0.00297397 | 3.4 | 0.00378565 |
| | SLC44A2 | solute carrier family 44, member 2 | 2.5 | 0.00318131 | 2.1 | 0.00883196 |
| | SLC31A2 | solute carrier family 31 | 2.3 | 8.51E−05 | | |
| | SLC7A11 | solute carrier family 7 | 2.2 | 0.0388166 | 2.1 | 0.0461742 |
| | ABCB1 | ATP-binding cassette, sub-family B (MDR/TAP), member 1 | 3.6 | 0.00024597 | 8.1 | 1.49E−05 |
| | PTGS2 | prostaglandin-endoperoxide synthase 2 | 3.4 | 0.0294943 | 6.9 | 0.00419823 |
| | PPP1R15A | protein phosphatase 1, regulatory subunit 15A | 2.7 | 0.00038012 | 3.7 | 7.56E−05 |
| | CYP24A1 | cytochrome P450, family 24, subfamily A, polypeptide 1 | −2.6 | 0.00057906 | −3.6 | 0.00011394 |
| | ALDH1B1 | aldehyde dehydrogenase 1 family, member B1 | −2.1 | 0.00210428 | −3.1 | 0.00430455 |
| Transcription | ATF3 | activating transcription factor 3 (ATF3) | 2.2 | 0.0184042 | 4.0 | 0.00147967 |
| | FOXO4 | forkhead box O4. | 2.5 | 0.00043792 | 2.2 | 0.0009487 |
| | FOXD1 | forkhead box D1 | −2.4 | 0.0361717 | −2.7 | 0.0212245 |

TABLE 7

Differentially expressed genes in strigolactone treated cells following 24 hours

| Function | SYMBOL | DEFINITION | Fold-Change control vs ST362 | p-value | Fold-Change control vs MEB55 | p-value |
|---|---|---|---|---|---|---|
| Stress Response | HSPA5 | heat shock 70 kDa protein 5 (glucose-regulated protein) | −2.8 | 0.0003223 | −2.1 | 0.0020362 |
| Cytokines/ | GDF15 | growth differentiation factor 15 | 4.2 | 0.0002333 | 2.2 | 0.0046198 |
| Signaling | CCL20 | chemokine (C-C motif) ligand 20 | 6.6 | 3.63E−06 | 11.9 | 7.11E−07 |
| Metabolism | SLC7A11 | solute carrier family 7, (cationic amino acid transporter) | 3.6 | 0.0053044 | 4.1 | 0.0031695 |
|  | DUSP5 | dual specificity phosphatase 5 | 3.9 | 2.83E−05 | 3.8 | 3.26E−05 |
|  | SCG5 | secretogranin V (7B2 protein) | 3.0 | 0.0068693 | 4.9 | 0.001189 |
|  | DHRS2 | dehydrogenase/reductase (SDR family) member 2 | −2.5 | 0.0005996 | −2.3 | 0.0009286 |
|  | ABCA13 | ATP-binding cassette, sub-family A (ABC1), member 13 | −2.8 | 0.0261932 | −2.6 | 0.0340931 |
| Apoptosis | BIRC3 | baculoviral IAP repeat-containing 3 | 2.6 | 0.0062311 | 2.4 | 0.009596 |
| Growth | CTGF | connective tissue growth factor | 2.4 | 0.0176348 | 2.1 | 0.0331052 |
| Factors | TGFBI | transforming growth factor, beta-induced | −3.4 | 0.0006391 | −2.0 | 0.0091635 |
| Transcription | E2F2 | E2F transcription factor 2. | −3.3 | 0.0016412 | −2.2 | 0.0108782 |
|  | EGR1 | early growth response 1 | 2.2 | 0.0086051 | 2.7 | 0.0030771 |
| Cell Cycle | KIF20A | kinesin family member 20A. | −4.7 | 5.56E−06 | −2.4 | 0.0001626 |
|  | CCNB1 | cyclin B1 | −2.2 | 0.0044308 |  |  |
|  | CCNG2 | cyclin G2 | 2.7 | 6.45E−05 |  |  |
| Cellular | LAMA1 | laminin, alpha 1 | 3.0 | 0.000149 | 2.1 | 0.0011095 |
| adhesion | AMPH | amphiphysin | −3.5 | 0.0051844 | −2.7 | 0.0143566 |
|  | ITGA2 | integrin, alpha 2 (CD49B, alpha 2 subunit of VLA-2 receptor) | 3.4 | 0.0018366 | 3.6 | 0.0013518 |
|  | SPP1 | secreted phosphoprotein 1 (SPP1) | 3.9 | 0.017545 | 6.6 | 0.0040549 |
|  | ESM1 | endothelial cell-specific molecule 1 | 6.9 | 0.0007605 | 21.2 | 5.99E−05 |
|  | CYR61 | cysteine-rich, angiogenic inducer, 61 | 3.6 | 0.0022875 | 2.2 | 0.0209306 |
| RNA | RN7SK | RNA, 7SK small nuclear | 16.8 | 3.50E−05 | 15.3 | 4.25E−05 |
| Processing/ | SNORD3A | small nucleolar RNA, C/D box 3A, small nucleolar RNA. | 4.1 | 0.0002884 | 4.2 | 0.0002746 |
| Translation | SNORD3C | small nucleolar RNA, C/D box 3C small nucleolar RNA. | 4.0 | 0.0002162 | 4.8 | 0.0001134 |
|  | SNORD3D | small nucleolar RNA, C/D box 3D small nucleolar RNA. | 4.8 | 9.39E−05 | 4.8 | 9.39E−05 |

Example 7

Tumor Implantation and Treatment

To establish subcutaneous tumors, actively growing MDA-MB-231 breast cancer cells were harvested and 1.5× $10^6$ cells in 100 μl PBS were injected into the mammary fat pads of mice (n=15). The lesions were allowed to grow until their average sizes were approximately 4.5 mm×4.5 mm (about 3 weeks). The mice were then randomized into 3 groups for various treatments including vehicle control, and two strigolactone analogs: ST-362 and ST-357. Treatment started at day 1, 10 ppm (10 mg/Kg) twice a week for a total of 4 treatments. ST-362 and ST-357 were administered intravenously (iv). Body weight and tumor measurements were recorded twice weekly. Tumor cross-sectional area was calculated by multiplying the length×width and tumor volume was calculated by cubing the mean value of length and width. Results are summarized and plotted.

Statistical Analyses

Data are expressed as mean±SD. Statistical significance was assessed by one-way ANOVA and Games-Howell Post Hoc test. A value of P<0.05 was considered significant and represents significance compared with untreated controls, unless indicated otherwise. Data was analyzed by Graphpad PRISMS and SPSS.

Results

Strigolactone analogs inhibit the growth of tumor cells in-vivo xenograft tumor model. The results determine that treatment with 10 mg/kg of strigolactone analogs did not affect animal body weight (FIG. 19). One way Anova and Kruskai-wallis test confirmed that the average and median body weight of all three groups was similar. P=0.2181. MDA-MB-231 cells were injected into SCID mice to generate tumors and when tumors reached 12.5 mm³, treatments with strigolactone analogs were started. Animals were treated twice a week for total of 4 times. As shown in FIG. 18, both ST-362 and ST-357 were effective in inhibiting tumor growth (p<0.0015). The mean tumor volume in the control group was 24.2±5.57 mm³ while the mean of tumor volume in the ST-362 treated mice was 17.7±4.28 mm³ and the mean of tumor volume in the ST-357 treated group was 15.9±2.61 mm³. About 10% of the injected animals showed minor irritation at the site of injection. The animals were sacrificed after the 4$^{th}$ injection according to animal care guidelines.

Example 8

Combined Therapy with Strigolactone Analogs and Standard Chemotherapy Regiments

Systemic therapy of cancer has been dominated by chemotherapy regiments which often cause severe toxic effects. These adverse effects often lead to discontinuation of the treatment. This invention is the first to demonstrate that strigolactone analogs enhance the efficacy of low doses of chemotherapeutic drugs. One of the most commonly used chemotherapeutic drugs, is cisplatin.

Previous XTT viability assays, determine the $IC_{50}$ and the $IC_{20}$ concentrations of ST-362 for MDA-231 breast cancer cells (2.9 ppm and 1.5 ppm, respectively). To determine if these concentrations of ST-362 can enhance the efficacy of low doses of cisplatin, MDA-231 cells were treated with varying concentrations of cisplatin in the presence of ST-362 $IC_{50}$ and $IC_{20}$ concentrations. The combination of ST-362 with low doses of cisplatin ranging for 0.01 to 0.1 µM produced a greater effect than each of the drugs alone (FIG. 20). Analysis of the Combination Index (CI) according to Chou and Talalay (CI<1) by the CalcuySyn Software package (BioSoft) suggest a synergistic interaction between the cisplatin and ST-362 (Table 8):

TABLE 8

Interaction between treatment combinations

| | CI |
|---|---|
| Cisplatin | 0.8 |
| Cisplatin + ST-362 ($IC_{20}$) | 0.597 |
| Cisplatin + ST-362 ($IC_{50}$) | 0.353 |

Example 9

Determination of Natural Strigolactone and Analog Effects on Yeast Cell Culture Growth Materials and Methods
Cell Culture and Growth Conditions

*Saccharomyces cerevisiae* and *Candida oleophila* yeast cells were grown overnight in a reach nutrient media at 28° C., at 150 rpm. Following, they were diluted to 0.4 OD in low nutrient media (Lily) and were divided into 96 wells. The cells were treated with GR-24 or ST-362, at the indicated concentrations. Cell culture growth was monitored every hour for 17 hours, at 28° C., with gentle shake before each OD read. OD was determined using fluorometer.
Statistical Analyses Statistical differences between curves were analyzed using compareGrowthCurves function from the Statistical Modeling package, statmod (http://bioinf.wehi.edu.au/software/compareCurves/), significance was determined once $P \leq 0.05$.
Results Treatment of *Saccharomyces cerevisiae* yeast culture with GR-24 at the indicated concentrations, led to a significant reduction in cell culture growth, which is apparent already 8 hours after GR-24 application (FIG. 21).

Treatment of *Saccharomyces cerevisiae* yeast culture with ST-362 led to a significant reduction in cell culture growth at concentrations of 0.1 µM and above. The effect was apparent from the time of application (FIG. 22). Moreover, treatment of *Candida oleophila* yeast culture in a similar way with ST-362, resulted in a reduction of cell culture growth at concentration of 10 µM and the effect was apparent 8 hours after ST-362 application (FIG. 23).

This is the first study to assess the effects of strigolactones and strigolactone analogs, a novel class of phytohormones, on cell proliferation and on mammalian cells (particularly cancer cells). This work demonstrates that strigolactones and strigolactone analogs represent a new class of antiproliferative therapeutics, as well as anti-cancer therapeutics, which are able to target the bulk tumor and also are effective at targeting 'cancer stem-like cells'. The mechanism of action may involve stress signaling activation and inhibition of survival signaling through inhibition of AKT.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the present invention has been described above in connection with the certain illustrative embodiments, it is to be understood that other similar embodiments may be used or modifications and additions may be made to the described embodiments for performing the same function of the present invention without deviating therefrom. Furthermore, all embodiments disclosed are not necessarily in the alternative, as various embodiments of the invention may be combined to provide the desired characteristics. Variations can be made by one having ordinary skill in the art without departing from the spirit and scope of the invention. Therefore, the present invention should not be limited to any single illustrative embodiment, but rather construed in breadth and scope in accordance with the recitation of the attached claims.

The invention claimed is:

1. A method for inhibiting the proliferation of a cancerous cell in a patient in need thereof, or for inducing death of a cancerous cell in a patient in need thereof, wherein said cancerous cell comes from cancer selected from the group consisting of breast cancer, lung cancer, prostate cancer, colon cancer, leukemia and osteosarcoma, said method comprising the step of administering to said patient an effective amount of a compound of formula III

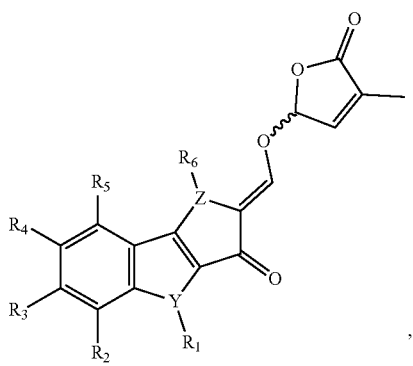

or its stereoisomer or pharmaceutically acceptable salt thereof;

wherein $R_1$ is $C_1$-$C_6$ alkyl;

Z is CH, and Y is N;

$R_6$ is H or $C_1$-$C_6$ alkyl;

$R_2$ and $R_5$ represent H; and one of $R_3$ and $R_4$ represents H whereas the other is selected from the group consisting of H, Halogen, $C_1$-$C_6$ alkyl, heterocyclyl, cycloalkyl, benzcycloalkyl, thienyl, 2,3-dihydrothieno[3,4-b][1,4]dioxin-7-yl, and phenyl or naphthyl substituted with nitro, dialkylamino or methoxy group.

2. The method of claim 1, wherein the compound of formula III or its stereoisomer or pharmaceutically acceptable salt is part of a pharmaceutical composition.

3. The method of claim 2, wherein the pharmaceutical composition further comprises one or more additional pharmaceutically active compounds.

4. The method of claim 1, wherein the compound of formula III is selected from the group consisting of:

(±)(2E)-4-methyl-2-(4-methyl-5-oxo-2,5-dihydrofuran-2-yloxymethylene)-1,4-dihydro-2H-cyclopenta[b]indol-3-one;

(±)(2E)-7-bromo-4-methyl-2-(4-methyl-5-oxo-2,5-dihydrofuran-2-yloxymethylene)-1,4-dihydro-2H-cyclopenta[b]indol-3-one;

(±)(2E)-4-methyl-2-(4-methyl-5-oxo-2,5-dihydrofuran-2-yloxymethylene)-7-(4-nitrophenyl)-1,4-dihydro-2Hcyclopenta[b]indol-3-one;

(±)(2E)-4-methyl-2-(4-methyl-5-oxo-2,5-dihydrofuran-2-yloxymethylene)-7-(2-thienyl)-1,4-dihydro-2H-cyclopenta[b]indol-3-one;

(±)(2E)-4-methyl-2-(4-methyl-5-oxo-2,5-dihydrofuran-2-yloxymethylene)-7-[(4-dimethylamino)-phenyl]-1,4-dihydro-2H-cyclopenta[b]indol-3-one;

(2E)-7-(1-methoxynaphthalen-2-yl)-1,4-dimethyl-2-((4-methyl-5-oxo-2,5-dihydrofuran-2-yloxy)methylene)-1,2-dihydrocyclopenta[b]indol-3(4H)-one;

(2E)-2-[(2,5-dihydro-4-methyl-5-oxofuran-2-yloxy)methylene]-1,2-dihydro-7-[4-(dimethylamino)phenyl]-1,4-dimethyl-cyclopenta[b]indole-3-(4H)-one;

(2E)-1,4-dimethyl-2-((4-methyl-5-oxo-2,5-dihydrofuran-2-yloxy)methylene)-7-(thiophen-2-yl)-1,2-dihydrocyclopenta[b]indol-3(4H)-one;

(2E)-2-[(2,5-dihydro-4-methyl-5-oxofuran-2-yloxy)methylene]-1,2-dihydro-7-(2,3-dihydrothieno[3,4-b][1,4]dioxin-7-yl)-1,4-dimethylcyclopenta[b]indole-3-(4H)-one;

(±)2E-4-methyl-2-(4-methyl-5-oxo-2,5-dihydrofuran-2-yloxymethylene)-6-thiophen-2-yl-1,4-dihydro-2H-cyclopenta[b]indol-3-one;

and any combinations thereof.

* * * * *

SEQUENCE LISTING

<160> NUMBER OF SEQ ID NOS: 2

<210> SEQ ID NO 1
<211> LENGTH: 25
<212> TYPE: DNA
<213> ORGANISM: artificial sequence
<220> FEATURE:
<223> OTHER INFORMATION: synthetic

<400> SEQUENCE: 1
caaaggagtt gatctcgatg ctctt                                    25

```
<210> SEQ ID NO 2
<211> LENGTH: 19
<212> TYPE: DNA
<213> ORGANISM: artificial sequence
<220> FEATURE:
<223> OTHER INFORMATION: synthetic

<400> SEQUENCE: 2
gcctcccttt tcgctttcc                                              19
```